(12) United States Patent
Carley et al.

(10) Patent No.: US 7,403,901 B1
(45) Date of Patent: Jul. 22, 2008

(54) ERROR AND LOAD SUMMARY REPORTING IN A HEALTH CARE SOLUTION ENVIRONMENT

(75) Inventors: Kevin W. Carley, Atlanta, GA (US); Lisa Marie Harrington, Denver, CO (US); Jennifer Scot Dikeman, Atlanta, GA (US); Megan Davies Moody, Denver, CO (US); Mary Michelle Gregory, Atlanta, GA (US)

(73) Assignee: Accenture LLP, Palo Alto, CA (US)

( * ) Notice: Subject to any disclaimer, the term of this patent is extended or adjusted under 35 U.S.C. 154(b) by 0 days.

(21) Appl. No.: 09/549,236

(22) Filed: Apr. 13, 2000

(51) Int. Cl.
*G06Q 50/00* (2006.01)

(52) U.S. Cl. .......................... 705/2; 707/500; 707/522; 707/7; 714/730; 379/111

(58) Field of Classification Search .......... 707/500, 707/522, 7, 3, 100; 714/730; 379/111; 705/2, 705/3
See application file for complete search history.

(56) References Cited

U.S. PATENT DOCUMENTS

| | | | |
|---|---|---|---|
| 3,670,310 A | | 6/1972 | Bharwani et al. |
| 5,146,600 A | | 9/1992 | Sugiura |
| 5,267,155 A | * | 11/1993 | Buchanan et al. ........... 707/522 |
| 5,410,551 A | * | 4/1995 | Edwards et al. ............ 714/730 |
| 5,469,576 A | * | 11/1995 | Dauerer et al. ................ 707/7 |
| 5,546,580 A | | 8/1996 | Seliger et al. |
| 5,715,397 A | | 2/1998 | Ogawa et al. |
| 5,721,943 A | | 2/1998 | Johnson |
| 5,787,450 A | | 7/1998 | Diedrich et al. |
| 5,799,073 A | * | 8/1998 | Fleischer et al. ............ 379/111 |
| 5,805,900 A | | 9/1998 | North |
| 5,859,972 A | | 1/1999 | Subramaniam et al. |
| 5,903,889 A | | 5/1999 | De la Huerga et al. |
| 5,909,570 A | | 6/1999 | Webber |
| 5,933,824 A | | 8/1999 | Dekoning et al. |
| 5,974,389 A | | 10/1999 | Clark et al. |
| 6,058,399 A | | 5/2000 | Morag et al. |

(Continued)

FOREIGN PATENT DOCUMENTS

EP 0578406 1/1994

(Continued)

OTHER PUBLICATIONS

PR Newswire, Wyzdom Solutions Releases Web-Enabled Asset Lifecycle Management Software, Apr. 19, 2000; New York; p. 1.*

(Continued)

*Primary Examiner*—Robert Morgan
(74) *Attorney, Agent, or Firm*—Oppenheimer Wolff & Donnelly LLP

(57) ABSTRACT

A system, method and computer program are provided for generating error and summary reports for a data load. A plurality of records to be loaded in a database are received. The records may include medical records. A data management template corresponding to the records is chosen. It is verified that all records to be loaded match the data management template. The records are sent to a database for loading in the database upon validation that the records match the data management template. A report of records that match the data management template and records that do not match the data management template is compiled.

10 Claims, 20 Drawing Sheets

U.S. PATENT DOCUMENTS

| | | | |
|---|---|---|---|
| 6,151,608 | A | 11/2000 | Abrams |
| 6,192,381 | B1 | 2/2001 | Stiegemeier et al. |
| 6,202,070 | B1 | 3/2001 | Nguyen et al. |
| 6,209,004 | B1 * | 3/2001 | Taylor .................. 707/500 |
| 6,240,414 | B1 | 5/2001 | Beizer et al. |
| 6,360,214 | B1 | 3/2002 | Ellis et al. |
| 6,427,143 | B1 | 7/2002 | Isip et al. |
| 6,434,628 | B1 * | 8/2002 | Bowman-Amuah ............ 714/1 |
| 6,438,548 | B1 | 8/2002 | Grim et al. |
| 6,460,076 | B1 | 10/2002 | Srinivasan |
| 6,523,022 | B1 * | 2/2003 | Hobbs .................... 707/3 |
| 6,535,883 | B1 * | 3/2003 | Lee et al. ................ 707/100 |

FOREIGN PATENT DOCUMENTS

| | | |
|---|---|---|
| WO | WO 00 00909 | 1/2000 |
| WO | WO 2098045 A2 * | 12/2002 |

OTHER PUBLICATIONS

Michael Gertz: "Oracle/Sql Tutorial", Database and Information Systems Group, University of California, Davis, 'Online! Jan. 2000, XP002189251, Retrieved from the Internet: <URL:http://www.db.cs.ucdavis.edu/teaching/sqltutorial/tutorial.pdf> 'retrieved on Feb. 5, 2002, p. 9, 1.4.1 Insertions; p. 58, System architecture.

Per Cederqvist et al.: "Version Management with CVS" Signum Support AB, 'Online, 1993, pp. I-II, 1-6, 57-66, XP002199439, Retrieved from the Internet: <URL:http://www.loria.fr/{molli/cvs/doc/cvs.ps> 'retrieved on May 21, 2002, 1.1 What is CVS?, 10 Multiple developers (pp. 57-66).

*Dayco* Statement Regarding Related Applications.

* cited by examiner

ERROR AND LOAD SUMMARY REPORTING IN A HEALTH CARE SOLUTION ENVIRONMENT

FIELD OF THE INVENTION

The present invention relates to report creation and more particularly to compiling summary reports during data loading.

BACKGROUND

Computerized databases are commonly used to store large amounts of data for easy access and manipulation by multiple users. In a centralized computer system, there is a single copy of the data stored at one location, typically a computer. By maintaining a single, centralized database, such a system avoids inconsistencies which might otherwise occur with more than one copy of the data. Nevertheless, the centralized database approach has several drawbacks. First, since only one copy of the data exists, if the data becomes corrupted or inaccessible, the entire system becomes unavailable. Second, with only one copy of data available for read and update purposes, the system may appear slow and time-consuming, especially to multiple users.

Consequently, many of today's organizations, especially those dispersed over several locations, utilize some type of distributed database system. In a distributed system, an organization's data is spread across the storage facilities of several computers or processors. These storage facilities may be located throughout a single building, across several adjacent buildings or at different locations across the country or around the world. These computers or processors are interconnected via a communications network and are referred to as sites or nodes. Each site, moreover, is able to process local transactions which access data retained only at that local storage facility as well as distributed transactions which access data stored on more than one computer.

Computerized databases, both centralized and distributed, are often used to execute transactions. A transaction is a set of data-dependent operations requested by a user of the system. For example, a user may request some combination of retrieval, update, deletion or insertion operations. The completion of a transaction is called a commitment and the cancellation of a transaction prior to its completion is referred to as an abort. If a transaction is aborted, then any partial results (i.e., updates from those operations that were performed prior to the abort decision) must be undone. This process of returning the data items to their original values is also referred to as a roll back. An important aspect of a transaction is atomicity. Atomicity means that all of the operations associated with a particular transaction must be performed or none of them can be performed. That is, if a transaction is interrupted by a failure, the transaction must be aborted so that its partial results are undone (i.e., rolled back) and, if the transaction is completed, the results are preserved (i.e., committed) despite subsequent failures. The classic example of atomicity concerns a transfer of bank funds from account A to account B. Clearly, the system must either perform both the withdrawal and the deposit operations of the transaction or neither operation.

To protect against disruptions caused by the failure of any particular site, most distributed database systems allow additional copies or "replicas" of the data to be made at other sites. That is, a copy of each data item stored on one of the system's database facilities may also exist at the database facilities of other sites. By replicating the data across multiple instances of database facilities, a certain degree of fault-tolerance may be obtained. Furthermore, by having a locally available replica of the database available, the response time of certain transactions may be improved.

Although replicated systems provide the above advantages over non-replicated systems, there are nonetheless inherent costs associated with the replication of databases. To update a single data item, at least one message must be propagated to every replica of that data item, consuming substantial communications resources. Furthermore, in order to manage multiple databases and handle the execution of concurrent transactions, a complicated administrative support mechanism is required. In addition, if the replicated system cannot guarantee consistent updates at all replicas, data integrity may be compromised.

Most commercially available replicated database systems utilize either a distributed transaction approach or a primary-backup approach to replicate the data. In the distributed transaction approach, all database replicas are updated with a single, distributed transaction. That is, whenever a data item is updated by a transaction, all copies or replicas of that data item are updated as part of the same transaction. This approach results in completely synchronized replicas. To ensure atomicity, distributed transaction-based systems must employ an atomic commit protocol, such as the well-known 2 Phase Commit ("2PC") protocol. The basic idea behind 2PC is to determine a unique decision for all replicas with respect to either committing or aborting a transaction and then executing that decision at all replicas. If a single replica is unable to commit, then the transaction must be aborted at all replicas.

More specifically, under the 2PC protocol, a single database manager associated with a single database facility is chosen as the coordinator of the transaction. The coordinator first asks all of the participants (i.e., the other replicas) including itself (if the coordinator is a participant) to prepare for the commitment of a transaction. Each participant replies to the coordinator with either a READY message, signaling that the participant is ready and willing to commit the transaction, or an ABORT message, signaling that the participant is unable to commit the transaction. Before sending the first prepare message, the coordinator typically enters a record in a log stored on stable storage, identifying all of the replicas participating in the transaction. The coordinator also activates a time-out mechanism. Based on the replies received from the participants, the coordinator decides whether to commit or abort the transaction. If all participants answer READY, the coordinator decides to commit the transaction. Otherwise, if at least one participant replies with an ABORT message or has not yet answered when the time-out expires, the coordinator decides to abort the transaction.

The coordinator begins the second phase of 2PC by recording its decision (i.e., commit or abort) in the log. The coordinator then informs all of the participants, including itself, of its decision by sending them a command message, i.e., COMMIT or ABORT. In response, all of the participants write a commit or abort record in their own logs. Finally, all participants send a final acknowledgment message to the coordinator and execute the relevant procedures for either committing or aborting the transaction. The acknowledgment message, moreover, is not simply an acknowledgment that a command has been received, but is a message informing the coordinator that the command has been recorded by the participant in its stable log record. When the coordinator receives the acknowledgment messages from the participants, it enters a "complete" record in its log.

Although widely implemented, the 2PC protocol nonetheless has several disadvantages. First, as set forth above, the protocol requires each replicated database facility to submit a READY message before the transaction can be committed. Thus, in a fully replicated environment, any site or link failure brings all activity to a complete halt until the site or link is repaired, since that site cannot transmit a READY message. That is, until the failed site is recovered, no further transactions may be executed by a system relying on 2PC. Second, 2PC requires the transmission of at least three messages per replicated database per transaction. The protocol thus consumes substantial communications resources and reduces the system's response time and throughput. Third, 2PC requires both the coordinator and all participants to record the commit/abort decision and the final outcome to stable storage. This involves two forced disk writes per participant per transaction, adding significant overhead to this protocol. Other protocols, such as Quorum Consensus, have been proposed as a solution to the first problem, but these other protocols impose even more communications overhead than 2PC and, as a result, they have not been utilized in commercial systems.

In the primary-backup approach, all transactions update a single, specific replica site, referred to as the primary site. These updates are later copied to the other replicas in the system, which are referred to as backup replica sites. The precise manner in which the updates are propagated to the backup sites varies from implementation to implementation. For example, some systems update the backup replica sites as soon as possible, typically resulting in minimal delays of several seconds. Others update the backup sites at specific time intervals or after a specific number of transactions have committed at the primary site. Some systems, moreover, perform the backup function by transferring entire recovery logs in order to perform the transactions at the other backup sites. Still others create a deferred log of transaction requests which are later used to do the updates. Commercial products incorporating the primary-backup approach to replication include Sybase Replication Server, the Oracle Snapshot Facility, Oracle Symmetric Replication, Oracle Standby Database, Ingres/Replicator and DB2 Data Propagator.

One of the apparent advantages of the primary-backup approach is the ability to create a highly available database system by replacing a failed primary with one of the backups, allowing the backup to become the new primary. This approach, however, has several drawbacks. First, update propagation to the backups typically generates a large amount of network traffic, consuming significant network resources. Second, regardless of the precise manner by which updates are propagated, the backups will always lag the primary. Transactions, moreover, are typically executed serially at the backup sites to avoid data inconsistencies resulting from possibly different execution orders at the primary and backup sites. Hence, in high volume applications, backup sites can lag the primary by tens if not hundreds of transactions. This has serious data consistency consequences both during normal processing and, in particular, after failures.

During normal processing, applications typically access the backups for read-only purposes to improve processing capabilities. Nonetheless, as mentioned above, data at the backup sites may be stale, causing potential problems depending on application requirements. Furthermore, after a primary site failure, both database and real world inconsistencies are likely to arise due to update decisions at the new primary based on stale data. For example, if the sale of the last widget in stock was recorded at the primary site but not propagated to any of the backup sites by the time of a primary failure, then the last widget may be sold a second time by a transaction executing at the new primary.

In addition to being prone to data inconsistencies, the primary-backup approach does not automatically allow for transparent failover to a backup site after a primary failure. First, after a primary failure, application clients must be switched over to a new primary. This process involves significant time during which the system is unavailable. Second, since the backup sites are not always consistent with each other, difficulties arise choosing a new primary from the various backups. Moreover, failures that result in network partitions may result in more than one backup declaring itself the new primary.

In addition to the distributed transaction and primary-backup approaches to database replication, at least one attempt has been made to utilize state machines as a basis for replicating data at different sites. This system, however, requires all transactions to be executed serially at all replicas and thus does not support the concurrent execution of transactions. Basically, a state machine is a entity containing a set of states and a set of commands which transform those states such that all of the new states are also contained within the machine. The prior state of the art of the state machine approach to replication management is described in F. Schneider Implementing Fault-tolerant Services using the State-Machine Approach: A Tutorial ACM Computing Surveys 22 (December 1990). The basic idea of the state machine approach is to start with some number of state machines, and arrange for commands to be sent to all state machines where they may concurrently and independently execute. In order to achieve consistent data replication, however, the commands must be deterministic. That is, the commands must produce identical results when operating on identical states. The requirement that commands be deterministic presents a significant problem in applying this approach to database systems (or, more generally, to transaction-based systems).

SUMMARY OF THE INVENTION

The present disclosure provides for generating error and summary reports for a data load. A plurality of records to be loaded in a database are received. The records may include medical records. A data management template corresponding to the records is chosen. It is verified that all records to be loaded match the data management template. All or matching records are sent to a database for loading in the database upon validation that the records match the data management template. A report of records that match the data management template and records that do not match the data management template is compiled.

In one aspect of the present invention, records that match the data management template are separated from records that do not match the data management template. The separated records are sent to a user station if there are records that do not match the data management template.

In another aspect of the present invention, no records are sent to the database if any of the records do not match the data management template. Preferably, the records are loaded into a table before validation of the records. As an option, a notification may be sent to a user station upon detecting a concurrently executing load process.

In an further aspect of the present invention, a system, method, and computer program for generating error and summary reports for a data load, while storing user input data files in a multi-tier client/server architecture, are provided. A connection between multiple user stations and a server having a database is maintained. A plurality of user input data files is received from one of the user stations, including a plurality of user-selected keywords, wherein data contained within the user input data files is organized around the keywords. A data management template is selected corresponding to the keywords. All data to be loaded into the database are validated to match the data management template. The validated data is loaded into the database and a report identifying data that match the data management template and data that do not match the data management template is compiled.

BRIEF DESCRIPTION OF DRAWINGS

The invention will be better understood when consideration is given to the following detailed description thereof. Such description makes reference to the annexed drawings wherein.

DISCLOSURE OF THE INVENTION

Figure 1:
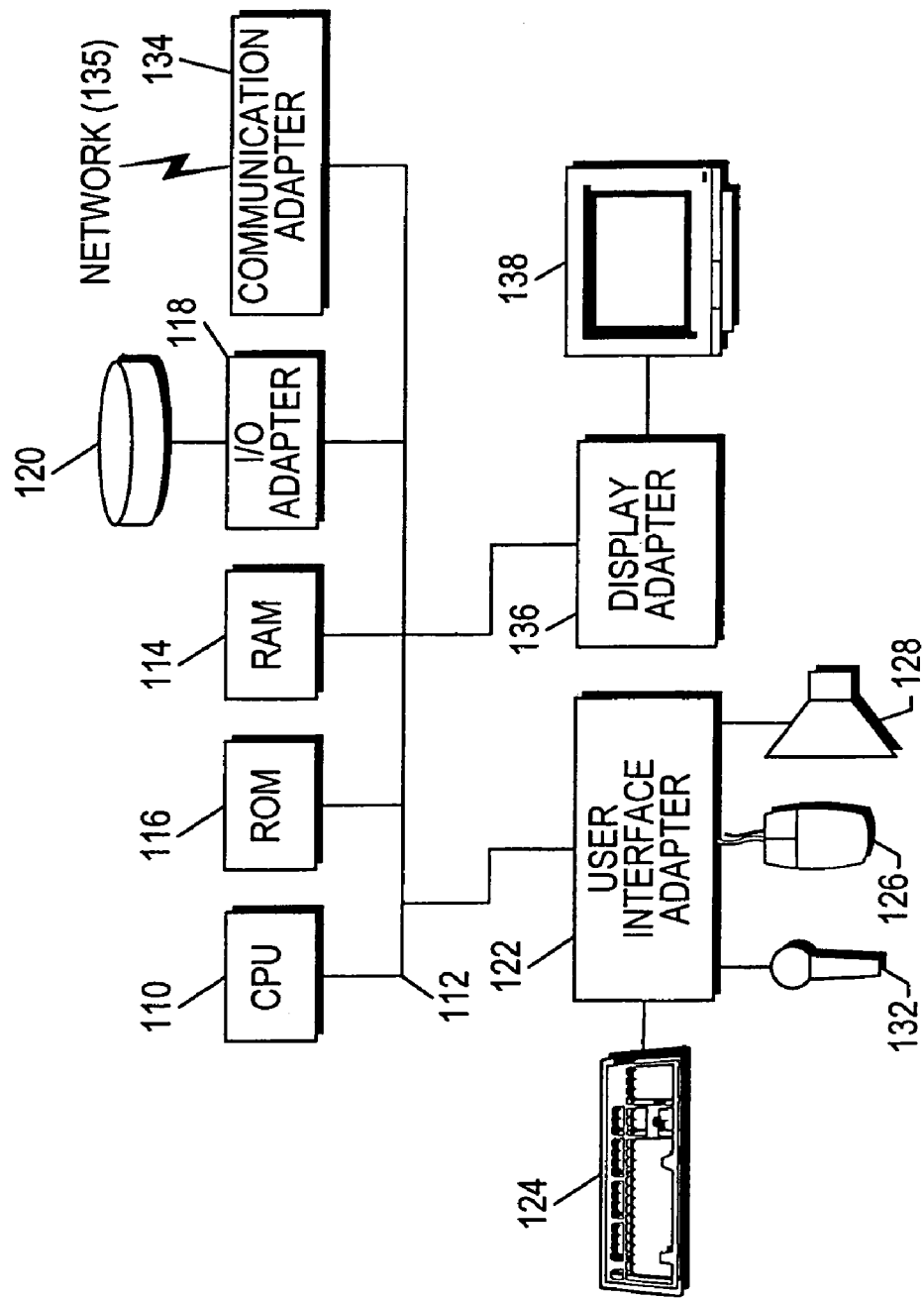
FIG. 1 is a schematic diagram of a hardware implementation of one embodiment of the present invention.

A preferred embodiment of a system in accordance with the present invention is preferably practiced in the context of a personal computer such as an IBM compatible personal computer, Apple Macintosh computer or UNIX based workstation. A representative hardware environment is depicted in FIG. 1, which illustrates a typical hardware configuration of a workstation in accordance with a preferred embodiment having a central processing unit 110, such as a microprocessor, and a number of other units interconnected via a system bus 112. The workstation shown in FIG. 1 includes a Random Access Memory (RAM) 114, Read Only Memory (ROM) 116, an I/O adapter 118 for connecting peripheral devices such as disk storage units 120 to the bus 112, a user interface adapter 122 for connecting a keyboard 124, a mouse 126, a speaker 128, a microphone 132, and/or other user interface devices such as a touch screen (not shown) to the bus 112, communication adapter 134 for connecting the workstation to a communication network (e.g., a data processing network) and a display adapter 136 for connecting the bus 112 to a display device 138. The workstation typically has resident thereon an operating system such as the Microsoft Windows NT or Windows/95 Operating System (OS), the IBM OS/2 operating system, the MAC OS, or UNIX operating system. Those skilled in the art will appreciate that the present invention may also be implemented on platforms and operating systems other than those mentioned.

A preferred embodiment is written using JAVA, C, and the C++ language and utilizes object oriented programming methodology. Object oriented programming (OOP) has become increasingly used to develop complex applications. As OOP moves toward the mainstream of software design and development, various software solutions require adaptation to make use of the benefits of OOP. A need exists for these principles of OOP to be applied to a messaging interface of an electronic messaging system such that a set of OOP classes and objects for the messaging interface can be provided.

OOP is a process of developing computer software using objects, including the steps of analyzing the problem, designing the system, and constructing the program. An object is a software package that contains both data and a collection of related structures and procedures. Since it contains both data and a collection of structures and procedures, it can be visualized as a self-sufficient component that does not require other additional structures, procedures or data to perform its specific task. OOP, therefore, views a computer program as a collection of largely autonomous components, called objects, each of which is responsible for a specific task. This concept of packaging data, structures, and procedures together in one component or module is called encapsulation.

In general, OOP components are reusable software modules which present an interface that conforms to an object model and which are accessed at run-time through a component integration architecture. A component integration architecture is a set of architecture mechanisms which allow software modules in different process spaces to utilize each others capabilities or functions. This is generally done by assuming a common component object model on which to build the architecture. It is worthwhile to differentiate between an object and a class of objects at this point. An object is a single instance of the class of objects, which is often just called a class. A class of objects can be viewed as a blueprint, from which many objects can be formed.

OOP allows the programmer to create an object that is a part of another object. For example, the object representing a piston engine is said to have a composition-relationship with the object representing a piston. In reality, a piston engine comprises a piston, valves and many other components; the fact that a piston is an element of a piston engine can be logically and semantically represented in OOP by two objects.

OOP also allows creation of an object that "depends from" another object. If there are two objects, one representing a piston engine and the other representing a piston engine wherein the piston is made of ceramic, then the relationship between the two objects is not that of composition. A ceramic piston engine does not make up a piston engine. Rather it is merely one kind of piston engine that has one more limitation than the piston engine; its piston is made of ceramic. In this case, the object representing the ceramic piston engine is called a derived object, and it inherits all of the aspects of the object representing the piston engine and adds further limitation or detail to it. The object representing the ceramic piston engine "depends from" the object representing the piston engine. The relationship between these objects is called inheritance.

When the object or class representing the ceramic piston engine inherits all of the aspects of the objects representing the piston engine, it inherits the thermal characteristics of a standard piston defined in the piston engine class. However, the ceramic piston engine object overrides these ceramic specific thermal characteristics, which are typically different from those associated with a metal piston. It skips over the original and uses new functions related to ceramic pistons. Different kinds of piston engines have different characteristics, but may have the same underlying functions associated with it (e.g., how many pistons in the engine, ignition sequences, lubrication, etc.). To access each of these functions in any piston engine object, a programmer would call the same functions with the same names, but each type of piston engine may have different/overriding implementations of functions behind the same name. This ability to hide different implementations of a function behind the same name is called polymorphism and it greatly simplifies communication among objects.

With the concepts of composition-relationship, encapsulation, inheritance and polymorphism, an object can represent just about anything in the real world. In fact, our logical perception of the reality is the only limit on determining the kinds of things that can become objects in object-oriented software. Some typical categories are as follows:

Objects can represent physical objects, such as automobiles in a traffic-flow simulation, electrical components in a circuit-design program, countries in an economics model, or aircraft in an air-traffic-control system.

Objects can represent elements of the computer-user environment such as windows, menus or graphics objects.

An object can represent an inventory, such as a personnel file or a table of the latitudes and longitudes of cities.

An object can represent user-defined data types such as time, angles, and complex numbers, or points on the plane.

With this enormous capability of an object to represent just about any logically separable matters, OOP allows the software developer to design and implement a computer program that is a model of some aspects of reality, whether that reality is a physical entity, a process, a system, or a composition of matter. Since the object can represent anything, the software developer can create an object which can be used as a component in a larger software project in the future.

If 90% of a new OOP software program consists of proven, existing components made from preexisting reusable objects, then only the remaining 10% of the new software project has to be written and tested from scratch. Since 90% already came from an inventory of extensively tested reusable objects, the potential domain from which an error could originate is 10% of the program. As a result, OOP enables software developers to build objects out of other, previously built objects.

This process closely resembles complex machinery being built out of assemblies and sub-assemblies. OOP technology, therefore, makes software engineering more like hardware engineering in that software is built from existing components, which are available to the developer as objects. All this adds up to an improved quality of the software as well as an increased speed of its development.

Programming languages are beginning to fully support the OOP principles, such as encapsulation, inheritance, polymorphism, and composition-relationship. With the advent of the C++ language, many commercial software developers have embraced OOP. C++ is an OOP language that offers a fast, machine-executable code. Furthermore, C++ is suitable for both commercial-application and systems-programming projects. For now, C++ appears to be the most popular choice among many OOP programmers, but there is a host of other OOP languages, such as Smalltalk, Common Lisp Object System (CLOS), and Eiffel. Additionally, OOP capabilities are being added to more traditional popular computer programming languages such as Pascal.

The benefits of object classes can be summarized, as follows:

Objects and their corresponding classes break down complex programming problems into many smaller, simpler problems.

Encapsulation enforces data abstraction through the organization of data into small, independent objects that can communicate with each other. Encapsulation protects the data in an object from accidental damage, but allows other objects to interact with that data by calling the object's member functions and structures.

Subclassing and inheritance make it possible to extend and modify objects through deriving new kinds of objects from the standard classes available in the system. Thus, new capabilities are created without having to start from scratch.

Polymorphism and multiple inheritance make it possible for different programmers to mix and match characteristics of many different classes and create specialized objects that can still work with related objects in predictable ways.

Class hierarchies and containment hierarchies provide a flexible mechanism for modeling real-world objects and the relationships among them.

Libraries of reusable classes are useful in many situations, but they also have some limitations. For example:

Complexity. In a complex system, the class hierarchies for related classes can become extremely confusing, with many dozens or even hundreds of classes.

Flow of control. A program written with the aid of class libraries is still responsible for the flow of control (i.e., it must control the interactions among all the objects created from a particular library). The programmer has to decide which functions to call at what times for which kinds of objects.

Duplication of effort. Although class libraries allow programmers to use and reuse many small pieces of code, each programmer puts those pieces together in a different way. Two different programmers can use the same set of class libraries to write two programs that do exactly the same thing but whose internal structure (i.e., design) may be quite different, depending on hundreds of small decisions each programmer makes along the way. Inevitably, similar pieces of code end up doing similar things in slightly different ways and do not work as well together as they should.

Class libraries are very flexible. As programs grow more complex, more programmers are forced to reinvent basic solutions to basic problems over and over again. A relatively new extension of the class library concept is to have a framework of class libraries. This framework is more complex and consists of significant collections of collaborating classes that capture both the small scale patterns and major mechanisms that implement the common requirements and design in a specific application domain. They were first developed to free application programmers from the chores involved in displaying menus, windows, dialog boxes, and other standard user interface elements for personal computers.

Frameworks also represent a change in the way programmers think about the interaction between the code they write and code written by others. In the early days of procedural programming, the programmer called libraries provided by the operating system to perform certain tasks, but basically the program executed down the page from start to finish, and the programmer was solely responsible for the flow of control. This was appropriate for printing out paychecks, calculating a mathematical table, or solving other problems with a program that executed in just one way.

The development of graphical user interfaces began to turn this procedural programming arrangement inside out. These interfaces allow the user, rather than program logic, to drive the program and decide when certain actions should be performed. Today, most personal computer software accomplishes this by means of an event loop which monitors the mouse, keyboard, and other sources of external events and calls the appropriate parts of the programmer's code according to actions that the user performs. The programmer no longer determines the order in which events occur. Instead, a program is divided into separate pieces that are called at unpredictable times and in an unpredictable order. By relinquishing control in this way to users, the developer creates a program that is much easier to use. Nevertheless, individual pieces of the program written by the developer still call libraries provided by the operating system to accomplish certain tasks, and the programmer must still determine the flow of control within each piece after it's called by the event loop. Application code still "sits on top of" the system.

Even event loop programs require programmers to write a lot of code that should not need to be written separately for every application. The concept of an application framework carries the event loop concept further. Instead of dealing with all the nuts and bolts of constructing basic menus, windows, and dialog boxes and then making these things all work together, programmers using application frameworks start with working application code and basic user interface elements in place. Subsequently, they build from there by replacing some of the generic capabilities of the framework with the specific capabilities of the intended application.

Application frameworks reduce the total amount of code that a programmer has to write from scratch. However, because the framework is really a generic application that displays windows, supports copy and paste, and so on, the programmer can also relinquish control to a greater degree than event loop programs permit. The framework code takes care of almost all event handling and flow of control, and the programmer's code is called only when the framework needs it (e.g., to create or manipulate a proprietary data structure).

A programmer writing a framework program not only relinquishes control to the user (as is also true for event loop programs), but also relinquishes the detailed flow of control within the program to the framework. This approach allows the creation of more complex systems that work together in interesting ways, as opposed to isolated programs, having custom code, being created over and over again for similar problems.

Thus, as is explained above, a framework basically is a collection of cooperating classes that make up a reusable design solution for a given problem domain. It typically includes objects that provide default behavior (e.g., for menus and windows), and programmers use it by inheriting some of that default behavior and overriding other behavior so that the framework calls application code at the appropriate times.

There are three main differences between frameworks and class libraries:

Behavior versus protocol. Class libraries are essentially collections of behaviors that you can call when you want those individual behaviors in your program. A framework, on the other hand, provides not only behavior but also the protocol or set of rules that govern the ways in which behaviors can be combined, including rules for what a programmer is supposed to provide versus what the framework provides.

Call versus override. With a class library, the code the programmer instantiates objects and calls their member functions. It's possible to instantiate and call objects in the same way with a framework (i.e., to treat the framework as a class library), but to take full advantage of a framework's reusable design, a programmer typically writes code that overrides and is called by the framework. The framework manages the flow of control among its objects. Writing a program involves dividing responsibilities among the various pieces of software that are called by the framework rather than specifying how the different pieces should work together.

Implementation versus design. With class libraries, programmers reuse only implementations, whereas with frameworks, they reuse design. A framework embodies the way a family of related programs or pieces of software work. It represents a generic design solution that can be adapted to a variety of specific problems in a given domain. For example, a single framework can embody the way a user interface works, even though two different user interfaces created with the same framework might solve quite different interface problems.

Thus, through the development of frameworks for solutions to various problems and programming tasks, significant reductions in the design and development effort for software can be achieved. A preferred embodiment of the invention utilizes HyperText Markup Language (HTML) to implement documents on the Internet together with a general-purpose secure communication protocol for a transport medium between the client and the Newco. HTTP or other protocols could be readily substituted for HTML without undue experimentation. Information on these products is available in T. Berners-Lee, D. Connoly, "RFC 1866: Hypertext Markup Language—2.0" (November 1995); and R. Fielding, H, Frystyk, T. Berners-Lee, J. Gettys and J. C. Mogul, "Hypertext Transfer Protocol—HTTP/1.1: HTTP Working Group Internet Draft" (May 2, 1996). HTML is a simple data format used to create hypertext documents that are portable from one platform to another. HTML documents are SGML documents with generic semantics that are appropriate for representing information from a wide range of domains. HTML has been in use by the World-Wide Web global information initiative since 1990. HTML is an application of ISO Standard 8879;

1986 Information Processing Text and Office Systems; Standard Generalized Markup Language (SGML).

To date, Web development tools have been limited in their ability to create dynamic Web applications which span from client to server and interoperate with existing computing resources. Until recently, HTML has been the dominant technology used in development of Web-based solutions. However, HTML has proven to be inadequate in the following areas:

Poor performance;

Restricted user interface capabilities;

Can only produce static Web pages;

Lack of interoperability with existing applications and data; and

Inability to scale.

Sun Microsystem's Java language solves many of the client-side problems by:

Improving performance on the client side;

Enabling the creation of dynamic, real-time Web applications; and

Providing the ability to create a wide variety of user interface components.

With Java, developers can create robust User Interface (UI) components. Custom "widgets" (e.g., real-time stock tickers, animated icons, etc.) can be created, and client-side performance is improved. Unlike HTML, Java supports the notion of client-side validation, offloading appropriate processing onto the client for improved performance. Dynamic, real-time Web pages can be created. Using the above-mentioned custom UI components, dynamic Web pages can also be created.

Sun's® Java® language has emerged as an industry-recognized language for "programming the Internet." Sun defines Java as: "a simple, object-oriented, distributed, interpreted, robust, secure, architecture-neutral, portable, high-performance, multithreaded, dynamic, buzzword-compliant, general-purpose programming language. Java supports programming for the Internet in the form of platform-independent Java applets." Java applets are small, specialized applications that comply with Sun's Java Application Programming Interface (API) allowing developers to add "interactive content" to Web documents (e.g., simple animations, page adornments, basic games, etc.). Applets execute within a Java-compatible browser (e.g., Netscape Navigator) by copying code from the server to client. From a language standpoint, Java's core feature set is based on C++. Sun's Java literature states that Java is basically, "C++ with extensions from Objective C for more dynamic method resolution."

Another technology that provides similar function to JAVA is provided by Microsoft and ActiveX Technologies, to give developers and Web designers wherewithal to build dynamic content for the Internet and personal computers. ActiveX includes tools for developing animation, 3-D virtual reality, video and other multimedia content. The tools use Internet standards, work on multiple platforms, and are being supported by over 100 companies. The group's building blocks are called ActiveX Controls, small, fast components that enable developers to embed parts of software in hypertext markup language (HTML) pages. ActiveX Controls work with a variety of programming languages including Microsoft Visual C++, Borland Delphi®, Microsoft Visual Basic® programming system and, in the future, Microsoft's development tool for Java, code named "Jakarta®." ActiveX Technologies also includes ActiveX Server Framework, allowing developers to create server applications. One of ordinary skill in the art readily recognizes that ActiveX could be substituted for JAVA without undue experimentation to practice the invention.

Data Load Process

An embodiment of the present invention is a data load process that automates the process of loading large volume configuration or conversion data into a database in a health care solution framework. The process can be used to automate the normally manual, time intensive process of loading data via a front-end user interface.

The load process can be used to allow a user to:
Create logical sets of data organized around "keywords"
Specify the keywords to be loaded via client GUI
Specify input Data Management Templates (DMT's), or tab or pipe (|) delimited ASCII text files to be loaded via a client GUI
Be notified if multiple users are attempting to alter the same data
Receive continuous status messages throughout the loading process
Review error reports and load summary reports
Maintain database integrity by eliminating insertion of erroneous data The data load process provides the following benefits:
Minimizes configuration problems due to human error
Produces highly replicable and consistent results
Eliminates the insertion of erroneous data by enforcing business rules/requirements and ensuring that referential integrity, codependency, primary key, required field, default field, sequence number, and hard-coded field checks are met.
Minimizes the technical knowledge required on a configuration team in order to load data into the database
Ability for users with little technical knowledge to identify data errors in input files and re-run the load application
Can be used for initial loads of development or testing environments as well as for one-time conversions In one embodiment of the present invention, the keywords are organized into a tier structure, where all keywords within one tier must be loaded before the next tier can be started.

Figure 2:
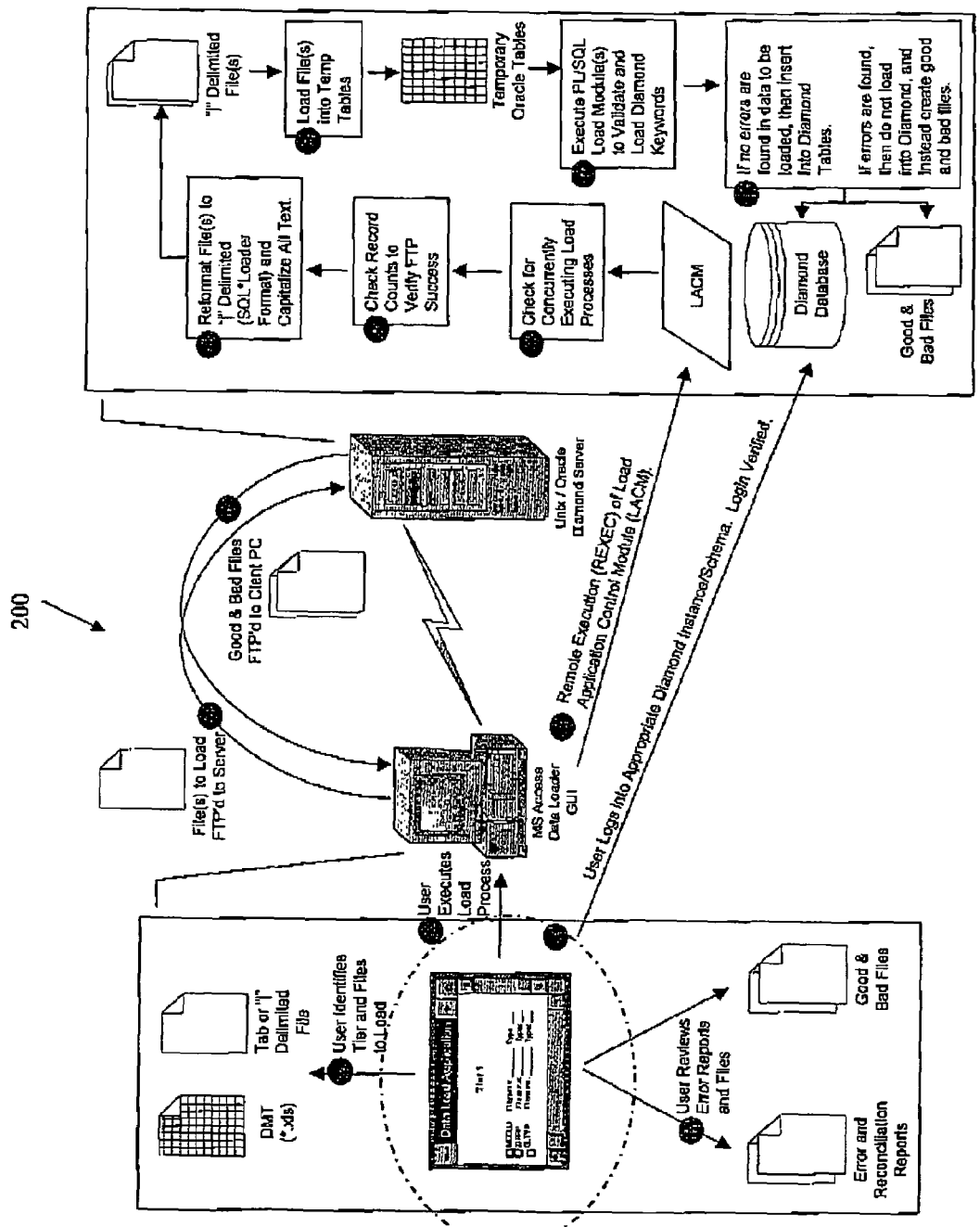
FIG. 2 illustrates a data load process in which a single user runs the process on an individual client desktop (user station)

FIG. 2 illustrates a data load process 200 in which a single user runs the process on an individual client desktop 202 (user station). An illustrative data load process may be embodied in a three tier client/server architecture including a Graphical User Interface (GUI) built in Microsoft Access, a server application built in C, Pro*C, Perl 5 and Unix korn shell scripts, Oracle SQL*Loader scripts, and a series of Oracle PL/SQL stored procedures.

In the data load process, a user logs onto the system. See arrow 1. As shown at arrow 2, the user selects specific keywords within a tier 204 to load into the database 206. The user executes a load process at arrow 3 and files to be loaded are transferred to the server at arrow 4. A load process control module is executed and the corresponding DMT(s) for the selected keyword(s) are sent to the server application. See arrow 5. A check for concurrently executing load processes is performed in operation 6. The success of the file transfer is performed in operation 7. In operations 8 and 9, the files are reformatted and loaded into tables by the server application loads data into worktables. The server application initiates stored PL/SQL procedures to perform validation. See operation 10. Data is validated according to database and/or client-specific business rules. If no validation errors are found, data is loaded into the Diamond database. See operation 11. If errors are found, a file containing all the good records, and a file containing all the bad records are sent back to the client desktop. See arrow 12. A report is produced listing all the erred records and the corresponding row numbers and error messages. Also, a verification report is produced that provides control totals for data loaded into database, or written to good/bad files. The reports can then be reviewed by the user. See arrow 13.

Optionally, in order for data to be loaded, all data on any one DMT must be completely correct. If the Load Application finds any data errors on a DMT, the correct and incorrect records will be written to separate files (i.e.—"good" file and "bad" file), and no data will be inserted into the tables.

Figure 3:
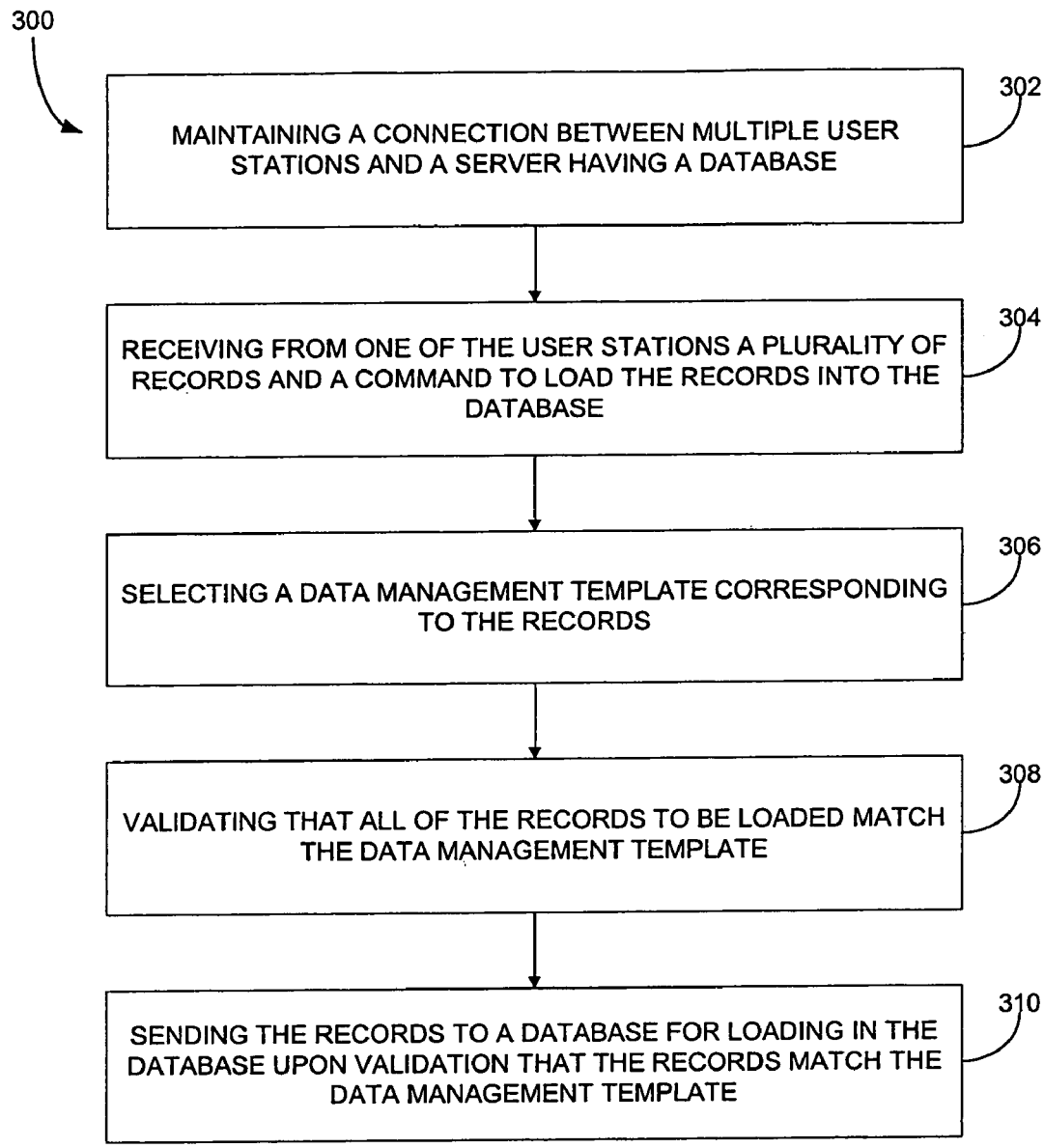
FIG. 3 is a flowchart depicting a process for providing a multi-tier client/server architecture for storing files and/or records.

FIG. 3 is a flowchart depicting a process 300 for providing a multi-tier client/server architecture for storing files and/or records such as medical records. In operation 302, a connection is maintained between multiple user stations and a server that has a database. In this and the other embodiments set forth herein, the connection may be maintained utilizing a local area network or a wide area network. Alternatively, a dialup connection could be created periodically or upon user request. A plurality of records/files and a command to load the records into the database are received from one of the user stations in operation 304. The command may be ordered by the user, or may be executed automatically. If the command is executed automatically, it may be performed at predetermined intervals. In operation 306, a data management template corresponding to the files/records is selected. The data management template may include a listing of all records/files that should be loaded. Alternatively, the data management template may specify particular content of the files/records that must be matched for verification. As another option, the data management template may specify specific particular sizes of the files/records. In operation 308, it is validated that all of the records/files to be loaded match the data management template. In operation 310, the records/files are sent to a database for loading in the database upon validation that the records match the data management template.

In one embodiment of the present invention, files/records that match the data management template are separated from files/records that do not match the data management template. Also, a list of records/files that match the data management template and records/files that do not match the data management template may be compiled and may be sent to the user station.

In another embodiment of the present invention, no records are sent to the database if any of the records do not match the data management template. This prevents entry of erroneous data. Optionally, records that match the data management template are separated from records that do not match the data management template. The records are then sent to the user station if there are records that do not match the data management template.

In yet another embodiment of the present invention, the records are medical records. As an option, a notification is sent to the user station upon detecting a concurrently executing load process.

Figure 4:
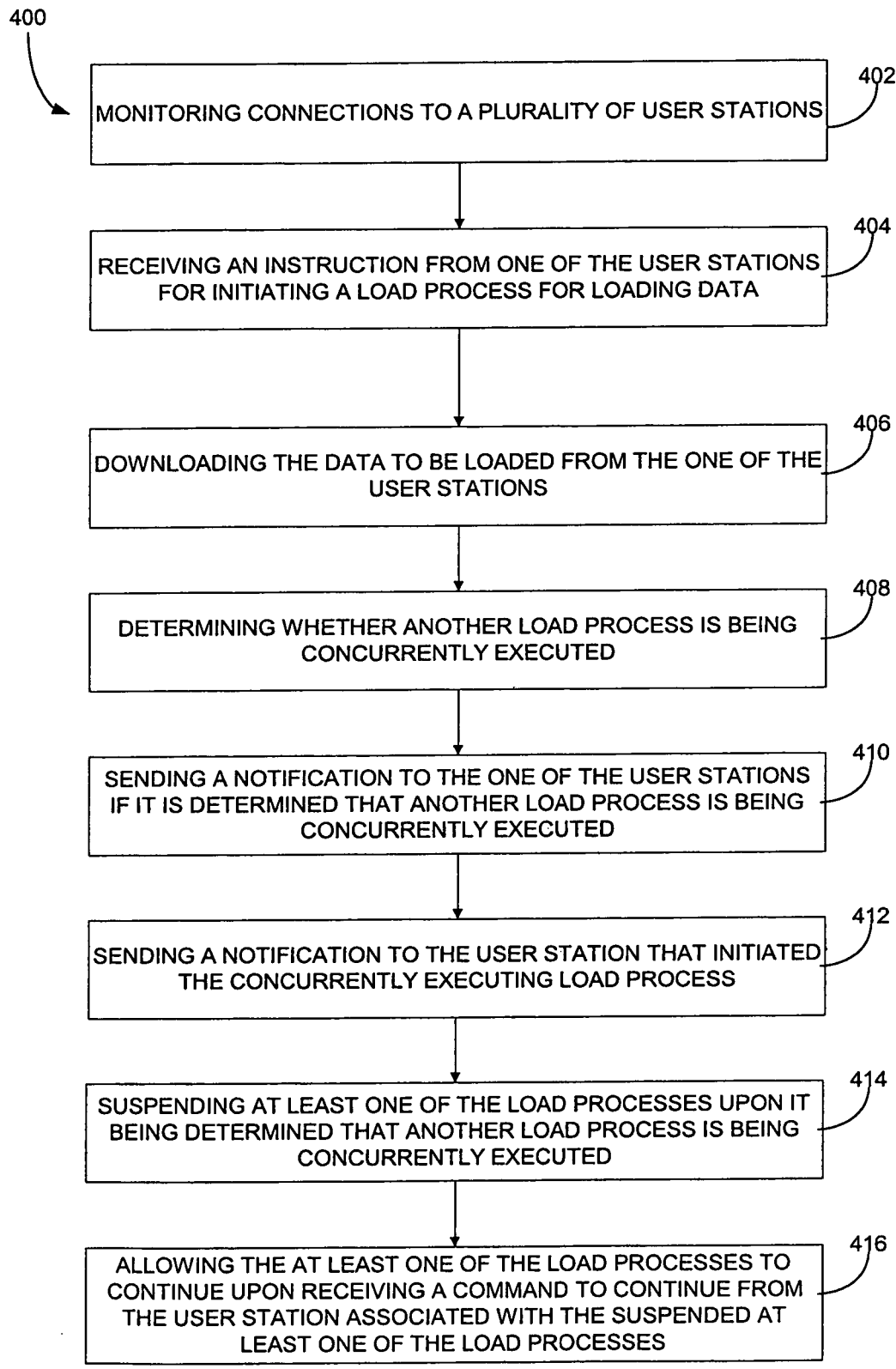
FIG. 4 is a flowchart illustrating a process for providing a notification when multiple users attempt to alter the same data.

FIG. 4 is a flowchart illustrating a process 400 for providing a notification when multiple users attempt to alter the same data. In operation 402, connections to a plurality of user stations are monitored. This may be done continuously or at predetermined intervals, for example. An instruction for initiating a load process is received from one of the user stations in operation 404. Data is downloaded from the one of the user stations in operation 406. In this and other embodiments of the present invention, the data may be in the form of files or records, for example. In operation 408, it is determined whether another load process is being concurrently executed. If it is determined that a load process is being concurrently executed, a notification is sent to the one of the user stations in operation 410. A notification is also sent to the user station that initiated the concurrently executing load process in operation 412. Such notifications may include a pop-up window, an email, and/or a facsimile, for example. Both users are notified to allow them to coordinate their updates so that all alterations to the data are entered.

With continuing reference to FIG. 4, at least one of the load processes is suspended in operation 414 upon detecting the concurrently executed load process to allow the users time to react to the notification. One of the load processes, all but the first load process, all of the load processes, or any other combination can be suspended upon it being determined that another load process is being concurrently executed. At least one of the load processes should be allowed to continue upon receiving a command to continue from the user station associated with the suspended at least one of the load processes. See operation 416.

In one embodiment of the present invention, the data includes medical records. As aforementioned, the connections to the user stations may be via a wide area or local area network.

Figure 5:
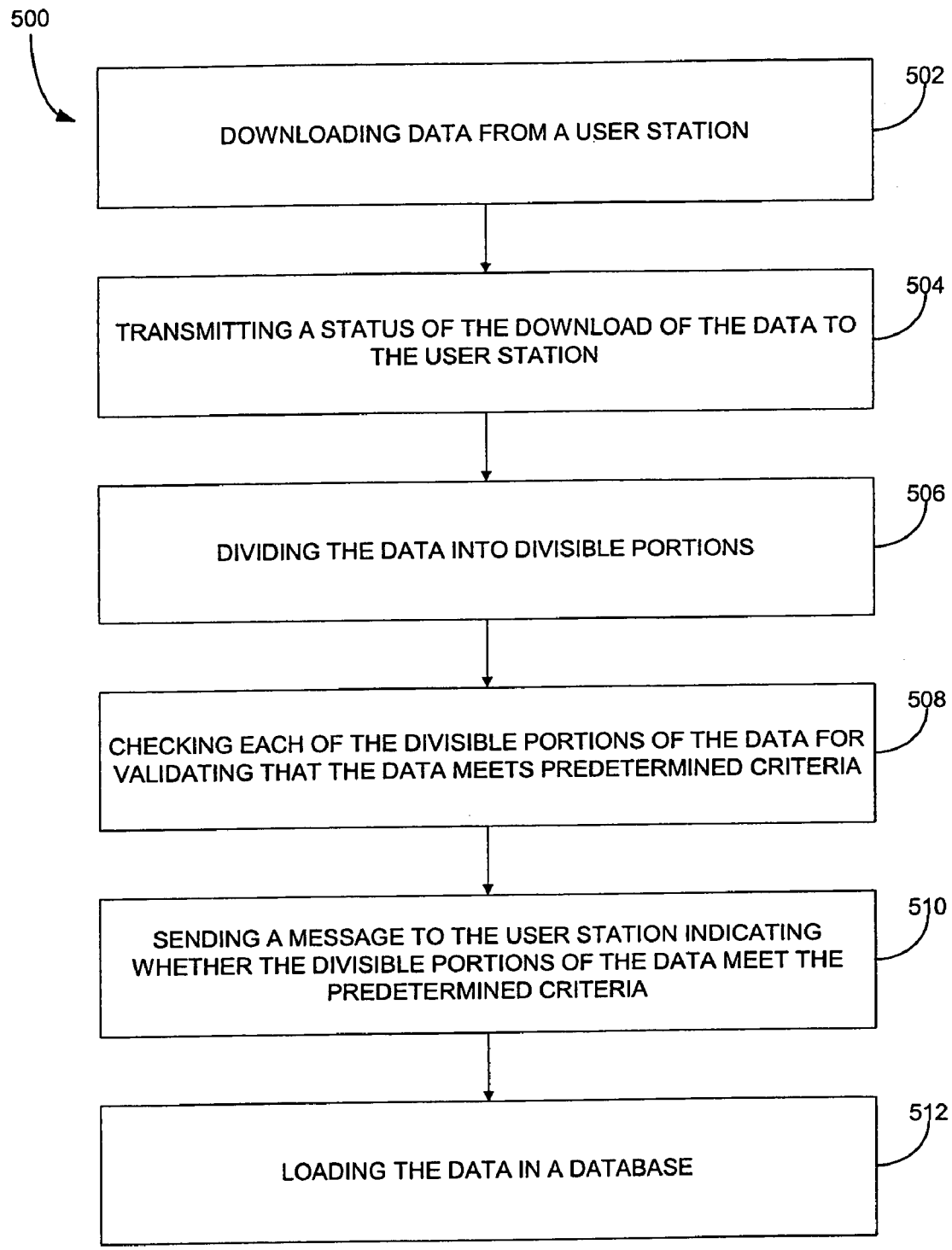
FIG. 5 depicts a process for providing status messaging during data loading in a multi-tier client/server architecture.

FIG. 5 depicts a process 500 for providing status messaging during data loading in a multi-tier client/server architecture. In operation 502, data is downloaded from a user station. A status of the download of the data is transmitted to the user station in operation 504. Preferably, the status is displayed as it is received. In operation 506, the data is divided into divisible portions. Each of the divisible portions of the data is checked in operation 508 to validate that the data meets predetermined criteria, such as that it includes certain content. In operation 510, a message is sent to the user station indicating whether the divisible portions of the data meet the predetermined criteria. The data is loaded in a database in operation 512. The data may include medical records.

In one embodiment of the present invention, a list of data that matches the predetermined criteria and data that does not match the predetermined criteria is compiled. As an option, data that matches the predetermined criteria is separated from data that does not match the predetermined criteria. The separated data is transmitted to the user station. The data may be transmitted during separation or may be transmitted after separation.

Preferably, the divisible portions of the data are loaded into a table before validating that the data meets the predetermined criteria. Optionally, a notification may be sent to the user station upon detecting a concurrently executing load process.

Figure 6:
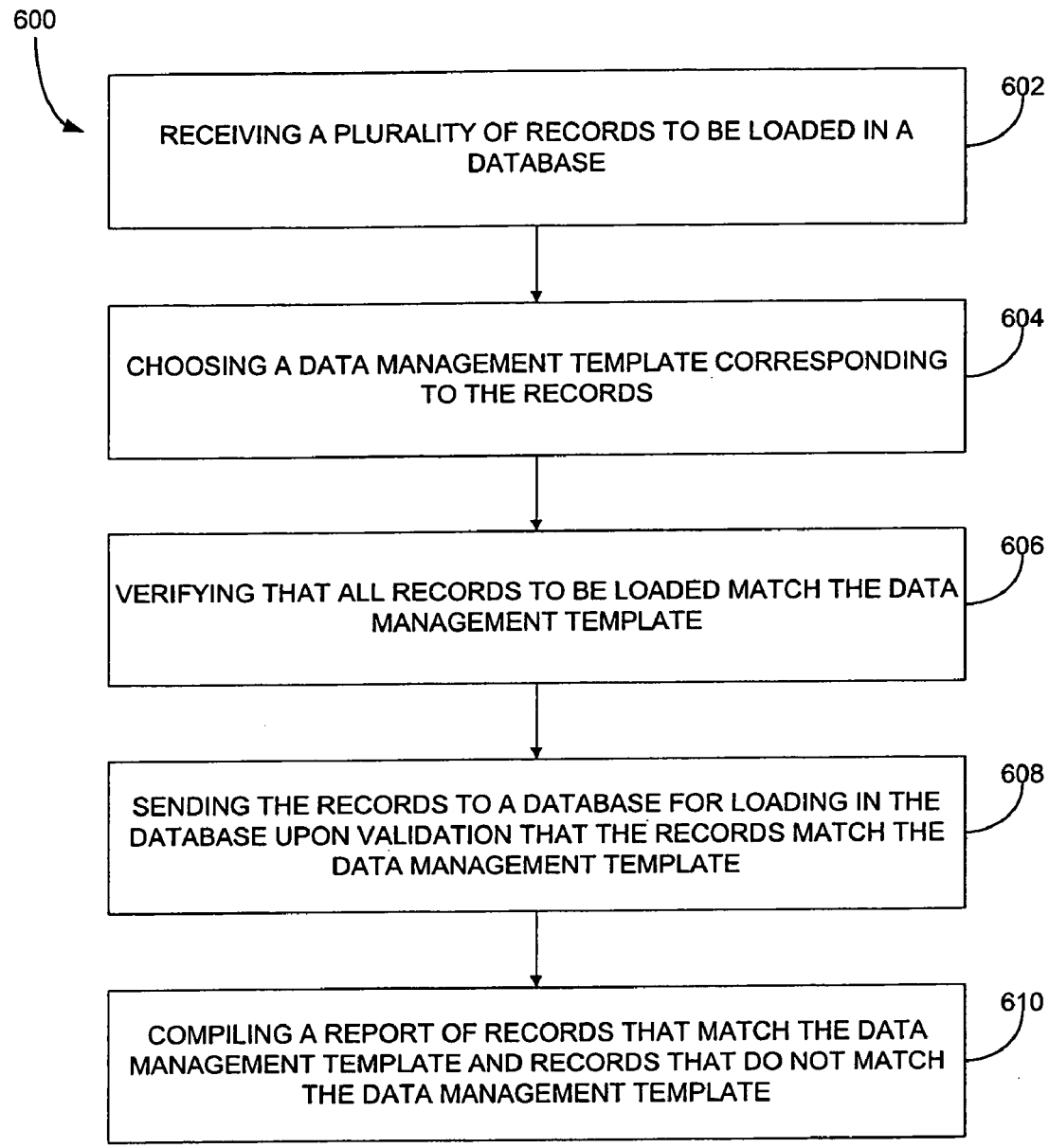
FIG. 6 is a flowchart that illustrates a process for generating error and summary reports for a data load.

FIG. 6 is a flowchart that illustrates a process 600 for generating error and summary reports for a data load. In operation 602, a plurality of records to be loaded in a database are received. The records may include medical records. A data management template corresponding to the records is chosen in operation 604. In operation 606, it is verified that all records to be loaded match the data management template. All or matching records are sent to a database in operation 608 for loading in the database upon validation that the records match the data management template. A report of records that match the data management template and records that do not match the data management template is compiled in operation 610.

In one embodiment of the present invention, records that match the data management template are separated from records that do not match the data management template. The separated records are sent to a user station if there are records that do not match the data management template.

In another embodiment of the present invention, no records are sent to the database if any of the records do not match the data management template. Preferably, the records are loaded into a table before validation of the records. As an option, a notification may be sent to a user station or log file upon detecting a concurrently executing load process.

Figure 7:
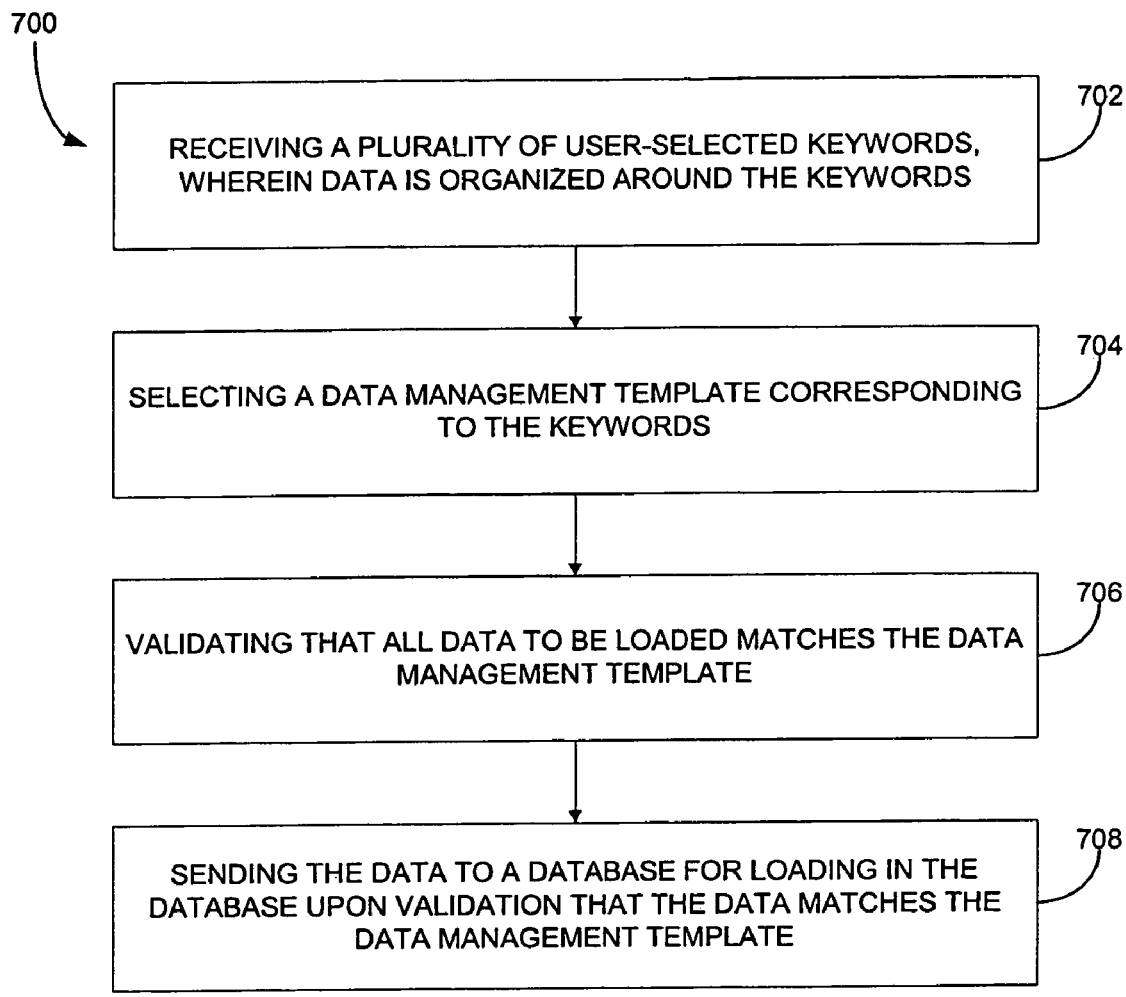
FIG. 7 is a flowchart illustrating a process for loading data in a multi-tier client/server architecture.

FIG. 7 is a flowchart illustrating a process 700 for loading data in a multi-tier client/server architecture. In operation 702, a plurality of user-selected keywords are received. Data is organized around the keywords. The data can include medical-related data such as medical records. A data management template which corresponds to the keywords is selected in operation 704. A validation is performed in operation 706 to determine whether all of the data to be loaded matches the data management template. The data is sent to a database in operation 708 to be loaded in the database upon validation that the data matches the data management template.

In one embodiment of the present invention, data that matches the data management template is separated from data that does not match the data management template. A list of data that matches the data management template and data that does not match the data management template is compiled.

In one embodiment of the present invention, no data is sent to the database if any of the data does not match the data management template for eliminating insertion of erroneous data. In another embodiment of the present invention, the data is loaded into a table before validation of the data. Optionally, a notification is sent to a user upon detecting a concurrently executing load process.

The following discussion with respect to FIGS. 8–20 describes frameworks that may be used to implement the above-described embodiments of the present invention.

Development Framework (Idea)

Figure 8:
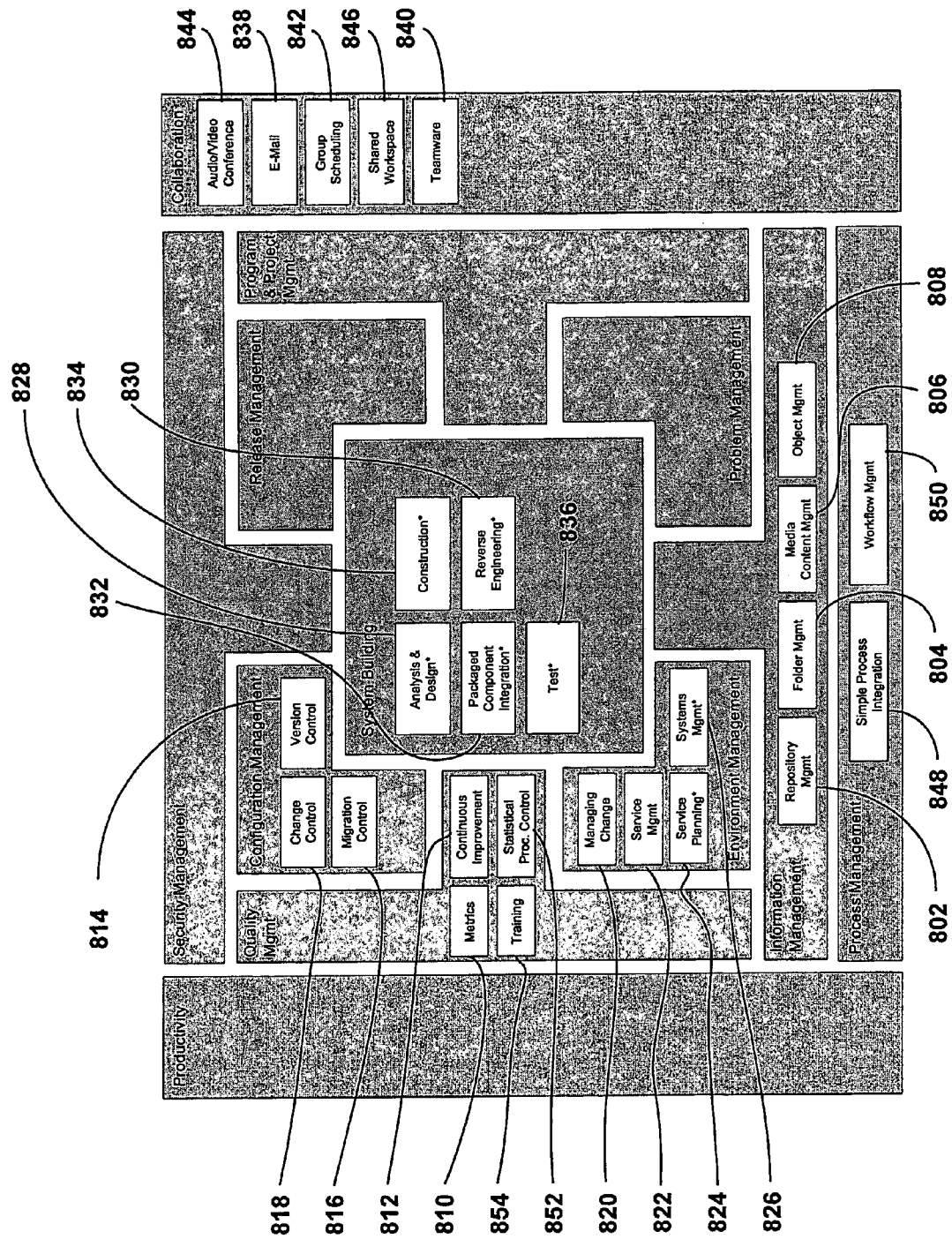
FIG. 8 is an illustration of the Integrated Development Environment Architecture (IDEA)

FIG. 8 is an illustration of the Integrated Development Environment Architecture (IDEA). The Integrated Development Environment Architecture provides a development environment framework and associated guidelines that reduce the effort and costs involved with designing, implementing, and maintaining an integrated development environment. IDEA takes a holistic approach to the development environment by addressing all three Business Integration components: organization, processes, and tools.

The development environment is a production environment for one or several systems development projects as well as for maintenance efforts. It requires the same attention as a similarly sized end-user execution environment.

The purpose of the development environment is to support the tasks involved in the analysis, design, construction, and maintenance of business systems, as well as the associated management processes. The environment should adequately support all the development tasks, not just the code/compile/test/debug cycle. Given this, a comprehensive framework for understanding the requirements of the development environment should be used.

Another reason for the comprehensive framework is that it is important to get the development environment right the first time. Changing the development environment when construction is fully staffed entails serious disruptions and expensive loss of productivity.

Experience has shown that within the same medium- to large-size project, with the same people, moving from a poor to a good development environment, productivity is improved by a factor of ten for many tasks. The improvements come in two categories:

The elimination of redundant and non value-added tasks

The streamlining of useful tasks

While it seems intuitive that most tasks can be streamlined, the following list gives a few examples of redundant tasks that must be eliminated:

Analysis to determine how to merge the uncoordinated changes applied by two programmers to the same module Re-entry of the source code and retesting of a module, which was accidentally deleted Recurring discussions about "what a design packet should contain" or "what constitutes good programming style in a particular context"

Repeated design, coding, testing, and maintenance of very similar logic (for example, error handling, date conversion and manipulation, main structure of a module)

Searching for the manuals of a particular productivity tool to find information

Remigration to system test of a cycle, because the impact analysis for a change request was incomplete Requesting support from another team (for example, environment support, information management) and waiting unnecessarily for a response On a smaller project, these problems can be solved using a brute force approach. This becomes very expensive as the project grows, and finally impossible. A well-designed development environment becomes important as the project team reaches 20–30 people and is absolutely critical with a project size of more than 50 people. The investment required to design, set up, and tune a comprehensive, good development and maintenance environment is typically several hundred development days. Numbers between 400 and 800 days are commonly seen, depending on the platforms, target environment complexity, amount of reuse, and size of the system being developed and maintained.

Development Organization Framework

Figure 9:
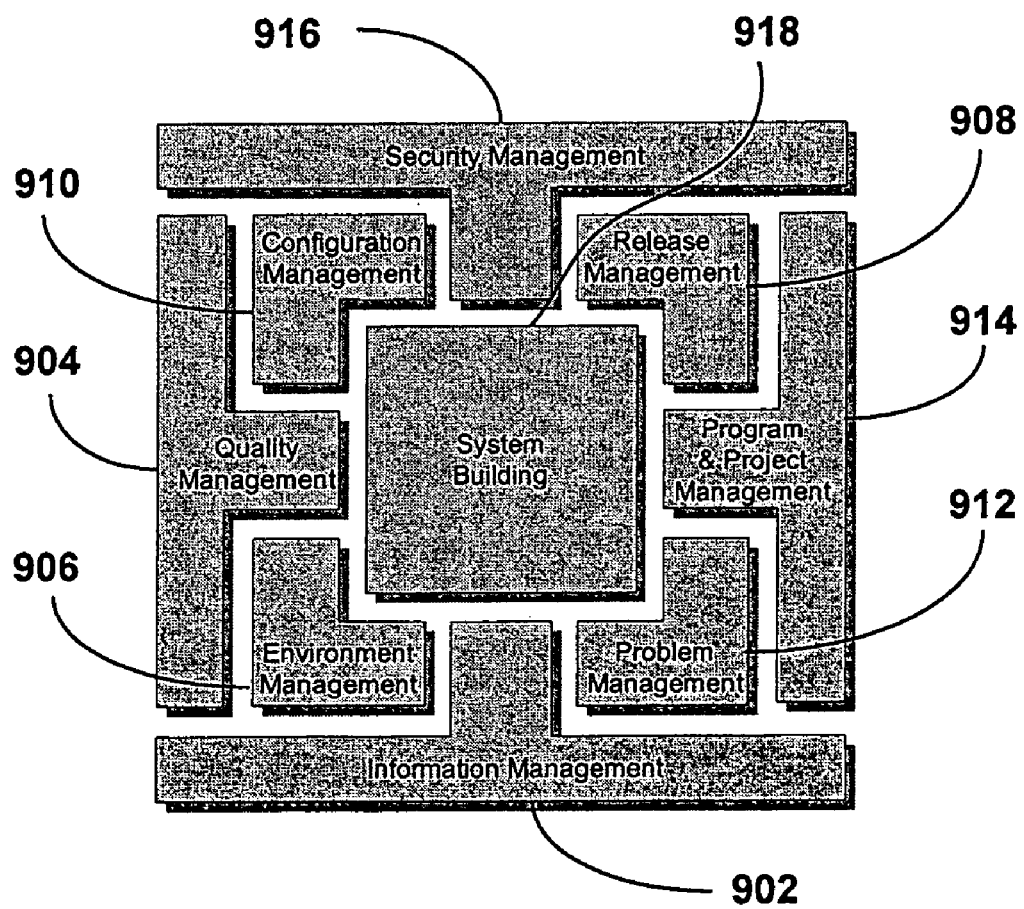
FIG. 9 is an illustration showing a Development Organization Framework in accordance with one embodiment of the present invention.

FIG. 9 is an illustration showing a Development Organization Framework in accordance with one embodiment of the present invention. When designing a business application, it is crucial to keep in mind the organization that will use the system. The same is true of the development environment. The development organization's size, structure, experience, and maturity should strongly influence the choice of tools and the way the tools are integrated. If this link is not understood, the benefit of tool support will be minimal in many areas, and may significantly reduce productivity.

In the same way, when a new business capability is introduced, it is crucial to keep in mind the needs for training and organizational change that which may accompany the technical change. This is also true of the development environment. When a new development environment is put in place, the developers need to learn not only how each individual tool works (for example, how to use the compiler), but also how the tools work together to support the organization as it performs well defined processes.

The Business Integration Methodology (BIM) provides valuable information on organizational issues.

Relying on the Business Integration Methodology and its project organization guidelines (0940—Organize Project Resource Task Package), the following should be prepared:

A list of responsibilities covering both responsibilities for end products and those for on-going processes A Responsibility, Accountability, and Authority profiles deliverable (RAA) for each role in the Development team, making sure that all the responsibilities listed earlier are covered The RAA profiles deliverable consists of statements about the responsibilities, accountability, and authority of each of the positions in the development organization. These statements define the role of each position in terms of:

Responsibility—What objectives the position is expected to accomplish

Accountability—How and by whom the performance will be measured

Authority—The position's decision-making capabilities and limits

In accordance with the IDEA Model, the following management teams with responsibilities for the key management functions are defined as:

The Information Management team 902
The Quality team 904
The Environment Management team 906
The Release Management team 908
The Configuration Management team 910
The Problem Management team 912
The Program and Project Management teams 914
The Security Management team 916

Together, these teams support the efforts of the System Building team, which is charged with the analysis, design, build, and test of the system to be developed. These teams represent real roles, and on a given program the same people may play different roles.

Security Management

The evolution of new technologies and expanded access to a virtual world has increased the security risk of conducting business. It is therefore essential to recognize the need for a new unit in the organization, specifically dedicated to ensuring that security is handled appropriately. At the Program level, the Security Management unit needs to:

Ensure all security issues are effectively addressed throughout the program (all business and IT processes).

Act as facilitator and approving body for all new and existing initiatives that contain security components.

Own responsibility for the organization and facilitation of working groups that would address security issues.

Be responsible for development and maintenance of the Security Plan.

Figure 10:
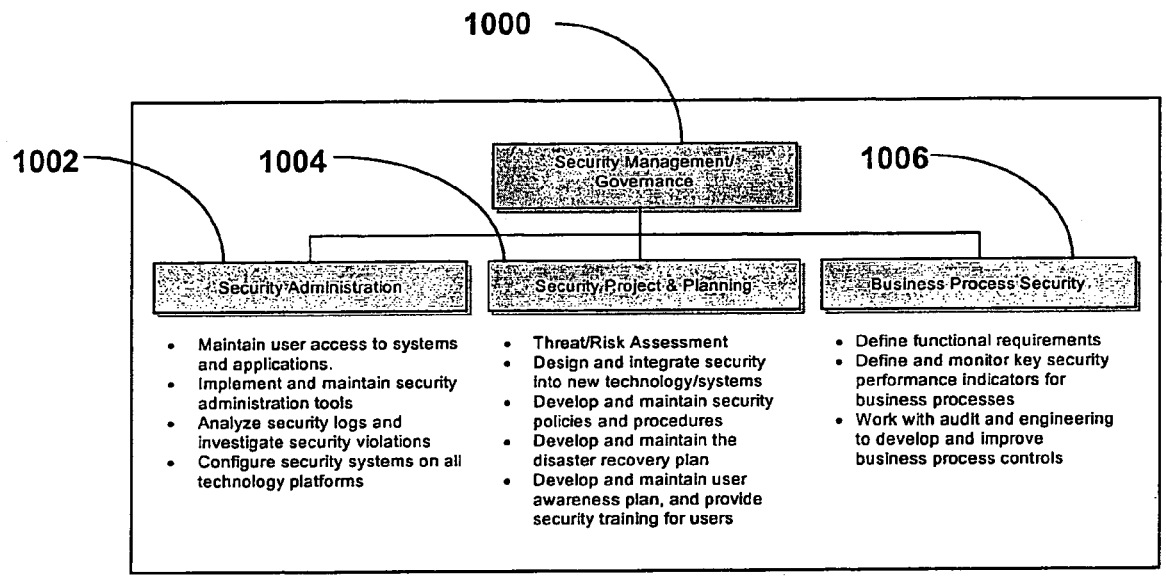
FIG. 10 is an illustration showing a security organization functional according to one embodiment of the present invention.

FIG. 10 is an illustration showing a security organization according to one embodiment of the present invention. A Security Management Team may have a security management 1000, under which are an administration team 1002, a projects & planning team 1004, and a business process security team 1006. The size of the Security Management team, and the way in which it is integrated into the development organization depends on the degree to which security is a factor for each specific environment. For example, the security risks associated with an Internet-based online banking system are far greater than those of a fully isolated client/server system, and therefore warrant a larger team with broader responsibilities and greater influence.

Information Management

The Information Management team is responsible for ensuring that the project's knowledge capital and information resources are managed effectively. This includes:

Ensuring integrity
Ensuring accessibility
Ensuring quality and consistency

Information Management encompasses Repository management, but generally has a broader scope than merely the repository contents, because most repositories are not capable of holding all the information resources of a project. It is, for example, common to have key project information reside in a combination of repositories, teamware databases, flat files, and paper documents. It is the Information Management team's responsibility to ensure consistency across all these formats. The responsibilities of the Information Management team therefore cover:

Repository Management
Folder Management
Object Management
Media Content Management
Information and data reuse coordination In addition to managing the information for the System Building team, the Information Management team must also manage the information resources of the other management processes—quality management, environment management, and project management.

In order to delineate the responsibilities of the Information Management team, it is useful to state those areas that are out of scope. The following are not included:

Performance of daily backups—this is handled by the Environment Management team

Database administration—this is part of the Architecture team responsibilities

Performance tuning of the information repositories—this is handled by Environment Management Repository Management The Information Management team is ultimately responsible for the contents of the repository. They need to have an intimate understanding of the repository structure and the rules that govern how different objects should be stored in the repository. Although most of the input to the repository are entered by designers, the Repository Management team must manage this population process. Rather than taking a policing role on the project, they should work as facilitators—helping the designers do things correctly the first time, thereby maintaining the integrity of the repository. Without strong repository management, the benefits of using a repository quickly diminish.

In many situations the Information Management team must make decisions that affect functional areas. To empower the Information Management team, the Application teams should include the Information Management team in relevant design discussions. This facilitates the validation of design outputs.

Folder Management

Folders (or directories) can be very useful in gaining control over the overwhelming amount of information produced on a large project. Their utility greatly increases if they are managed appropriately. This management is based on easy-to-follow, easy-to-enforce standards.

Object Management

The responsibilities involved with object management are very similar to those involved with repository management. However, in order to facilitate and promote reuse, it is recommended to have a librarian whose responsibilities include:

Reviewing designs
Packaging classes and components for reuse
Managing maintenance and upgrades of common components (a strong relationship with Configuration Management team is required)

Media Content Management

The methods of handling media content are somewhat different from those surrounding more traditional development content such as code or documentation, for this reason, a role should be defined that is responsible for the management of all media content.

Quality Management

The Quality team is responsible for defining and implementing the Quality Management Approach, which means defining what Quality means for the Program Leadership, and then implementing the procedures, standards, and tools required to ensure the delivery of a quality program. The Quality Management Approach addresses concepts such as expectation management, quality verification, process management, metrics, and continuous improvement.

Since quality is the result of the interaction of many teams working on multiple processes, the Quality team is responsible for ensuring effective cooperation between teams and good integration of the development processes. The Quality team must therefore forge strong links with all the other project teams.

It is important to note that the Quality team is not only responsible for ensuring the quality of the system building process. The Quality team is also directly involved in ensuring the quality of the other IDEA management processes.

Program & Project Management

The Program Management team is responsible for delivering business capability. In this respect, it is responsible for the System Building and other management teams. In addition, other management responsibilities that do not have a specific team or role defined within IDEA also belong to the Program Management team. These include:

Contingency Management
   Financial Management
   Issue Management (decisions to be made regarding the development of the business capability, not to be confused with problem management)
   Program Performance Reporting
   Resource Management
   Risk Management
   Vendor Management The Project Management team is responsible for producing a deliverable or set of deliverables. As such, it is responsible for:

Planning and control of delivery
   Milestones and schedule
   Resource consumption
   Risk and quality (at deliverable level)

Configuration Management

The Configuration Management team is responsible for defining the approach the program takes to deal with scope, change control, version control, and migration control, and for putting in place the policies, processes, and procedures required to implement this approach.

In other words, the team is responsible for maintaining the integrity of software and critical documents as they evolve through the delivery life cycle from analysis through deployment.

Release Management

Delivering a system on a release-based approach means delivering the system in a series of consecutive releases, increasing or refining functionality progressively. Some of the main drivers to such an approach include:

To release business benefits early
   To mitigate impact on the organization
   To keep the change program up to date
   To optimize processes
   To test proof of concept
   To reduce risk The Release Management team is responsible for:

Planning the capability release design and development effort, based on the capability development approach and timeline.
   Measuring and monitoring progress using established processes to ensure that a capability release is delivered on time, within budget, and that it meets or exceeds expectations.
   Managing project interdependencies to ensure delivery of the capability release.
   Ensuring that resources are used effectively across projects for the release.

As with many other management responsibilities described in IDEA, Release Management is more a role than a function. It is good practice to have as many areas as possible represented in the Release Management team; for example, Design, Construction, Configuration, and Environment Management team members would make up a typical Release Management team, each providing input based on their own perspective.

Environment Management

Just as a business application requires support and system users require service, the development environment requires system operations daily, and developers require ongoing support in order to use the environment effectively (In fact, the complexity and frequency of these operations is often greater than that of the execution environment).

Figure 11:
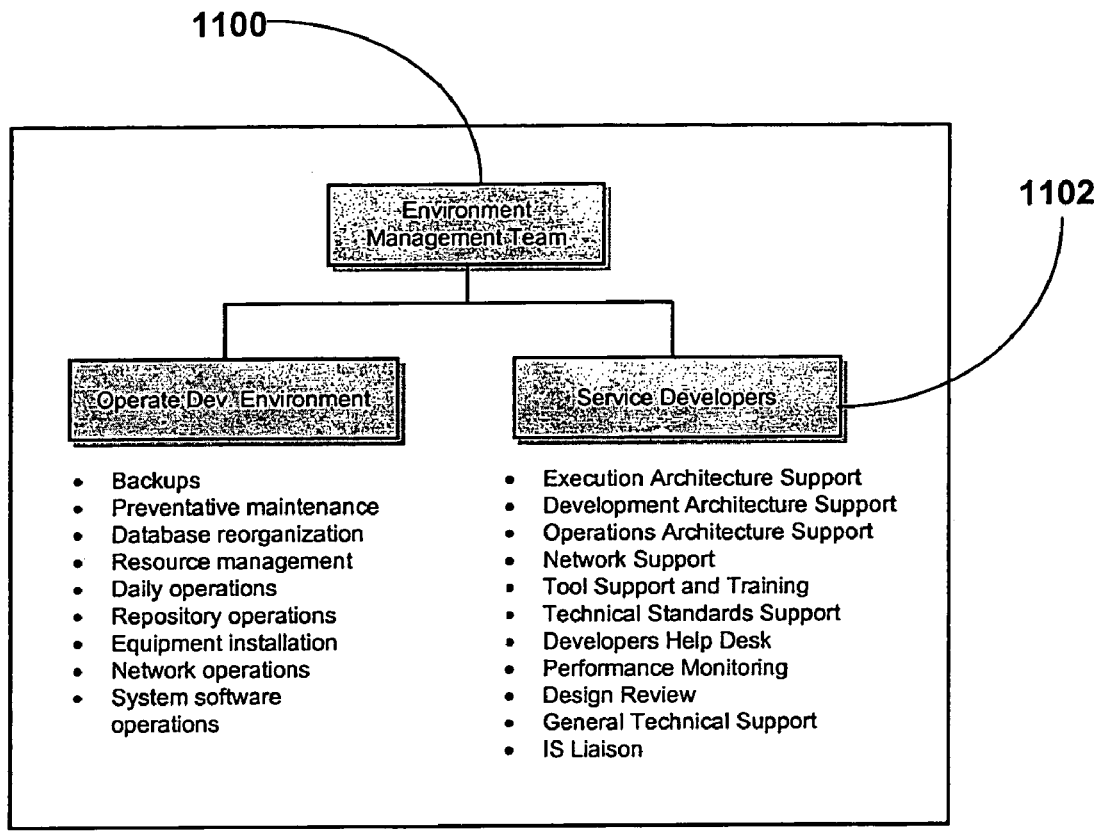
FIG. 11 is an illustration showing the responsibilities of an Environmental Management Team.

To ensure that this area receives the necessary attention, an Environment Management team 1100 should be assigned these tasks. FIG. 11 is an illustration showing the Environmental Management Team responsibilities.

The Service Group 1102 serves as a single point of contact for developers. It interfaces with the Architecture team to provide answers to questions from developers. To avoid adding overhead to the issue resolution process, the support group must be staffed adequately to ensure that all questions are answered. For example, the support group should recruit people from the Technology Infrastructure team at the completion of Technology Infrastructure development.

Problem Management

Problem Management is concerned with the discrepancies that result from the testing process and the management of design problems detected during verification or validation steps throughout the development process.

The Problem Management team is responsible for defining the problem tracking and solution process, and for providing tools and procedures to support the solution process.

System Building

The Business Integration Methodology (BIM) describes System Building under the following activities:

Design application
   Build and test application
   Design technology infrastructure
   Build and test technology infrastructure For this reason, the System Building teams are organized into application and technology Infrastructure.

Application Team

Figure 12:
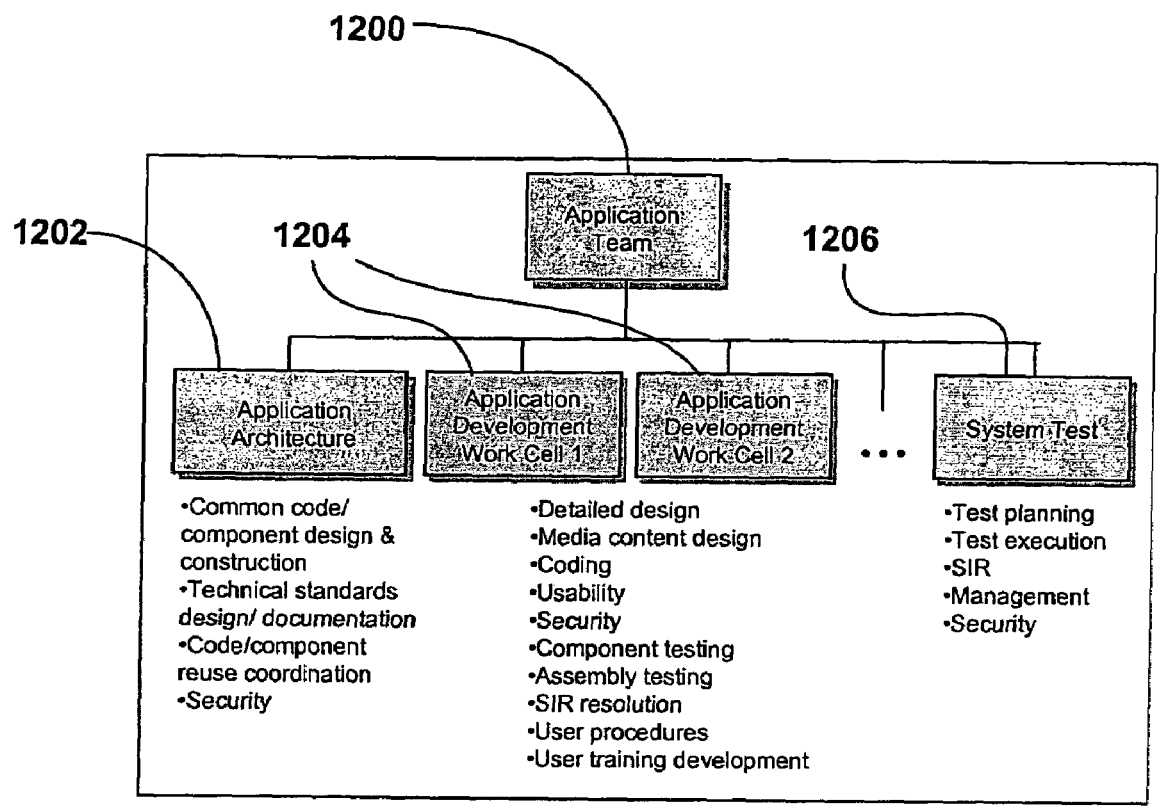
FIG. 12 is an illustration showing the responsibilities of an Application Team structure.

The Application team 1200 consists of three separate sub-teams: Application Architecture 1202, Application Development 1204, and System Test 1206. FIG. 12 is an illustration showing the Application Team structure and responsibilities.

The structure of the Application team evolves as the development process continues—as the development of the application architecture components is completed, the Application Architecture team's roles may change. While the team continues maintaining the application architecture components, some team members may be deployed to the Application Development team. Here their roles can include helping application developers to correctly use the architecture components, providing development support, and performing code reviews, and so forth.

As systems become more user-facing, important new roles are emerging that must be integrated into the Application Development teams:

a) Media Content Design

For any system with a user-facing component, it is extremely important that media and design specialists are involved as team members at an early stage in the design of the system. In systems with simple user interfaces, this helps to ensure usability and consistency. As user interfaces become more complex, the early involvement of design experts not only leads to more creative and attractive user interfaces, but also reduces the risk of further alteration to work at a later stage.

b) Usability

Often coupled with Media Content Design, it is vital that a role for usability is defined within the Application Development teams. This will ensure the usability of the system from the perspective of target user groups.

Technology Infrastructure Team

The technology infrastructure evolves throughout the project and responsibility for managing and evolving the infrastructure must be clearly defined. Therefore, rather than having a single amorphous 'technical team' (responsible for operations, support, architecture evolution, and more), it is important to define a dedicated technology infrastructure team. By allowing the technology infrastructure team to focus on the technology infrastructure, rather than the day to day running of the environment, the project increases the chances that the technology infrastructure will provide good support for the business applications.

In practice, the Technology Infrastructure team is the team that will implement the IDEA framework.

The Technology Infrastructure team is responsible for:
Data design and management
Database administration
Database tuning
Execution architecture design and construction
Development architecture design and construction
Operations architecture design and construction
Network design
Technical standards design and documentation
System software selection
Performance tuning of the final system
Security infrastructure development Note: The responsibilities of the Technology Infrastructure team may overlap with those of the Application Architecture team, and on some projects the two teams are often combined.

Development Processes Framework

A thorough understanding of the development processes is a prerequisite for ensuring that the tools effectively support the organization and the processes they are intended to support.

The Development Process Model

The Development Process Model is a framework that facilitates the analysis of the many concurrent processes of systems development. This analysis helps understand process interaction, which, in turn, affects organizational interaction and defines a need for tools integration.

The Process model is simple—at its core is the system building process, which is surrounded by eight key management processes.

The core activity—systems building, depends strongly on support from the surrounding management processes, which all affect each other:

a) Information Management manages the information that supports the entire project—information that is used both in systems building and in other management processes b) Security Management covers all areas of development security, from coding standards, to security verification.

c) Quality Management pertains to all areas of the development environment d) Program and Project Management must manage all the management processes in addition to managing the systems building process e) Environment Management supports the environment where management processes are performed, and where systems are being built f) Release Management manages the simultaneous development of multiple releases g) Configuration Management, often closely linked with release management covers the version control, migration control and change control of system components such as code and its associated documentation h) Problem Management pertains to the problem tracking and solution process Process Definition For a given project, each of the processes must be defined at a greater level of detail than that which any methodology can achieve. This additional specification consists of a set of procedures and standards that specify how to perform the work and what to produce at each step.

Standards specify what the results should look like. They may include industry standards and more formal (de jure) standards, such as POSIX compliance, but most standards are project specific and determine, for example, how to structure and name system components and where to place system components. Standards make it possible for a large team to exchange information effectively and to work productively together.

Standards should focus on what must be common, and should not become a goal in themselves. Erring on the side of over-standardization stifles productivity. It is, however, often the case that unforeseen events (such as platform demise, tool evolution) will be easier to tackle the more unified the development approach has been used. Unfortunately, there is no substitute for experience when making the detailed decisions on exactly what should be standardized. Factors to take into account must at least include:

Life expectancy of the system under development—the higher the life expectancy, the more standards are warranted Life expectancy of the development organization—the higher the life expectancy, the more standards are justified Attrition—a stable organization can tackle more detailed standards than a volatile one Expected change in the environment—a high rate of change provides greater opportunity to reap the benefits of a standardized approach Procedures specify how to perform a task. They are generally guided by the methodology but provide information at a lower level of detail. They are highly environment-specific, and take into account the organization, the standards, and the tools in the environment. Procedures often specify the techniques to be used. They may specify which tools to use and how to use the tools that support these techniques.

Many processes require individual judgment, and the way to perform these processes cannot be specified in detail. In such cases, it may be valuable to provide guidelines that do not have the mandatory flavor of procedures but rather that of valuable advice.

While it is easy to generate zeal to set up standards and procedures at the beginning of a project, it can sometimes be more difficult to ensure that these are enforced throughout the project. Two considerations are useful. Firstly, standards must be easy to follow. It should be easier to follow the standard than doing things any other way. This is generally achieved by supplying the training, tools, and support needed to facilitate a given work style. For example, developing and distributing application program shells, which respect the architecture and standards, facilitates programming and contributes to ensuring broad standards compliance. Secondly, the responsibility for enforcing standards must be clearly identified and assigned. Standards enforcement must take place as a natural part of the process and at well-defined check points before work flows to the next task, or (even more importantly) to the next group or team.

A very useful way of complementing the specification of procedures is to provide samples. Samples can sometimes convey a message much faster than pages of explanatory prose. Sample programs are generally very useful. Other samples may include logs, which demonstrate interaction with tools, a sample change request, or a sample request for technical support. Samples can sometimes be created efficiently by taking screen dumps. This can be much faster than specifying what the screen should look like in theory.

Samples and standards must be high quality—any quality breach will be multiplied when developers start using them. It is therefore imperative that samples and standards not be created in a vacuum but be based on concrete experience with the project's development environment. Some pilot development work often proves extremely useful when fine tuning the standards.

When documenting the process, it is useful to develop an approach and process description for each project segment and for each high-level process. This document summarizes the support available for that segment or process. It refers to all the standards, procedures, guidelines, and examples relevant to a collection of tasks. Such a summary document makes it easier for developers to navigate the standards and hence to follow them.

Process Integration

To ensure that the project team works effectively together, numerous processes must be integrated. A simple example is provided by the required integration between design and construction. A more subtle one is the integration of product quality inspection and the continuous improvement process.

As process integration frequently involves several teams, it is crucial to understand the interfaces between processes and teams to ensure good hand-offs. This understanding must have a direct impact on tools integration, so that integrated processes are supported by integrated tools. Tools that support multiple processes performed by the same individual must, at a minimum, be integrated at the user interface level and should ideally be integrated at the process level. Tools that support processes performed by different individuals may only have to be integrated at the data level.

See Tools—Process Management for more details.

Security Management

Processes must be put into place in order to ensure security is properly designed and built into the system that is being developed, including:

Definition of security requirements based on business risk

Development of security standards, guidelines and procedures

Implementation of security controls

Security validation

Security Requirement Definition

Security requirements are the outcome of the security Risk Assessment. This is the process of identifying business risks, identifying system vulnerabilities or weaknesses that can impact those risks, and recommending mechanisms to control the vulnerabilities. Specific confidentiality, integrity and availability requirements for the new system and the development environment are defined through this process.

Security Standards, Guidelines and Procedures

Security standards, guidelines and procedures provide security direction to the implementation. They will help define how the security requirements developed through the Risk Assessment must be addressed in all areas of the development environment. They will include security standards for the development environment infrastructure, procedures for the development processes, standards for the design of the security architecture and security guidelines for programming. It is especially important to ensure the security of the development environment because if these systems are broken into and back doors are introduced, it may lead to later compromise of the production system. It will be the responsibility of all developers that these security controls are implemented and adhered to throughout the development process.

Security Validation

In order to ensure the security of the system, periodical security audits should be arranged, in order to verify that the processes and architecture and application components that are being developed conform to security proven practices. This may be done by an external body specializing in security (such as Global TIS-Security) in the form of interviews, architecture and code reviews, and automated tool assessment.

Information Management (902)

A vast amount of information is generated within the development environment, which needs to be carefully managed (for example, design documentation, application code, media content, test plans and test data). Information Management generally involves Repository Management, Folder Management and, where applicable, Object Management and Media Content Management.

Since a number of teams rely on the service provided by the information management team, it is important that the level of service to be provided be chosen carefully, documented, and communicated. The arrangement should take the form of a Service Level Agreement (SLA). Such an SLA typically defines how quickly a new data element is created and how repository changes are communicated. More generally it defines the division of responsibilities between the information management team and the other project teams at a detailed level.

Repository Management (802)

Repository Management includes activities such as:
- Monitoring and controlling update activities in the repository
- Receiving and validating data element change requests
- Creating and modifying data elements
- Enforcing project standards regarding repository objects
- Validating the contents of the repository to avoid redundancy and inconsistencies
- Ensuring accuracy of the repository contents so that the repository reflects the applications being developed
- Importing and exporting from one repository to another
- Maintenance of the information model (or metamodel), which describes how data is represented within the repository As many repositories do not provide sufficient versioning functionality, it is common to have more than one repository on large projects. Typically, there may be one repository for development, one for system test, and one for production. This allows better control, but also requires significant resources to move repository objects from the development environment to the system test environment. By merging the development and system test repositories, the medium-sized project has a potential for productivity gains. If these gains are to be realized, great care must be taken when making corrections during system test. As a common repository is shared, any error analysis involving repository objects must take into account the possibility that these objects could have changed since the previous migration to system test. This situation can be managed by meticulously maintaining a comprehensive change log.

Another reason for maintaining several copies of the repository is the existence of concurrent projects focusing on different releases. If this is the case, it may be beneficial to maintain delta repositories, which document those components that have been modified. This requires strict repository management but the reward can be significant. It allows the merging of several releases, which have implemented complementary functionality, but which have modified a few shared components.

A single development environment may have to deal with multiple repositories:
- For functional reasons, one repository might be integrated with an upper-case design tool and the other with a lower-case generation tool
- In a multi-site environment, repositories may be distributed over different locations. In order to keep these repositories synchronized, well defined development processes must be implemented.

Repository Management can be divided into the following areas:
- Security
- Maintenance
- Validation and mass change
- Analysis, reporting, and querying Security Restricted access to various repository object types is necessary to ensure high quality repository content, because developers sometimes take shortcuts and make unauthorized changes to meet their deadlines. When standards have been set, a good way to enforce them is to restrict personnel through the use of locking mechanisms. Access to repository object types will change throughout the project.

The data elements should usually be controlled by the Repository Management team, because they are the basic building blocks of the system and have broad reuse. Poorly defined data elements can cause inconsistency, redundancy, and generation errors. Data elements should therefore be locked at least by the time construction starts, and possibly earlier, depending on the discipline of the team. Project members must be allowed to browse the data elements, but only the Repository Management team should be allowed to modify or unlock data elements. In some repositories, it is difficult to restrict the creation of repository objects. If this is the case, it may be acceptable to let designers create data elements if these are reviewed and locked at the end of each day. Increased control can be obtained by having designers submit requests for new data elements to the repository administrator. This allows the repository manager to evaluate whether the new data element is justified, or whether an existing one should be used.

Repository Maintenance a) Creating and Maintaining Data Elements

Requests for data element changes can be forwarded using a database or paper-based system. Based on functional and technical knowledge, the repository administrator evaluates the requests and may involve other teams to make appropriate decisions. The database used to request data element changes during design and programming should be separate from the project's change request database. This will simplify and speed up the change process. When data elements have to be changed during system test, however, the impact can be much greater, and the regular change request database should be used.

Whenever a data element is changed, impact analysis must be performed to understand the side-effects. Where-used reports are useful to determine these side-effects. The repository manager must be able to obtain the list of direct references and the list of all components affected indirectly (transitive closure). In the latter case, a message based on a record containing a group, which makes reference to a changed data element is considered to be indirectly affected by the change.

When adding a data element, no functional equivalent must exist, because redundancy creates difficulties for impact analysis and future maintenance.

b) Creating and Maintaining Other Repository Objects

The objects related to dialog definitions, reports, messages, and so forth, are usually maintained by the designers and programmers. When the dialogs and report programs are tested, approved, and ready to be promoted to the system test environment, the related objects must be locked. This is the responsibility of the Repository Management team.

Repository Validation and Mass Changes

Keeping thousands of data elements consistent and in compliance with project standards requires a sustained effort. This daily effort is crucial to avoid a massive clean-up, which would be necessary if the repository manager ever lost control of the repository.

Detailed, project-specific standards should exist for defining repository objects. These standards can form the basis for a repository validation program, which can run through the entire repository and report on detected deviations from standards. In some cases, this program can also enforce the standard.

Mass changes to the repository can be performed when the validation reports show the occurrence of many standards violations that follow a common pattern. This may occur in cases where:
- Project standards have been incomplete
- Project standards have changed
- Repository management has been poor New objects have been imported from another repository Analysis, Reports, and Queries Certain reports should be run daily, such as the list of new data elements or modified data elements. These reports can serve as an audit trail of changes and can be used to communicate changes to the entire team. Procedures should specify which reports are run daily and what their distribution should be.

The Repository Management team performs certain analyses repeatedly. Standard analyses such as impact analyses should be specified in detail to facilitate staffing flexibility.

When supporting specific kinds of repository analysis, the Repository Management team can provide custom reports or ad hoc queries that satisfy particular needs.

Folder Management (804)

It is important to set up and communicate a detailed folder structure with specified access rights from the beginning. Contents of folders must be checked regularly to ensure that folders contain what they are supposed to.

Two main strategies exist.

Folders can be organized by type of component so that one folder contains all the include files, one folder contains the source modules, one folder contains executables, and so on.

Folders can also be organized functionally so that all the common components reside in one folder and each application area stores its components in its own folder.

Choosing the strategy depends on how components are named, on the number of components, and on the tools used. If naming standards make it easy to identify the component type (for example, by using suffixes), organizing them by functional area is generally useful and straightforward to administer. Some tools assume that closely linked files (for example, source and object modules) reside in the same folder.

Another important distinction is the one between work in progress and completed documents that have been approved. This distinction can be supported by a folder structure with carefully chosen access rights.

This distinction makes it easy to retrieve a consistent copy of project documentation for someone who is new to the project.

While scratch folders may be useful in certain contexts, the proliferation of miscellaneous folders with cryptic names can make it very difficult to navigate the information. Some useful guidelines include:

Keep the folder structure under central control.

Within personal folders, allow users to create any folder structure.

Clearly assign ownership for the contents of each folder.

Document each folder, either in a central location, or in the form of a readme type file within the folder itself. The high-level documentation should include the purpose of the folder and the kinds of contents it should hold.

Perform regular clean-up, by backing up redundant or misplaced files and then removing them.

Media Content Management (806)

The unique nature of media content means that it cannot be treated in the same way as 'standard' formats, such as source code or design documentation. The major differentiating factors are its sheer volume (media files can range from a Kilobyte to multiple Gigabytes), and the complexity of its associated formats (i.e. it is not easy to 'look into' a media file and understand its contents). For this reason, some of the processes that support multimedia content management must be handled differently. The three major processes that are required to support media content management are:

Storage management

Metadata management

Version control

Storage Management

Storage management concerns the methods of storing and retrieving media content. The cost of data storage may be decreasing, but it is still the case that for large volumes of media it is often uneconomical to store everything on-line. For this reason, processes must be implemented to manage where data should be stored, and how it may be transitioned from one location to another. There are three ways to store data:

On-line (Instant access, for example, hard disk)

Near-line (delayed access, for example, CD-ROM jukebox)

Off-line (manual access, for example, CDs or tapes on shelves)

When deciding on where media content should be stored, there is always a trade-off between accessibility and cost (on-line storage being the most accessible and most expensive, and off-line the cheapest but least accessible). The decision of which method to use for which data may depend on a combination of its type, volume, version (i.e. latest or historic) and accessibility requirements.

Metadata Management

Data about the media that is being stored is an important commodity that must be managed. As the volume of media content grows, it is vital to be able to understand characteristics of the media, in order to be able to manage it correctly. Examples of metadata include:

Media type (for example, MPEG video, JPEG image)

Media settings (for example, sample rate, resolution, compression attributes)

Usage details (which module uses the content)

Media source (for example, Source, author, creation date)

Legal information (for example, whether the media is copyrighted)

Version Control

As with standard development code, when media content is created and edited, a revision history of changes should be retained. This way, if it is necessary to revert to an original piece of media content, it is not necessary to go all the way back to the original source (which in the case of finding an image in a CD-ROM library containing 10,000 images, for example, could be a difficult task). In practice, this may mean storing the original and final copies of media (especially where volume is an issue). For this reason, a process for managing multiple versions of media content must be put into place.

The more advanced media content management tools may provide much of the functionality required to support these processes, but where this is not the case, the processes must be implemented manually.

c) Legal Issue Management

When dealing with media, it is often the case that content may be subject to copyright laws. It is important that the legal implications surrounding all content in the system is understood, and where necessary, royalties paid to the appropriate parties.

Object Management (808)

Object Management processes are very similar to those involved with Repository Management. However, they should promote reuse through specific processes:
   Design review
   Classes and components packaging for reuse
   Common components maintenance and upgrade Quality Management (904)

Quality Management is described at length in the Business Integration Methodology (BIM).

The Quality Management processes are covered by the following tasks:
   0623—Define Quality Management Approach
   0732—Implement Quality Management Approach The objective of these tasks is to ensure that, early in the life of a program, program leadership explicitly defines what quality means for the program. This results in the production of the quality plan. Then the infrastructure and processes are put in place to ensure delivery of a quality program.

The Quality Management Approach defines the following processes:
   Expectation Management
   Quality Verification
   Process Management
   Metrics
   Continuous Improvement
   Rewards and Recognition
   Training and Orientation Focus here is on those processes that have a direct impact on IDEA and its components (that is, Systems Building and the management processes).

Expectation Management Process

Expectations can be thought of as quality objectives expressed in measurable terms such as:
   Functionality
   Reliability
   Usability
   Efficiency
   Maintainability
   Portability
   Security Quality Verification Process The targets for quality verification should be defined. Processes and deliverables are key candidates.

In development terms, the V-model is the preferred method by which the quality verification process is managed. The V-model ensures that deliverables are verified, validated, and tested. It is based on the concept of stage containment (enforcing for a given deliverable the identification of the problems before it goes to the next stage) and entry and exit criteria (describes conditions in which a deliverable passes from one stage to another).

The quality verification process owner may not be responsible for executing the V-model, but is responsible for making sure that the V-model is in place and complied with.

Metrics Process (810)

To fine-tune the development process, the important quality attributes must be measured. Sample metrics include:
   Development environment availability
   Time needed for a new user to learn to use a function of the development environment
   User error rate per function
   User satisfaction per function
   Code complexity
   Code structure
   Productivity
   Average number of defects per design packet at the moment construction starts
   Average number of defects per program at the time of its first migration to system test Once the key metrics are agreed upon, procedures must be put in place to:
   Perform the measurements (these should flow from the development processes in a natural way)
   Compare results with the goals documented in the quality plan
   Analyze deviations, with key focus on the process that caused the deviation
   Adjust the processes so that similar deviations do not occur in the future Continuous Improvement Process (812)

The first stage of the Continuous Improvement Process (CIP) is to capture continuous improvement opportunities. These may include:
   Gaps identified by metrics
   Analysis of program performance-internal quality verification results
   Process reviews
   Capability Maturity Model (CMM) assessments (See Standards and Procedures)
   Suggestions made by program team members; for example, through a suggestion box The CIP then plans and manages improvement related activities such as:
   Define explicit criteria for assigning priority
   Consider raising the priority of low-priority opportunities that can be completed quickly
   Maintain a mix of high-priority and sure successes to ensure the continued momentum
   of the Continuous Improvement program
   Define the opportunity selection process
   Identify the resource allocation process
   Define the scheduling process
   Identify how the effort will be monitored
   Identify the procedure for communicating results to the organization
   Establish a continuous improvement organization to support the process
   Prioritize and classify opportunities
   Select projects
   Allocate resources and scheduling
   Monitor effort
   Support a standard process improvement process across the project While maintaining quality at a program level, the Quality Management team must liaise with each of the organizational units within the development environment in order to monitor the quality management processes within these units.

Standards and Procedures

The Capability Maturity Model (CMM) for Software describes the software engineering and management practices that characterize organizations as they mature their processes for developing and maintaining software.

The CMM provides a software organization with guidance on how to gain control over their processes for developing and maintaining software and how to evolve toward a culture of software engineering and management excellence. The model defines five levels of software process maturity as well as how to move from one level to the level above.

For more details, refer to Consistently Delivering Value: The CMM—How to Help Your Project Measure Up.

The V-model is a framework that promotes stage containment by organizing the verification, validation, and testing in and across all the methodology elements throughout the delivery phase of the Business Integration Methodology.

For more details, please refer to the V-model overview job-aid in the Business Integration Methodology.

The IMPROVE Job Aid (provided with the BIM Guide) describes the process for solving problems or improving a process. In this Job Aid, you will find an introduction to the five step process your team can use to solve both simple and complex problems. The Quality Action Team (QAT) is responsible for applying IMPROVE to improve a process or solve a problem.

Program and Project Management (914)

Program Management

Program Management focuses on the continuous oversight needed to support the delivery of business capability through multiple projects and releases. Appropriate disciplines, techniques, and tools are used to plan and organize the work, and to manage the incremental delivery of the new business capability.

Program Management consists of three major activities, each split into a number of task packages.

a) Plan Program
- 0610—Understand Program Expectations
- 0620—Plan Management Processes
- 0640—Develop Program Master Plan
- 0650—Design Initial Teamwork Environment*
- 0670—Plan Delivery
- 0680—Create Program Plan b) Mobilize Program
- 0710—Obtain and Deploy Resources
- 0730—Implement Management Processes
- 0750—Establish Program Management Office
- 0770—Implement Initial Teamwork Environment*
- 0790—Establish Orientation and Training c) Manage and Improve Program
- 0810—Direct Program
- 0820—Execute Management Processes
- 0830—Analyze Program Performance
- 0840—Plan and Implement Program Improvements
- 0850—Operate Program Management Office
- 0860—Authorize Build and Test
- 0870—Authorize Deployment
- 0880—Operate Team Work Environment*
- 0890—Conduct Program Close-Out

*The Team Work environment, in the domain of the development environment, includes those parts of the development environment which are consistent across the entire program (e.g. Collaborative tools)

Project Management

Project Management focuses on providing specific deliverables through balanced management of scope, quality, effort, risk, and schedule. Project Management processes follow a cycle of planning the project's execution, organizing its resources, and controlling its work. The Project Management team oversees all other teams within the development environment.

Project Management comprises a single activity containing a number of task packages.

a) Plan and Manage Project
- 0920—Plan Project Execution
- 0940—Organize Project Resources
- 0960—Control Project Work
- 0990—Complete Project Configuration Management (910)

Configuration Management is not only the management of the components in a given environment to ensure that they collectively satisfy given requirements, but it is the management of the environment itself. The environment consists not only of system components, but also of the maintenance of these components and the hardware, software, processes, procedures, standards, and policies that govern the environment.

Configuration Management in systems building consists of four major interdependencies:
Packaging
Version control 814
Migration control 816
Change control 818

Standards and Procedures a) Packaging Plan

Packaging is the combination of systems software and application component configurations (source code, executable modules, DDL and scripts, HTML) together with their respective documentation. It may also include the test-data, test scripts, and other components that must be aligned with a given version of the configuration. Packaging allows the grouping of components into deliverable packets of application software that can be developed, tested, and eventually delivered to the production environment. Packaging defines the underlying architecture that drives version, change, and migration control. Each of these control processes defines how changes to configuration packages are versioned and migrated to the various development and test phases in the systems development life cycle.

A sample packaging strategy would take into consideration some of the following factors in determining a unique method to handle a given configuration packet in terms of version, change, and migration control:

Base package type—identifies the various types of application components that are developed during systems building such as executables, JCL, HTML scripts, and Java applets.

Package release type—identifies the types of commonality that components can have. There are usually four basic types of components that are developed during systems building:

Technology architecture packages—these packages are developed by the Technology Architecture team and are used by all other projects in a program Program-wide packages—these packages are developed by the Application Development teams but are used by other projects in the program. They are common components that are not owned by the Technology Architecture team Application common packages—these packages are developed by the Application Development team and are used internally on the project by application developers Application packages—these packages are the most rudimentary of all packages developed. They consist of basic application components developed by application developer Package platform type—identifies the eventual delivery platform of the package. Identifying this early on in development and encapsulating this information within the package definition, allows developers to envisage the production environment at an early stage during the systems development life cycle.

Given these three basic package definitions, a configuration management cube can be defined, which uniquely identifies version, change, and migration control characteristics of a given package. The cube can be used to implement a table-driven configuration management control system for all software developed on the program. The configuration control system consists of version and migration control. Therefore, the cube defines all processes associated with version control and migration of a package.

b) Version Control (814)

Version control and compatibility are key considerations when managing these packages. Note that version control not only applies to software components, but also to all components of a given package, including test scripts, test data, and design documentation. It is also of great importance to keep track of which version is in which environment. If incompatibilities are discovered, it must always be possible to "roll back" to a previous consistent state, that is, to revert to an earlier version of one or more components. It must be possible to define releases of a configuration—a list of version numbers, one for each component of the package which together form a consistent configuration. The smallest unit that can be version controlled should be the package as defined in the packaging plan. This ensures that the lowest common denominator in all version control activities is managed at the package level.

c) Migration Control (816)

Figure 13:
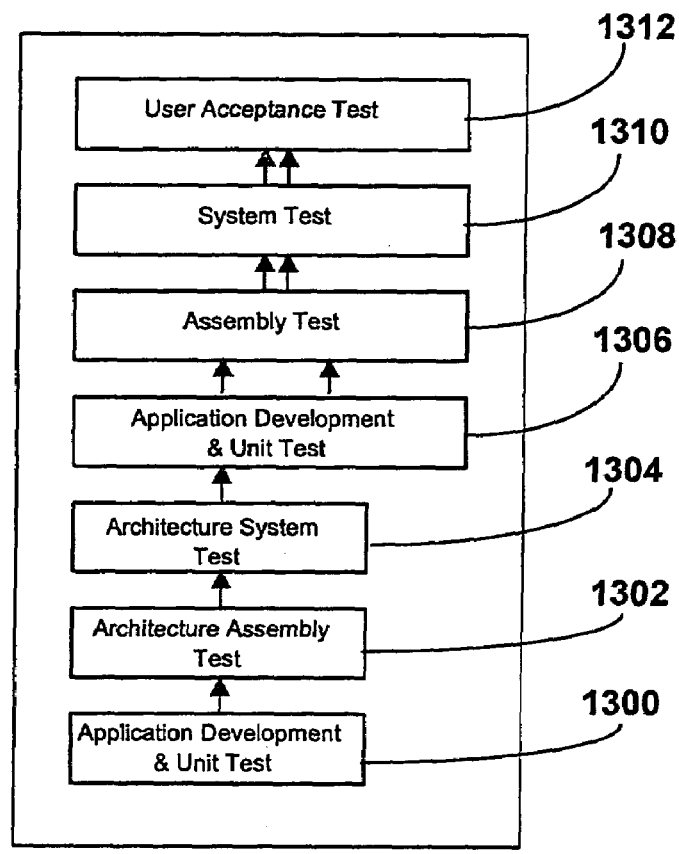
FIG. 13 is an illustration showing a model migration plan in accordance with one embodiment of the present invention.

A systems building environment can have many development and test stages. On a large project these may include:

Development and unit test
Assembly test
System test
Integration test
User acceptance test Migration of packages or consistent configurations from one stage to another is a central part of Configuration Management. The key to successful migration is the knowledge of what constitutes each stage. Examples of migration include:

Migration from development and unit test to system test
Migration from user acceptance test to production
Migration of development tools from the Technology Architecture team to the developers on the project
Migration of architecture components from the Technology Architecture team to the developers on the project Stages and their constituents exist as a result of certain user and technical requirements. The technical requirements are derived from the user requirements. It is crucial to develop a migration plan that maps out the progression on configuration packages throughout the systems development life cycle. FIG. 13 is an illustration showing a model migration plan in accordance with one embodiment of the present invention.

The FIG. 13 model allows the development and testing of architecture components independent of application components. The Technology Architecture team can develop 1300, assembly test 1302, and system test 1304 their components before delivering them to the development environment for the application developers.

This ensures that the architecture is thoroughly tested before being used by the Application teams. The model also illustrates the progression of architecture and application components through the systems development life cycle. The application developers can then develop 1306, assembly test 1308, and system test 1310 their components before user acceptance tests 1312. The model is a temporal one and thus suggests that architecture must be present at a given stage before the introduction of application components.

The version control plan must align with the migration control plan. The version control plan defines the points where version control activities will take place. In the above example, version control will take place at the development stages, architecture development and unit test, and application development and unit test.

Migration control defines how these version control configuration packages will be migrated successfully from one stage to the next until the package is eventually released to the production environment.

d) Change Control (818)

Change requests as a consequence of changing requirements and changes requested due to nonconformities (or defects), either in the application software, or in the system software must be analyzed, authorized, scheduled, staffed, and tracked in a defined way. What, why, when, and who made a change must be tracked from the point of analysis to the reintroduction of the defective or changed component at the appropriate stage. Change control therefore governs what software component is changed, version controlled, and when it is remigrated to a given development stage. It is important to link the general change request with the requests produced during formal testing phases. This makes the processes clearer.

Configuration Management becomes more complex in a component-based development environment as the system is broken down to a greater level of granularity.

Release Management (908)

Release Management involves coordinating activities that contribute to a release (for example, cross-project management) and the coordination of products that contribute to a release (such as architecture, integration, and packaging). It is concerned with managing a single release rather than cross-release management.

The Release Management approach documents critical decisions regarding the management, tracking, and integrity of all components and configurations within a given release. The Release Management approach must be closely coordinated with the definition of the Configuration Management approach and the Problem Management approach. Release Management involves two main components:

The coordination of activities that contribute to a release
The coordination of products that contribute to a release The coordination of products that contribute to a release is the maintenance of a bill of materials for a release. It is an inventory of all software and hardware components that are related to a given release. The development environment is directly affected by the Release Management strategy. The way a program decides to plan releases affects the complexity of the development environment. It should be noted that delivering a system in a series of releases significantly increases the effort.

Standards and Procedures

Figure 14:
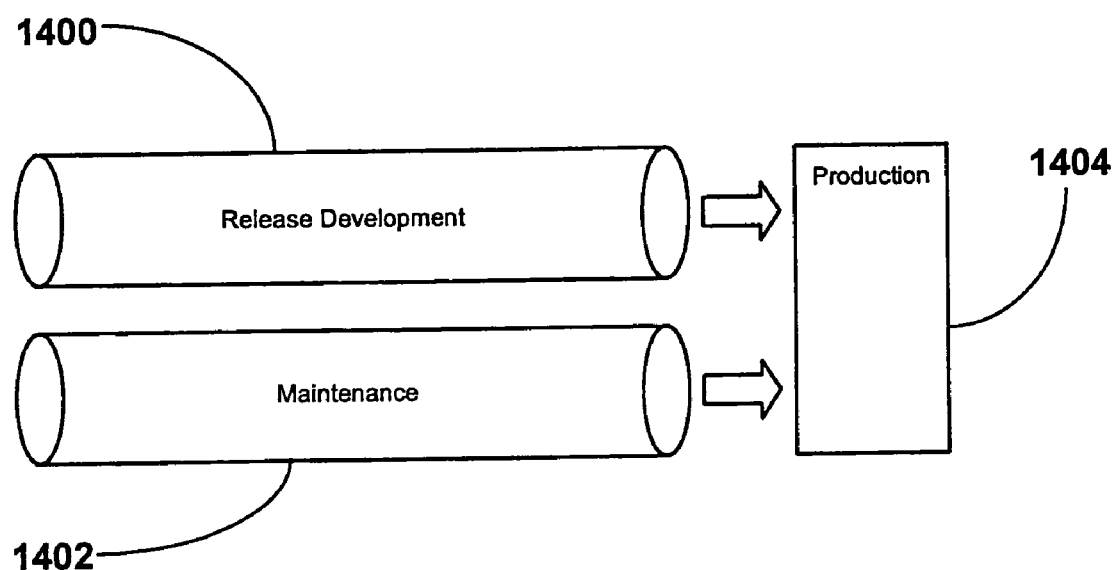
FIG. 14 is an illustration showing a single release capability development pipeline in accordance with one embodiment of the present invention.

If the release plan dictates that there will be parallel development of two releases of software, the development environment and configuration management must be able to support the release plan. In the most general development case, a program can have a single release capability mechanism 1400 but must simultaneously perform maintenance activities 1402 for components that are in production 1404. There must be an ability for the program to design, build, and test the applications for production. FIG. 14 is an illustration showing a single release capability development pipeline in accordance with one embodiment of the present invention.

The ability to perform all development stages for a given release can be defined as a development pipeline. The pipeline consists of all development and testing stages necessary to release the software to production.

The pipeline strategy of a program depends directly on the release strategy. A program is potentially developed on three different timelines:

Short term 1500—production bug fixes

Middle term 1502—production service packs

Long term 1504—new releases of software

To support this release plan, the development environment must be separated into pipelines that are replicas of a single migration path to production 1404. A pipeline consists of all the necessary development and testing stages required to deliver a piece of software to production. Therefore, because of simultaneous development and testing of three code bases, there needs to be three development and testing pipelines that deliver software to production.

Figure 15:
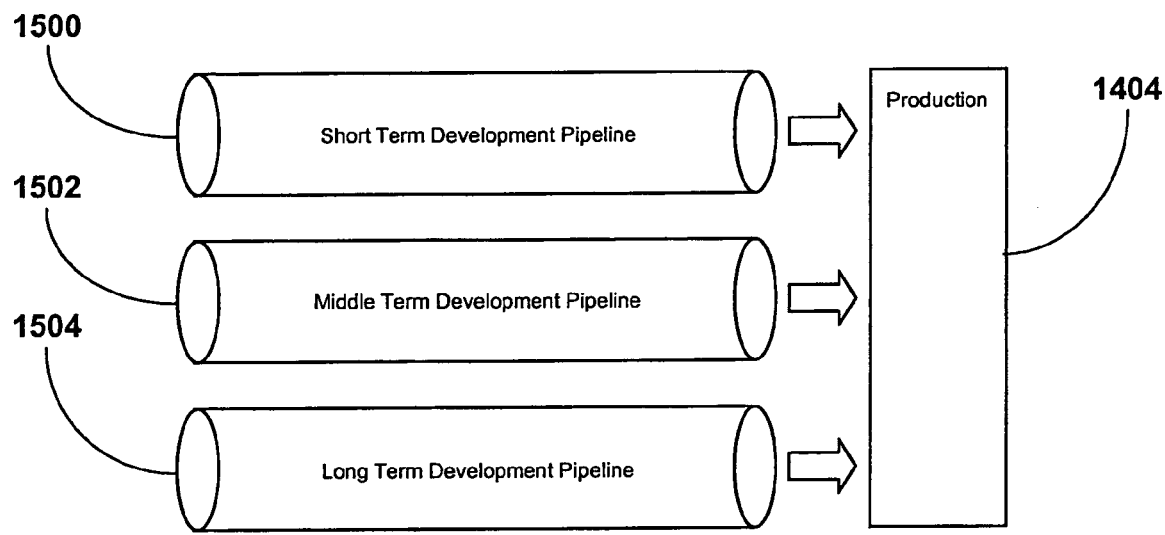
FIG. 15 is an illustration showing a multiple release capability development pipeline in accordance with one embodiment of the present invention.

The pipelines must be capable of allowing the developer to design, build, and test applications as well as architecture components. FIG. 15 is an illustration showing a multiple release capability development pipeline in accordance with one embodiment of the present invention.

Figure 16:
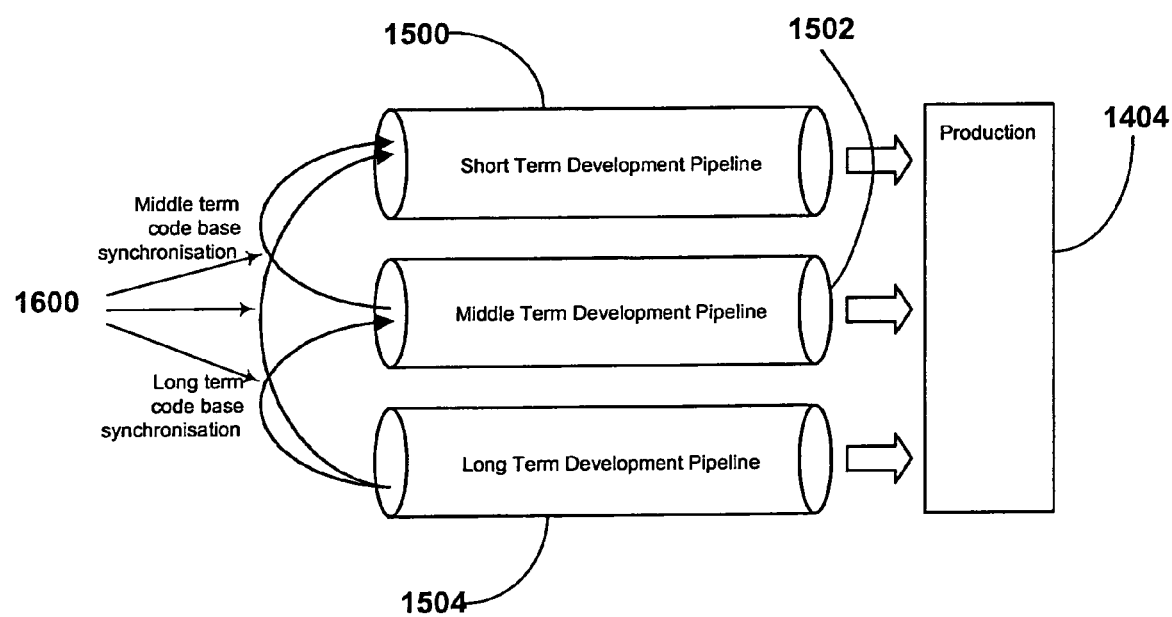
FIG. 16 is an illustration showing a multiple release capability development pipeline with code base synchronization among three pipelines.

As can be derived from the above illustrations, the more flexible a release plan, the more complex the development environment. As the number of development pipelines increase, the complexity of working in the development environment also increases. All development environment tools must support the pipelining strategy and so must the configuration management and problem management processes. The pipeline strategy for a program must incorporate code base synchronization. Code base synchronization must occur among the three pipelines to ensure that the three code bases eventually result in one version in production. FIG. 16 is an illustration showing a multiple release capability development pipeline 1600 with code base synchronization among three pipelines.

Environment Management (906)

Since the development environment is a production environment, it follows that environment management must be planned, organized, and executed to ensure a predictable and productive environment. The present invention can include a comprehensive framework for the Management Of Distributed Environments (MODE), describing four central functions:

Managing Change 820

Service Management 822

Service Planning 824

Systems Management 826

MODE provides an excellent framework for specifying the management responsibilities that apply to the development environment. These responsibilities are often assigned to the technical group, but as discussed above, there are benefits associated with establishing a dedicated environment management team.

The Environment Management component described here uses MODE as a framework, adopts MODE terminology, and focuses on those management tasks, which are particularly important in the development environment.

Adopting a structured approach to environment management, which applies the same principles to development as it does to production, has several advantages:

High-quality support for developers

Significant experience with the operations management tools in an environment, which is generally smaller and which carries lower risk than the full production environment The ability to tune the environment management approach before production roll-out In some respects, the development environment is simpler than the production environment. It is, for example, generally smaller in terms of the number of hardware components and the number of locations. In other respects, however, the development environment is more complex. For example, the amount of change in this environment is generally higher than in the production environment. In fact, the environment can be so fluid that extreme care must be taken to maintain control. On a large engagement, one dedicated technical support person per ten designers and programmers is recommended. The greatest need for technical support is generally during detailed design and programming. It is, however, necessary to start building the technical support function before detailed design.

All processes that are performed by the Environment management team must be documented in a centralized database that allows quick and easy reference.

Service Management (822)

Service Management provides the interface between the Environment Management team, the Development teams, and external vendors or service providers. It manages the level of service that is provided to the developers. In order to maintain this service, three areas must be managed:

Management of Service Level Agreements (SLAs)

Management of Operations Level Agreements (OLAs)

Help Desk

Service Level Agreements

In order to plan and organize the development work appropriately, a Service Level Agreement (SLA) must be in place between the Service Management group (typically part of the Environment Management team) and the developers. As with all other components of the development environment, this agreement should be kept simple. It should specify the following:

The responsibility of the Environment Management team

How developers should request technical support

How quickly a request for support will be serviced

How the Environment Management team will notify developers of environment changes such as changes to databases and common technical modules.

Specifications of service levels should be precise and the service must be measurable. The SLA should also specify how to measure this service (for example, system response times, request service times, backup frequencies). In addition, the SLA must be managed. It may have to be modified as the environment changes, and it must be reviewed with developers on a regular basis to see if the service level is adequate.

a) Operations Level Agreement Management

The Environment Management team is responsible for providing the specified level of service, but frequently relies on external vendors and suppliers to perform certain tasks. For example, hardware service is typically provided by the hardware vendor. To provide the agreed level of service to the developers, the Environment Management team must ensure that external vendors provide their services as required. This generally means establishing a contract with the vendor and following up that the contract is respected.

As the relationship between the Environment Management team and external vendors becomes less formalized (for example, Internet Service Providers, mass market software vendors), it becomes more difficult to provide guarantees on the level of service that will be delivered.

b) Help Desk

The Help Desk function is an important part of the interface between the Service Management group and the developers. The Help Desk makes sure that questions are answered and requests serviced in a timely manner by the right people. In a complex, leading-edge environment, the Help Desk is crucial to maintaining productivity. The Help Desk needs particular focus when:

The system software is immature
The development environment is weakly integrated
The environment is heterogeneous
The amount of newly released custom infrastructure is large
The developers are less experienced While supervisors and coordinators who work with the developers may alleviate the impact of these factors, the more difficult questions must be resolved by the Environment Management group. As some of these will be repeat questions, the ability to log the question, the analysis, and the result in a structured way provides the basis for performing smart searches and answering the question quickly. Repeat questions may also trigger:

Additional training
Modifications of existing training
Additional entries in a "technical hints" database
Changes in tools, procedures, and responsibilities Efficient searches in the Help Desk database can, in some cases, be greatly facilitated by extending the basic functionality of the Help Desk tool. This can be achieved, for example, by adding a smart word search capability on top of the Help Desk history database.

Comprehensive training must be given to Help Desk personnel in order to ensure the best possible level of service to the developers.

In addition to serving internal project needs, the Help Desk must be prepared to coordinate the activities of external suppliers to solve problems. This occurs when several new versions of hardware and system software are introduced, and compatibility issues arise. Part of the coordination is the tracking of request IDs, which refer to the same question but which are assigned differently by each supplier.

To manage communication with external vendors, a contacts database with the following information is useful:

Company name
Products supplied
Details on support arrangements
Address, phone and fax numbers
Main contact
Secondary contacts
Regional office address/fax/phone/contacts
World headquarters address/fax/phone/contacts Based on this information, it is useful to log the exchanges with the external company, indicating:

Date
Individuals involved
Key information exchanged c) Quality Management

Defining the SLA, with its specific, measurable criteria, is the basis for continuous improvement. The continuous improvement effort may focus on providing the same level of service with fewer resources, or on providing better service.

An important part of quality management is ensuring that the Environment Management team understands the key performance indicators for service delivery, that these indicators are monitored, and that all personnel are adequately equipped with the tools and training to fill their responsibilities. While the entire team is responsible for delivering quality, the responsibility for Quality management should be assigned to a specific individual on the Environment Management team.

Systems Management (826)

MODE divides Systems Management into:
Production control
Monitoring
Failure control
Security management
Staffing considerations Production Control In the development environment, a number of activities must be performed according to schedule, including:

Reorganization of databases, including the repository
Rerunning of database statistics
Performing backups
Transportation of backups off-site
Performing periodical file transfers between environments/sites
Preventive maintenance of equipment Many of these activities can be scheduled and performed automatically, but must have some level of manual control to ensure that they are executed correctly. Control tasks may include checking and archiving activity logs. Standards and procedures that describe the control function must be established.

Monitoring

The Environment Management team must systematically monitor the development environment to ensure that it is stable, provides adequate response times, and satisfies the needs of the developers. This monitoring involves looking at trends and extrapolating them to anticipate problems with disk capacity, system performance, network traffic, and so forth.

Failure Control

Failures must often be corrected quickly to restore service. The time needed to restore service is affected by the time it takes to isolate and repair the fault. In many cases, elapsed time can be shortened by allowing remote administration of system components.

Security Management

Security management involves:
Defining security requirements
Preventing security breaches
Limiting the effect of security breaches
Detecting security breaches
Correcting the effect of security breaches Although direct sabotage is rare, inexperienced developers, perhaps new to the project, can wreak havoc to the system under development by inadvertently deleting or modifying system components. Focus must be on defining access rights so that developers have the right level of access (read/write) to all the information that is useful and relevant to their work.

With the opportunity to connect development environments to the internet comes new risks. There is a potential for security breaches or the transfer of viruses and other malicious programs. In extreme situations, where security is of great importance, it may be prudent to isolate the development environment, and allow Internet access only via a dialup connection on stand-alone machines. The overlap of responsibility for Security Management between the Environment Management team and the Security Management team will need to be defined at the program level.

Outsourcing Considerations

In the development environment, it may be possible to outsource certain Systems Management tasks. For example, the LAN supplier may be willing to take responsibility for LAN support, upgrades, and so on. Similarly, an existing data processing center may be willing to take responsibility for host operations. Such agreements are very beneficial and make it possible to use project team members more effectively. However, outsourcing the development environment carries a risk, which can be mitigated by defining a Service Level Agreement with the provider. This will generally be very similar to the SLA established between the Environment Management team and the developers. One important difference is that punitive measures (to be applied if the SLA is not respected) must be specified to ensure that outside suppliers are strongly motivated to abide by the agreement.

Service Planning (824)

MODE divides Service Planning into:
Service Management Planning
Systems Management Planning
Managing Change Planning
Strategic Planning All these planning stages apply in the development environment and are analogous to the kind of planning that must occur in the business application's production environment. One of the most important success factors when providing technical support is being proactive and anticipating the need for intervention.

Service Management Planning

Once the SLA is defined, the resources required for delivering the service can be specified. Questions to address include the staffing of these resources and training to ensure that they are equipped to deliver service as agreed.

Systems Management Planning

Daily tasks must be specified, assigned, and followed up. Systems management planning determines who is responsible and how follow-up is performed.

Managing Change Planning

Managing change planning is of great importance in the development environment. During a large project, several very significant changes to the development environment must be accommodated. They include:
New hardware
Rewiring of the network
New development software
New releases of existing development software
New releases of infrastructure components (custom-built technology architecture)

The release of these components into the environment requires very careful planning to ensure minimal disruption for developers. Techniques commonly used include:
Fallback options if a new component does not function as planned
Partial rollout to a sub-team to limit the consequences if a component does not work as planned
Ample information to developers about timeframes for rollout and expected effects of new components
Well planned testing
Sufficient training for new tools or changes to existing tools Planning for change includes choosing options based on a thorough understanding of the positive and negative impacts of change to the environment. Changes to the development environments should be analyzed and planned for as orderly releases rather than a stream of small modifications. Changes should be packaged into releases, and each new release of the development environment should be tested by developing a small, but representative part of the system using the new environment. Ideally, this test should be performed by real developers rather than by the Environment Management team. This may be very helpful in order to obtain better buy-in.

Strategic Planning

Strategic planning is traditionally regarded as being less important in a development environment than in the production environment, mainly because the development environment is often viewed as a temporary entity that does not warrant serious strategic considerations. This may be changing however, with the concept of the enterprise-wide development environment—a single, generic development environment architecture that is tailored to each specific project. In this case, strategic planning for the development environment is vitally important if the environment is to evolve, and allow the organization to remain competitive. Strategic planning of the environment management function may, for example, include such questions as support for multi-site development and coordination of multi-sourced systems management.

Managing Change (820)

The development environment is subject to constant change (for example, the addition of new tools, or changes to code libraries), which needs to be managed carefully. The Managing Change component comprises three sub-components: Controlling Change, Testing Change, and Implementing Change.

Controlling Change

After planning for and scheduling change, it must be controlled. This ties in closely with Configuration Management (see Processes—Configuration Management).

Testing Change

Thorough testing is required to reduce the risk of productivity loss due to environment changes. Techniques commonly used include:
Careful scheduling of events to minimize disruptions (typically weekends and evenings are used to enable a strictly controlled test of new components released to the design and construction environment).
Rigorous testing of Environment Management tools themselves. This test must be as rigorous as the testing of the execution environment.
A hardware and systems software acceptance test environment where components from external suppliers are validated before the component is accepted into the environment.
One or more separate architecture build and test environments where new or modified custom-built components can be thoroughly verified before they are made available.

In addition to reducing risk, testing should also verify that the expected positive benefits of the change are indeed obtained.

Implementing Change

After planning and testing the change to be introduced, it must be implemented. The most common kinds of change in the development environment are the introduction of additional hardware, new releases of databases, subroutines and infrastructure, and upgrades to tools. Each change implementation should be viewed as continuous improvement so that any difficulties or inefficiencies are analyzed and resulting improvements are planned and implemented. To be effective over time, this requires that procedures be documented and regularly reviewed and enhanced.

When the database is changed, new versions of test-data must be developed and distributed. When infrastructure components are modified, they may have to be distributed across platforms, and the ripple-effects (for example, the need for recompilation or code changes in affected components) must be understood and coordinated. Some projects have experimented with incentives to ensure that the infrastructure components do not change too frequently. One such strong incentive is to make the Architecture team responsible for all ripple effects and have them implement all the application level changes that result from an architecture modification.

Problem Management (912)

Problem Management is generally associated with the discrepancies that result from the testing process, though it may also be applied to the management of design problems detected during verification or validation steps. Problem Management is a crucial process in the system development life cycle. It ensures that quality software is designed, developed, and tested so that initial benefits defined in the business case are in fact realized. A development environment must have a formally defined problem management process to ensure that this objective is met.

Formal problem tracking helps to control the analysis and design process by maintaining documentation of all problems and their solutions. Problem tracking improves communication between developers and business representatives, which is particularly helpful in minimizing misunderstandings at later stages of the development cycle.

Such formal problem tracking also helps to facilitate the solution process by formalizing a procedure for reviewing, acting on, and solving problems in a timely manner. By circulating problem documentation to all affected parties, management can minimize the risk of misunderstandings at a later date. In addition, the documentation serves as an audit trail to justify design and implementation decisions.

It is, however, important to note that not only the software that is developed for business case benefits realization must have a formal problem tracking mechanism, but the development environment architecture must also have a formal problem tracking mechanism. The development environment tools and processes support the design, development, testing, and delivery of quality software. Therefore, the foundations of design, build, and test must be stable and problem free. All problems identified in the development environment architecture must be tracked formally and solved as the development environment is also a production environment for developers.

System Building (918)

Understanding the systems building process is important since well defined development tasks and workflows form the basis for achieving high productivity and consistent process quality. Tools to support these processes may be found in Tools—System Building.

The development environment varies by segment of a systems development project. The following model is used when discussing different components of the development environment.

The development process is iterative and can be entered at different stages depending on the complexity of the changes. Small corrections may not require explicit design, and small enhancements may not require any high-level design. The shaded, elliptical labels in the above figure indicate how the development process can be entered depending on the magnitude of the change.

The iterative nature of the development process is important since it implies that components of the development environment, which are put in place for design (for example), must be maintained, since they will continue to be used until the end of system test and beyond. Multiple releases of the business application may also be under concurrent development at different stages. This may lead to very active use of design, construction, and testing tools at the same time.

Analysis & Design (828)

Analysis and design in this context, refer to the two Business Integration Methodology activities:

Design Application

Design Technology Infrastructure

The most critical and perhaps the most difficult work occurs up front. The success of the entire design effort depends on the quality of the work performed to gather, document, communicate, and analyze requirements in the early stages. Standards for how to document these requirements are very important. They facilitate communication, which, in turn, ensures a common view of the problem to be solved. Communication must be ensured within the analysis team but also with the (possibly future) designers and programmers.

Tool support may help enforce standards, and such tools are discussed under Tools—System Building—Analysis & Design (below).

The design process includes numerous activities, which range from high-level general considerations to low-level detailed issues. The overall objective of design is to transform functional and technical specifications into a blueprint of the system, one that will effectively guide construction and testing. While requirements analysis and specification deals with what the system must do, design addresses how the system will be constructed. Validating that the design actually meets the requirements for functionality, performance, reliability, and usability is essential.

The quality of the design process directly affects the magnitude of the efforts required to construct and test the system, as well as the maintenance effort. Investments in defining high-quality design standards and procedures and integrating tools is therefore particularly important. It may, for example, have a direct impact on the degree of reuse achieved. In addition, adequate training must be provided to ensure that the designers make optimal use of the environment provided.

Information on how to approach system design can be found in the following Andersen Consulting sources:

Delivery Vehicle Frameworks (see Technology Library)

Network-Centric Architecture Framework (see Technology Library)

The Graphical User Interface Design Guidelines (see Technology Library)

Design Application Architecture (see ENACTS MKB database)

New tools and processes link detailed design and construction more closely than before. To realize the expected benefits from repositories and code generation, the output from detailed design must be exact and correct, leaving little room for interpretation. This requires careful quality control and very specific exit criteria associated with the completion of detailed design.

It is important that the development environment accommodates concurrent effort in different areas. For example, parts of design may occur after system test starts, as in the case of an urgent change request, or when a significant inconsistency is detected in system test. Some reverse engineering work may also occur before design or during construction.

When standards, procedures, and tools are developed for a task, it is important to consider where the task belongs in the sequence of tasks that contribute to the development. For example, the use of a repository early in the development process reduces the need for re-entering information while enhancing consistency and facilitating standards compliance.

Usability and User Interface Design

Usability is an important (and often overlooked) consideration in system design. Usability is more than a well-designed user interface—the way in which business processes are modeled, how they are implemented within the system, and how they are presented to the user all contribute to the overall usability of the system. Usability is an iterative process of refinement that results in systems that are easy to learn, efficient, and enjoyable. In the very broadest sense, usability is the thoughtful, deliberate design approach that considers users throughout the solutions-building process, from start to finish. For this reason, usability guidelines should be defined and followed at every stage of system design. This, along with regular usability reviews and tests both internally, and by target user groups (by using prototypes), helps to reduce the risk of a poorly received system.

The User Interface has become increasingly important as systems become more and more user-facing. As multimedia technologies evolve allowing the development of richer user interfaces, so the design processes must adapt to reflect these new technologies. The processes that surround the design of media content are similar to that of regular system design, and many of the same issues that apply to designing traditional user interfaces also apply to the design of media content. The major change is the involvement of media content designers—a group of people not traditionally associated with system design and development. As their presence is relatively new to the scene of systems development, it is often the case that media content designers are not fully integrated into the development team—a potentially costly mistake. It is important to ensure that media content designers are involved in the design process at a very early stage, and that they are fully integrated into the application design and construction teams.

The approach to Interface design is evolving as media technologies become more advanced. Modern media creation tools allow the development of not only media-rich interfaces, but also the functionality that lies behind them. This means that the role of the media content designer may now range from that of designing the look and feel of a user interface, to developing the entire presentation layer of an application. In this situation, the role division between media designer and application developer becomes a difficult one to define, reinforcing the argument for fully integrating media designers into the application development team.

Standards and Procedures

Well documented, comprehensive standards make designers more independent and enable them to produce more consistent, high quality designs. Common standards include:

Detailed specifications of deliverables from each design step

Window and report design standards

Naming standards for design objects and documents

Navigation standards

Standards that specify the design techniques to use

Documentation standards that specify format

Technology infrastructure design standards that specify how to ensure security, handle errors, and manipulate context data While the standards focus on what to do during design, procedures focus on how to do it. Procedures must be in place to specify:

How to resolve functional and technical issues

Which tools to use and how to use them

How to perform design validation

When and how to initiate and perform functional and technical design reviews

How to cope with design teams distributed across locations*

Guidelines give assistance in areas where judgment is important and where standards are not easy to define. Valuable guidelines may include:

Usability guidelines

Style guidelines

Guidelines on how to use a tool effectively

Sample design packet for each kind of system component to be designed

Designers must understand standards and procedures other than the ones listed above. For example, repository related standards are very important to designers. These standards are discussed in Processes—Information Management (above).

Implementation Considerations a) Multi-Site Development

In the case of systems being developed by multiple parties or across multiple locations, it is vital that a process of regular communication is implemented. This communication should involve all the parties involved in the design of the system, and is usually conducted in the form of an audio conference (see Tools—Collaboration). Through this process, it must be ensured that all parties are approaching problems from the same direction, and that they are thinking about the design in the same way. If this is not achieved, there is great potential for misunderstanding across teams, which generally leads to a badly integrated system. In this type of situation, where parties are not working together on a day to day basis, it is also important that any definition (requirements or design) is completely free of ambiguity (if anything is left open to interpretation, there is a high risk that it will be misinterpreted). Practically, this means that quality controls on documentation need to be more stringent than on a traditional single-site project.

Reverse Engineering (830)

Reverse Engineering is a set of techniques used to assist in reusing existing system components. Most of the time, this work is performed manually: one person studies thick listings to understand data layouts and processing rules. The person gradually builds a higher-level understanding of how the components work and interact, effectively reverse engineering the system into a conceptual model. It may be necessary to study certain pieces of code to understand how they work, but reverse engineering is not limited to code. For example, these techniques might help understand the data-model of a legacy application, in order to better design the new applications that will coexist with it.

The process can be very time-consuming and is notoriously difficult to estimate. Tools to support the effort do exist, and have been used successfully to streamline the process. The main problem with such tools, however, is the hasty (and erroneous) conclusion that tools automate everything. They do not, just as design tools do not automate the design process. Human intelligence is still required to drive the effort.

The supporting tools can, however, reduce the amount of manual effort needed and significantly lessen the amount of non value-added activities, such as "find all the places in a program that affect the value of a given variable".

The goal of a specific reverse engineering effort generally falls into one of the following categories:
  To determine which parts of existing systems must be replaced and which can be reused
  To determine how a particular component works in order to design other components that interface with it
  To extract components for reuse
  To prepare for cleaning up those parts of a system that will be retained In component-based development, a concept known as "round-trip reengineering" provides the developer with a way of modifying a component model and generating the code, then at a later date modifying the code at predefined locations in the source code and regenerating, thus enabling the model to maintain a 2-way-syncronization.

Note that components to be reverse engineered can be both part of a custom-built system, or part of a software package.

Projects dealing with the Year 2000 issues have had much experience in reengineering.

Standards and Procedures
  The following reverse engineering guidelines should be used as input when developing standards and procedures for a particular context.
  Reverse engineering can provide important input both to the design process and to the construction process. Timing of the activities is therefore important.
  The interplay between design and reverse engineering can be intricate: a high-level design is needed to determine which components from existing systems are of interest. Once this is determined, these components can be extracted, generalized, and fed into the detailed design process as one source of information.
  The value of reuse will vary with the functional and technical quality of the code.
  It may be useful to clean up existing code before it is extracted for reuse.
  Tools should be chosen based on knowledge of the system, the amount of code to be processed, and the experience of the personnel involved.
  The end should be kept in mind. With powerful tools, it may be tempting to "investigate for fun" rather than extracting what is needed.
  As with all other tools, adequate training is important.

Packaged Component Integration (832)
  Packaged Component Integration applies to the use of any third party (or previously developed) technical components that may be integrated into the target system. This can range from simple components offering limited functionality (worksheet or charting GUI components), to components handling a significant portion of the application architecture (data access components and firewalls). The process involves a number of stages:
    Package or Component Selection
    Component Customization
    Component Interfacing See Tools—System Building—Packaged Component Integration for more details.

Standards and Procedures
  A proven practice in the component-based development world, when dealing with purchased components, is to "wrap" them, i.e. encapsulate them so that the visible piece of any component remains fully controlled. This way, when a component is replaced (either for an update or because it has proved to be defective), no other system components that refer to that component will need to be altered.

Construction (834)
  Construction covers both generation of source code and other components as well as programming and unit test. It may also involve help text creation and string test.

As construction is a large part of system building, the benefits of streamlining this process are significant. Since several aspects of construction are rather mechanical, it is often fairly easy to simplify this process and to automate parts of it, particularly if the design holds high quality.

The arrival of Integrated Development Environments (IDEs), has further simplified the automation of construction processes to the degree that a single tool can manage the majority of the process.

As with Analysis and Design, usability must not be ignored in the construction of a system. Especially in the case of an iterative development approach, it is vital that those responsible for usability and target user groups are involved in regular reviews as the system is being developed.

Standards and Procedures
  Important standards include:
    Programming standards for each programming language, including procedural languages, job control languages, and data access languages
    Test documentation standards
  Important procedures include:
    Code generation procedures, including pre-processing of the code shell and post-processing of the generated code
    Testing procedures
    Test-data handling and common test-data usage
    Procedures for functional and technical reviews
    Code review checklist
    Migration procedures which specify how to make common modules public
  Important guidelines include:
  Usability guidelines
  Shell usage guidelines
  Tools usage guidelines Test (836)
  System test is performed to validate that the gathering and transformation of information is complete and correct.

As automation progresses and an increasing number of business processes are supported by computer systems, system test is changing in nature. Firstly, the testing of interfaces to other systems is becoming an ever larger part of systems test. Secondly, system test increasingly applies to a new release of an existing system. In addition, it is worth noting that as design and construction is increasingly automated, system test is becoming a larger part of the total development effort.

Both of these factors increase the value of automated testing tools, given that the work associated with checking that system changes do not have unintended side-effects, is becoming an ever larger part of system test. Another trend affecting system test is the demand for traceability. Increasingly, users and management wish to know the purpose of a given test condition. This is answered by referring back to the design and to user requirements.

System test is a very large part of any systems development effort and can, especially when requirements are changing, exceed one third of the entire effort. A streamlined environment, which enables high productivity is therefore of utmost importance.

IMPORTANT: When planning system test, it is vital that the testing of all target platforms is included in the test plan. For each platform that is supported by the system, there must be a separate set of tests.

The necessity of impact of volume and stress testing early in the development process is becoming more common, due to the proliferation of new technologies and tools which have little or no performance track record. It is important that the performance and reliability of such tools and technologies is established as early as possible in the project to avoid possible problems further down the line.

Component-based development may have an impact on the way in which testing should be performed.

Standards and Procedures

System test relies heavily on configuration management, repository management, and quality management.

Configuration management provides the basis for promoting a configuration from the construction environment to the system test environment. As test cycles are run and fixes implemented, migration can become complex, requiring flexible mechanisms for locking and unlocking system components and analyzing the impacts of change.

Information management, and in particular repository management, guarantees a correct view of the interrelationships between system components. This is required to ensure that impact analyses are complete and correct, which, in turn, makes for effective regression testing.

Quality management, together with well-defined standards and procedures, ensures that the outputs from each test activity are documented at the right level of detail and fed back to the design and construction teams, in accordance with the quality plan.

Each of the following system test activities needs well-documented standards and procedures and should be supported by tools:

Promote configuration (migrate configurations from the construction environment to the system test environment)

Run test cycle

Compare expected results and actual results

Log System Investigation Requests (SIRs)

Analyze deviations and identify components requiring change (either expected results, test-data, or system components)

Define Change Requests (CRs) and perform impact analysis

Package those change requests that affect the same areas and that naturally belong together, into change packages Schedule and staff the changes Unlock components for change Perform changes and refine impact analysis based on added understanding Verify changes before re-submitting to system test Migrate to system test based on updated impact analysis and re-lock components See the Andersen Consulting V-model for more information.

Implementation Considerations a) Where can I find information about the Reinventing Testing Project (RTP)?

b) What model of testing does the firm follow?

The following is an overview of the firm's testing methodology as documented by RTP. It describes the framework for the testing process, or the V-model of verification, validation, and testing.

c) Are program specifications being tested?

The following is an overview of the component test as documented by RTP. It describes the testing methods used to validate the detailed design stage where program specifications are tested.

Component Test—A component test is the testing of an individual piece of the solution. All components, including application programs, conversion programs, and input/output modules, are subject to component test. The objective is to ensure that the component implements the program specifications. At the end of component test, all lines of code should have been exercised, keeping in mind the specified functional and quality requirements.

d) Are systems design being tested?

The following is an overview of the assembly test as documented by RTP. It describes the testing methods used to validate the technical design stage where system designs are tested.

Assembly Test—The assembly test tests the interaction of related components to ensure that the components, when integrated, function properly. Assembly test ensures that data is passed correctly between screens in a conversation or batch process and that messages are passed correctly between a client and a server. The specification tested is the technical design. The application flow diagram within the technical design depicts the assemblies, either on-line conversations or batch assemblies, that will be assembly tested. Testing is therefore organized by assembly rather than by business function.

By the completion of assembly testing, the system should be technically sound, and data flow throughout the system should be correct. Component and assembly testing ensures that all transactions, database updates, and conversation flows function accurately. Testing in later stages will concentrate on user requirements and business processes, including work flow.

e) Are benefits being tested?

f) Are costs being tested?

g) Are intangibles being tested?

The following is an overview of the benefits realization test as documented by RTP. It describes the testing methods used to validate the business case stage where benefits, costs, and other intangibles are tested.

Benefits Realization Test—The benefits realization test tests that the business case for the system will be met. The emphasis here is on measuring the benefits of the new system, for example: increased productivity, decreased lead times, or lower error rates. If the business case is not testable, the benefits realization test becomes more of a buyer signoff.

Ideally, benefits realization test occurs prior to complete deployment of the system and utilizes the same environment that was used for the service-level test piece of operational readiness test. Tools are put in place to collect data to prove the business case (e.g., count customer calls). A team of people to monitor the reports from the tools and prove that the business case is achieved is still needed. The size of the team depends upon the number of users and the degree to which tools can collect and report the data. The benefits realization test tests that the business case for the system will be met. The emphasis here is on measuring the benefits of the new system, for example: increased productivity, decreased lead times, or lower error rates. If the business case is not testable, the benefits realization test becomes more of a buyer signoff.

h) Are quality requirements being tested?

i) Are technical requirements being tested?

j) Are functional/user requirements being tested?

The following is an overview of the product and operational readiness test as documented by the RTP. It describes the testing methods used to validate the requirement/definition stage where quality, technical and functional/user requirements are tested.

The Product Test—The product test tests the entire application to ensure that all functional and quality requirements have been met. Product testing may occur at multiple levels. The first level tests assemblies within an application. The next level tests applications within a system, and a final level tests systems within a solution. Within the multiple levels, the purpose is the same.

The product test tests the actual functionality of the solution as it supports the user requirements: the various cycles of transactions, the resolution of suspense items, the work flow within organizational units and among these units. The specification against which the product test is run includes all functional and quality requirements. The testing is organized by business function.

The Operational Readiness Test—The objective of the operational readiness test is to ensure that the application can be correctly deployed. The operational readiness test is also commonly known as the readiness test, roll-out test, release test, or the conversion test. The operational readiness test becomes especially key in client/server environments. It has four parts:

Roll out test—ensures that the roll out procedures and programs can install the application in the production environment.

Operations test—ensures that all operational procedures are in place and acceptable, and that the production system can be operated by the personnel responsible for supporting production.

Service level test—ensures that once the application is rolled out, it provides the level of service to the users as specified in the Service Level Agreement (SLA).

Roll out verification—ensures that the application has been correctly rolled out at each site. This test, developed by the work cell or team performing operational readiness test, should be executed during each site installation by the work cell or team in charge of the actual roll out of the application.

The operational readiness test assumes a completely stable application and architecture in order for it to be successful, and therefore, is heavily reliant on the previous testing stages.

The operational readiness test is the point in the development process where all the application development, architecture development, and preparation tasks come together. The operational readiness test ensures that the application and architecture can be installed and operated in order to meet the SLA.

Development Tools Framework

Figure 17:
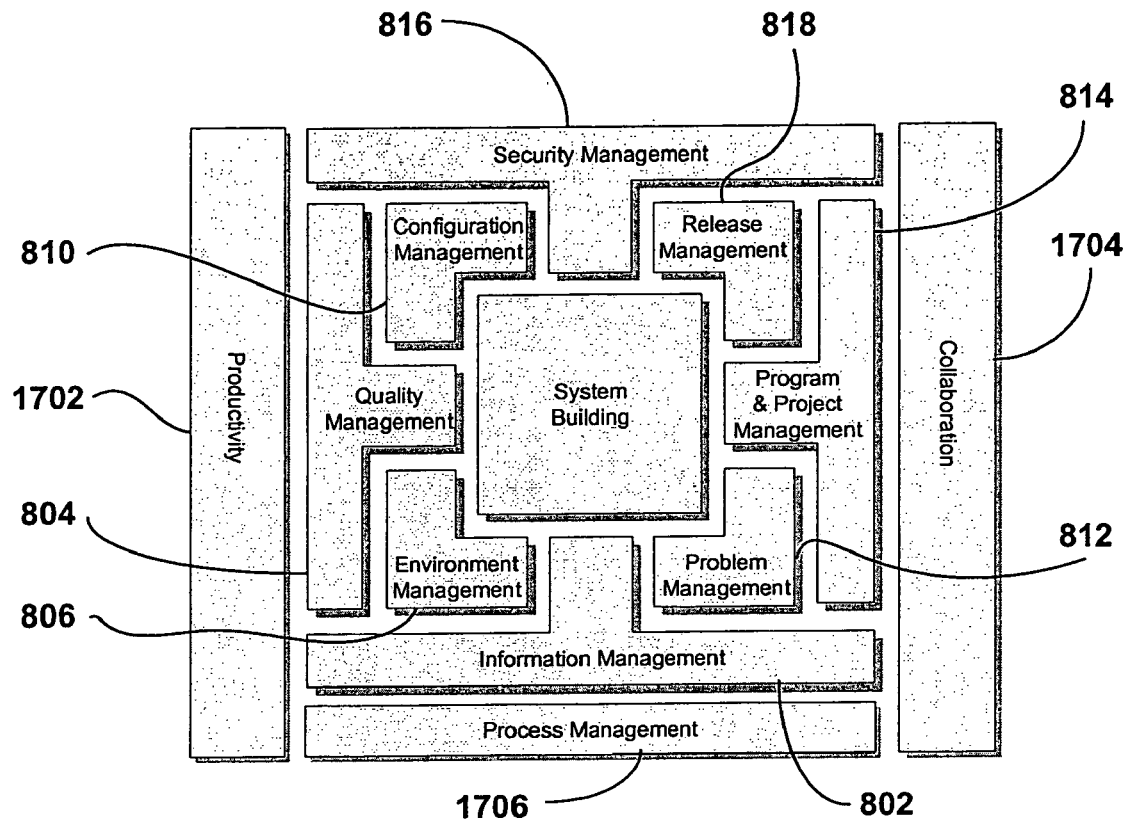
FIG. 17 is an illustration showing a Development Tools Framework in accordance with one embodiment of the present invention.

FIG. 17 is an illustration showing a Development Tools Framework in accordance with one embodiment of the present invention. The development environment is built upon an integrated set of tools and components, each supporting a specific task or set of tasks in the development process. As with processes and organization, the central component, System Building, is supported by the eight management components:

Information Management tools 902 manage the information that supports the entire project—information that is used both in systems building and in other management processes Security Management tools 916 enable the development of security components Quality Management tools 904 support all quality management processes Program and Project Management tools 914 assist the management teams in their daily work Environment Management tools 906 provide the facilities to maintain the development environment Release Management tools 918 manages the simultaneous development of multiple releases Configuration Management tools 910 cover the version control, migration control and change control of system components such as code and its associated documentation Problem Management tools 912 pertains to the problem tracking and solution process In addition, three other components are required to fully support development:

Productivity tools 1702 provide the basic functionality required to create documents, spreadsheets, and simple graphics or diagrams Collaborative tools 1704 enable groups of people to communicate and to share information, helping them work together effectively, regardless of location Process Integration tools 1706 enforce the correct sequencing of tasks and tools in conformance with a pre-defined methodology An efficient development environment requires good tools. For general issues regarding tool selection, please refer to the general Product Selection Considerations.

Productivity (1702)

While many tools are developed in order to support a specific task (for example, source code editor), there is a family of tools that are generally required across the board, often known as productivity tools or office automation tools. These tools, typically packaged as integrated suites of software, provide the basic functionality required to create documents, spreadsheets, and simple graphics or diagrams. More recently, the ability to access the Internet and browse electronic documentation has been added to the suite of productivity tools.

Specifically, productivity tools include:

Spreadsheet

Word Processor

Graphics Editor

Personal Organizer (may be linked to Group Scheduling)

Methodology Browser

Internet Access

These tools are generally versatile enough to take the place of specialized tools (such as planning tools) in certain circumstances.

Implementation Considerations a) How secure does the development environment need to be?

In environments where security is a factor, the way in which team members gain access to the Internet must be carefully considered. For example, on high security projects, it is often the case that isolated machines with a single dial-up connection provide the only way to access the Internet, thus ensuring that the development environment remains completely isolated.

b) Are people using the Internet for its intended use?

Studies have shown that employees spend a lot of time using their Internet access for purposes unrelated to work. Therefore, the benefits and damages of providing Internet access must be assessed.

Collaboration (1704)

It is well understood that both good communication and knowledge sharing are vital for the success of any team. As development projects get bigger and teams more distributed, it becomes increasingly difficult to maintain communication between project team members. Collaborative tools have been developed with this very purpose in mind—to enable groups of people to communicate and to share information, helping them work together effectively, regardless of location.

Implementation Considerations a) How distributed are the project teams?

On projects with development sites that are geographically distributed, it is usually the case that communication by e-mail alone is not a sufficient substitute for meetings when attempting to coordinate the teams involved. In order to keep all teams updated and moving in the same direction, regular (for example, weekly) conference calls between all parties—chaired by project management—is much more efficient. It is important that these conference calls are closely monitored, well prepared, and that the agenda is closely followed. Action points and commitments made during these calls must also be documented. Where issues arise that cannot be resolved using an audio conference (usually because the subject is based on a visual concept), video conferencing may be necessary.

E-Mail (838)

E-mail provides the capability of sending and receiving messages electronically. In addition to the ability to send simple ASCII text, e-mail systems usually provide the capability to attach binary files to messages. E-mail is a convenient tool for distributing information to a group of people, as it has the advantage of delivering content directly to the 'mailbox' of each individual, rather than relying on individuals to access a central data repository in order to retrieve the information.

Implementation Considerations a) Is e-mail likely to contain sensitive information?

When setting up an e-mail system, it is important to consider the content that will be transferred using the system and to apply the appropriate security controls accordingly.

Is communication outside the local environment necessary?

Is remote access required?

If so, a gateway will be required to manage communication beyond the local environment. This will bring with it security implications, as the local environment will no longer be isolated.

b) Do e-mail capabilities already exist at the development site?

If adequate capabilities are already present at the development site, it may well be prudent to take advantage of these capabilities.

Product Considerations a) Is e-mail to be supported on multiple platforms?

The choice of which product to use may depend on the platforms upon which the system must run.

b) How many people should the system support?

Low-end e-mail solutions may be perfectly adequate for small development teams.

Teamware (840)

In a creative environment, it is vitally important that people are able to easily share ideas and information. Teamware provides the ability to capture and share information across a project through the use of common-access, structured databases. A good example of teamware is the Knowledge Xchange. Teamware may be used to share many different types of information, for example:

Technical support requests
Technical hints, which facilitate trouble-shooting
Change requests
Resource reservation (for example, meeting rooms)
Standards and procedures
Status reports/meeting minutes
Project member availability
Project events and milestones
Functional and technical issues
Suggestions
Project methodology In order to guarantee the value of a teamware environment, it is vital that:

Consistency is maintained
Relevant updates are made (including deletions)
Storage is not abused
Security is enforced To ensure that information is consistent across different formats, it is useful to view the management of all these information sources as part of a more general information management process. Effective information management beyond repository management is required to ensure that the anticipated benefits of electronic mail and teamware materialize.

For example, certain teamware databases require continuous maintenance in order to remain relevant. The management of the database contents may require significantly more work than either the initial installation of the tools or the technical support for the tools. This effort is frequently underestimated.

In addition to setting guidelines for general usage, the project must designate mail administrators and knowledge managers who are responsible for:

Maintaining user accounts
Maintaining security profiles
Managing database contents
Removing obsolete information
Managing resource usage (for example, disk space)

Implementation Considerations a) What size is the project team?

Teamware will generally only be effective when used within large groups of people. Unless a critical mass of people is achieved and content is regularly added to the system, interest will soon dwindle, and the system will no longer be of any value.

Group Scheduling (842)

Group scheduling tools help to centrally manage the personal schedules of a group of people. This offers the advantage of being able to coordinate events that require the participation of a number of people automatically by checking 'group availability' rather than checking with each person individually. These tools may also be used to schedule other resources such as meeting rooms and equipment.

For the use of group scheduling tools to be successful, the personal schedules of each member of the group must always be current. This is the responsibility not only of the group scheduler, but also of the individuals involved.

Audio/Video Conference (844)

In an ideal world, all meetings would be conducted face to face. In reality, however, it is often the case that not all the individuals who are required to take part in a meeting are on the same site. To overcome this problem, audio and video conferencing tools allow many individuals in different locations to communicate simultaneously. Audio conferencing is not a new concept, but remains a valuable tool for conducting meetings where the issues being discussed do not require the support of visual aids. Video conferencing takes this one step further, allowing people to interact both aurally and visually, making for a much richer method of communication.

Implementation Considerations a) Is there enough bandwidth to support a video conferencing system?

Adding bandwidth intensive applications such as audio, video, and data conferencing could have severe effects on the network infrastructure and this must be anticipated. This type of implementation is also based on a number of different, emerging standards. The video conferencing system should be designed with that fact in mind and provide for some degree of interoperability between dissimilar systems. For example, being able to connect a desktop-based video conference user with a room-based video conference user.

b) Is video conferencing the right medium for the desired purpose?

Video conferencing is an advantage when one person needs to see the other person's face, his or her reactions, read body-language, build relationships, and so on. On the other hand, when communication is more technical, for example, fixing a bug, collaborative design, document writing, or presenting a demonstration, it is more critical to be able to see what the other person is seeing, or to be able to show information at hand. In this case, application sharing assumes greater importance. It is a common misconception that video conferencing replaces working in the same place. The logistics involved in setting up a group video conference for different time zones, and the complexity of sharing a common whiteboard, limit the value of the solution to occasional situations. In a development environment, the real value of synchronous communication is not in being able to see someone else at the other end, it is in being able to share a working session on a work object (see Collaboration—Shared Workspace, below).

Shared Workspace (846)

Shared workspace systems may be categorized as follows:
Electronic whiteboarding
Application sharing Electronic Whiteboarding An electronic whiteboard provides a large, clear screen that can be viewed close up and at a wide angle, upon which participants may 'write' with an infrared pen or a mouse. Images may also be pasted onto the whiteboard.

Regular workstations on a network may also be used for electronic whiteboarding, providing the appropriate software is installed. Electronic whiteboarding often works in conjunction with video conferencing applications.

Application Sharing

Application sharing allows participants to see and control the same application running on multiple PCs. In this way they can simultaneously create and edit a single, common file. Application sharing may be combined with audio conference.

Process Management (1706)

Process Management may be categorized into two areas:
Simple process integration 848, which concerns the simple integration of a sequence of tasks, according to a prescribed development methodology.
Workflow management 850, which concerns more sophisticated situations where several complex processes require the participation of multiple groups.

In either situation, the aim of the process management tools is to enforce the correct sequencing of tasks and tools. Task integration must be provided in accordance with the methodology and should provide direct support for the methodology. Effective task integration therefore reduces the need to consult the methodology.

Simple Process Integration (848)

Simple Process Integration concerns the integration of a limited sequence of tasks, for an individual, according to a prescribed development methodology. For example, the construction process can be supported within an integrated development environment tool by a menu with the following choices:
Generate module template
Generate windows and dialogs
Edit code
Compile
Link
Edit test plan
Generate test data
Execute test with debug
Execute test without debug
Edit script
Compare results The sequencing of the menu items help to remind the programmer of the steps needed to complete the construction of the program.

Going beyond mere sequential use of tools, real-time integration of tools enables real-time data interchange. The most common example is perhaps the edit/compile/debug cycle. Here it can be very helpful to work in an integrated environment that uses the editor and places the cursor at the position corresponding to a syntax error or to a given break-point defined to the debugger. This integration is generally offered as a standard feature of an integrated development environment. Task integration for the individual can be achieved using scripting tools or a desk top manager.

Real-time tools integration is most commonly provided by vendors who deliver integrated environments.

Workflow Management (850)

When processes become complex and require the participation of multiple groups, simple integration techniques are not adequate for managing the process flow. Workflow Management tools address this problem by providing the ability to define, manage, and execute automated business processes through an electronic representation of the process, both in terms of what has to be done, and by whom. For any process where multiple groups are involved, well-defined procedures must be in place to ensure that work flows from one task to another. Each participant must have access to the information required to perform the task, including the information from previous steps in the flow. This can be handled manually or supported by tools. If handled manually, it requires dedication, attention to detail, and significant training.

Workflow Management can be applied to many processes within the development environment, such as quality assurance, migration, design/construction, system test, and standards development.

Implementation Considerations

Efficient tools support for Workflow Management requires standards and procedures that specify:
Which tasks exist
Expected and maximal duration of each task
What the decision points are
How the tasks fit together to form a workflow
How work is routed depending on the nature of the case/issue
Which roles exist
Which roles can perform which tasks
Which individuals can fill which roles
Priority of cases (for example, depending on the originator)

Product Considerations

Workflow Management tools must at a minimum provide support for
Workflow definition
Case Routing with
Flexible assignment
Escalation
Exception handling
Reporting Tools to assist Workflow Management should support the following:
Specification of individuals, their roles and tasks, and their relationships
Specification of the workflow
Automatic routing of cases
Exception handling if a task is not performed within a prescribed elapsed time
Routing of a case based on its contents (for example, different decision processes depending on the importance of the decisions)
Assignment of cases to roles and to individuals, with manual override
Assignment based on priority
Re-assignment of cases
Reporting Security Management (916)

Security Management tools provide the components that make up the security layer of the final system, and may provide required security controls to the development environment. While some of these tools may be considered as nothing more than security-specific Packaged Components, many are an integral part of the development environment tool set.
Security Management tools include:
Intrusion detection—discovers and alerts administrators of intrusion attempts.
Network assessment—performs scheduled and selective probes of the network's communication services, operating systems, and routers in search of those vulnerabilities most often used by unscrupulous individuals to probe, investigate, and attack your network.
Platform security—minimizes the opportunities for intruders to compromise corporate systems by providing additional operating system security features.
Web-based access control—enables organizations to control and manage user access to web based applications with restricted access.
Fraud services—methods of verifying the identity of credit card users to reduce the amount of fraudulent credit card transactions.
Mobile code security—protects corporate resources, computer files, confidential information, and corporate assets from possible mobile code attack.
E-mail content filtering—allows organizations to define and enforce e-mail policies to ensure the appropriate email content.
Application development security toolkits—allow programmers to integrate privacy, authentication, and additional security features into applications by using a cryptography engine and toolkit.
Encryption—provides confidential communications to prevent the disclosure of sensitive information as it travels over the network. This capability is essential for conducting business over an unsecured channel such as the Internet.
Public key infrastructure—provides public-key encryption and digital signature services. The purpose of a public-key infrastructure is to manage keys and certificates. A PKI enables the use of encryption, digital signatures, and authentication services across a wide variety of applications.
Authentication system—provides a business with the ability to accurately know who they are conducting business with.
Firewall—protects against theft, loss, or misuse of important data on the corporate network, as well as protection against attempted denial of service attacks. Firewalls may be used at various points in the network to enforce different security policies.

Product Considerations a) Does the tool use Role-based access control?

Role-based access control establishes access rights and profiles based on job functions within the environment. If different access rights are required for security administrators vs. code developers vs. code reviewers vs. testers, then the correct access can be established based on these functions.

b) Does the tool have flexible auditing capabilities?

The security administrator should be able to granularly configure what is being audited by the tool. The audit logs should be able to optionally record User ID, time-of-day, location of access, successful and unsuccessful access or change attempts, etc.

c) What are the performance implications of the tool?

Some security services, such as content scanning or auditing, may add noticeable processing time and requirements to the system. Tools should be architected in such a way that performance impacts are or can be configured to be minimal.

d) Does the tool comply with industry accepted standards?

Many standards are emerging in the security technology marketplace. These include standards for cryptographic services, directory services, IP security, etc. In order to enhance future integration possibilities, choose vendors who are developing open solutions which comply with standards.

Information Management (902)

Information Management of the development architecture is provided through an integrated development repository. At this level of integration, tools share a common repository of development objects, design documents, source code, test plans and data. Ideally, the repository would be a single database with an all-encompassing information model. Realistically, the repository must be built by integrating the repositories of the different development tools through interfaces. Tool vendors may also build part of the integrated repository by integrating specific products.

Implementation Considerations a) Is there a desire to enforce consistency in the development effort?

Engagement teams should consider the use of a repository to enforce consistency across development efforts. A repository can store standard data, process, design, and development objects for use during application development activities. Developers then use these standard objects during implementation. As objects are defined once in the repository and reused throughout the implementation process, applications display a consistent look, feel, and flow while enforcing the standards inherent in the repository objects.

b) Will analysis and design objects be reused?

Based upon engagement experiences, an engagement team should consider using a repository when the development team reuses analysis and design objects and deliverables during later phases of the development process. A repository houses many application development components including data definitions, process models, page designs, window designs, common GUI widgets, message layouts, and copybooks.

These components can be reused across large development projects to increase developer productivity and decrease the risks associated with coding and testing the same components multiple times.

c) How large is the development team?

Large development teams require more standardization and control in order to ensure that the team remains productive and maximizes reuse of analysis and design components. A repository provides the development teams with the ability to reuse objects defined in the repository in a controlled manner. Most engagements consider using a repository once the number of developers exceeds ten.

d) Is the development team geographically dispersed?

An Information Management repository is crucial when teams whose designs must integrate are in different places. The repository becomes a means of communication that is formal and enforces the agreed interfaces.

e) Do a number of tools need to be integrated?

A repository management tool may be required to provide an integration platform for existing and future tools, providing communication among all tools where appropriate.

Product Considerations a) Is support for user defined objects required?

The repository may need to be extended by the Engagement team to support custom objects defined by the Application Development team. Some repositories support user-defined objects as part of the base functionality. Others allow customization of the repository by the user while some are not designed for customization at all. If the repository requires extensive customization, a buy versus build decision may be required.

b) Is a logical or physical repository more beneficial?

The Engagement team must consider the costs and benefits of a physical repository versus a logical repository. A physical repository is implemented as a single product. Many CASE tools employ this type of repository by housing all application development objects in a single source. Application development tools are then tightly integrated with the repository.

A logical repository integrates multiple tools to form an application development repository. The various tools employed in the development environment are bridged together by custom architecture components. This approach is commonly used when the Engagement team takes a best of breed approach to tool selection.

c) What are the current and proposed future platforms?

The Engagement team should determine whether the repository must support multiple platforms. The selected tool should not only support current platforms but also support the future platform direction of the project.

d) Does the product support multiple versions of objects?

The repository should support multiple versions of objects. By doing this, the repository can support applications in multiple phases of development. The repository tool should control access to the versions of objects by providing check-in and check-out functionality. This allows multiple developers in various phases of development to work from the same repository while allowing only one developer update access to a particular object at a time.

e) Are there existing tools that influence the selection of the Information Management tool?

Engagement teams have found that tools used in other parts of the client organization influence the selection of a repository tool. Clients may have experience and existing skills with certain Information Management tools that drive the decision to use those tools corporate-wide on other initiatives. The KX may also provide input to the tool selection process based on previous experience and skills of team members.

f) What are the other capabilities of the tool?

Engagement teams often chose a tool that can be used in other areas of the development environment. Many Engagement teams select data modeling tools that can double as Information Management tools. Using one tool for multiple purposes results in fewer integration points in the architecture and less time and cost training personnel on multiple tools.

g) Should the Information Management tool support multiple repositories?

As many repositories do not provide sufficient versioning functionality, it is common to have more than one repository on large projects. Typically there would be one repository for development, one for system test, and one for production. This improves overall control. Another reason could be that there is concurrent development of different releases, each requiring its own repository. Hence, on a large project, a tool that supports multiple repositories is often a requirement.

Does the Repository Management tool allow only authorized changes to be made to its contents by providing some form of access control?

The repository contents are effectively the building blocks of the system and have broad reuse. A facility for security is required to prevent unauthorized changes to the repository elements and hence to ensure high quality and consistent repository content. For example, restrictions are often placed on making changes to data elements because ad-hoc changes by a single designer could have devastating impacts on other parts of the design.

Repository access control is important where developers in the development environment need to be assigned different rights to the repository. Typically, the developers will be placed in groups with diminishing access rights such as repository administrator, technical support, designer, or programmer. These access rights may relate to read/write/modify/delete authority. This method of access control is far more flexible than simple object locking.

h) Does the tool provide repository reporting facilities?

Repository reports serve as an audit trail for changes to objects within a repository and can be used to communicate these changes to the entire team. The Repository Management tool should provide this utility.

Reports for impact analysis are extremely useful in the change control process. As the repository maintains relationships between repository objects, 'where-used' and 'contains' report facilities can be very useful when dealing with change requests.

i) Is the tool an active or passive Information Management tool?

Active Information Management tools can be used to generate components, whereas passive tools are used to hold information about the tool but are not used to build the system. The use of an active Information Management tool increases productivity because of the facility to generate components.

Does the tool need to be customized to provide an integration platform for all the tools in the current development environment as well as those to be supported in the future?

If the repository needs to be customized in order to integrate with all the required tools, then it is important that the Repository tool has a published interface and underlying data model. Using such a repository makes interfacing other tools with the repository considerably easier and less time consuming.

Flexibility is important if a number of point tools are to be used in the development process as opposed to using an integrated CASE tool j) Does the tools repository support validation?

All key characteristics of repository objects (for example, data elements) and their inter-relationships should be validated. Taking data elements as an example, these characteristics may include:

Naming standards for data element names

Naming standards for variable names associated with each programming language

Data element types

Data element length and precision

Data element window display and internal precision.

At a minimum, naming standards must be validated to allow better navigation of the repository and easier reuse of elements.

Does the tool provide a means of describing entities, such as source code files that do not exist as repository objects?

The integrity of references to entities that exist outside the repository but within the folder management system must be maintained. If the tool does not directly support this, procedures will have to be put in place to ensure the consistency of references to these entities.

Repository Management (802)

Repository Management is the key information management tool. The repository should be:

Open, with a published interface and an underlying data model. In some development environments multiple repositories may be used. One repository can be integrated to an upper-case design tool, and another one to a lower-case design tool, each of them offering the best capabilities in their respective domain. It is then key that repositories offer import/export capabilities, so proper bridging/synchronizing capabilities can be developed.

Extensible, affording the flexibility for extending the type of information that can be captured.

Integrated, with the tools that are used to populate the repository and to draw information from the repository.

Scalable, the repository-enabled environment must be able to support tens to hundreds of users simultaneously, and tens to hundreds of thousands of repository relationships. It should also scale downwards, so that it can also be easily used by small projects. This is a major criteria for usability.

Figure 18:
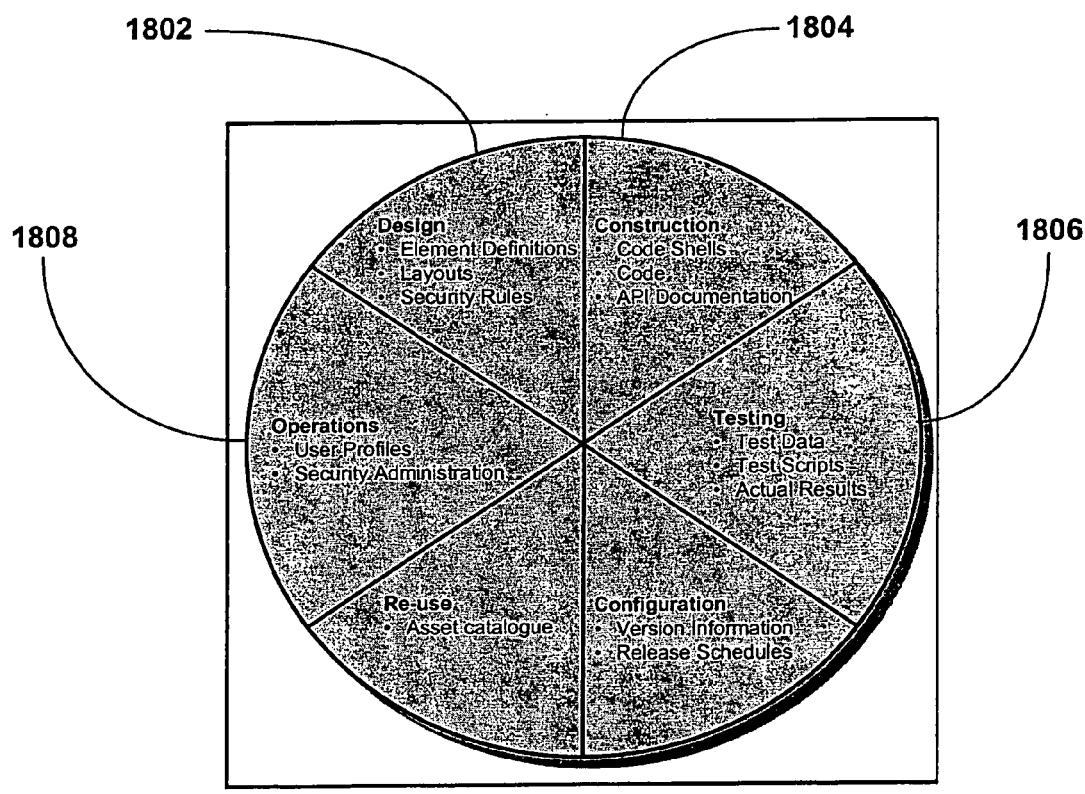
FIG. 18 is an illustration showing information captured in the Repository and reused.

FIG. 18 is an illustration showing information captured in the Repository and reused. A development repository results in three important benefits for a development organization and for the business units they support:

Information is kept in one place, in a known and organized structure. This means that effort is not wasted initially in recreating work that already exists and effort is not wasted later on when reconciling relevant information. This is often referred to as "full life-cycle support."

Design information, created for one step of the development process, can be fed to the next step, reducing effort and knowledge "gaps" or misunderstandings.

The repository captures information relevant to each stage in application development: design 1802, construction 1804, testing 1806, migration, execution, and operation 1808.

The challenge is to create such a repository. Most of the available tools on the market do not explicitly support this comprehensive concept of a repository.

The alternative is to:

Extend the repository. This is why the extensibility of the repository is so important. When extending the repository, consider how well future versions of the base repository will accommodate the extensions. Migrating to a future version may be more difficult after extending the repository. Extending the repository therefore requires a careful trade-off.

Use several repositories. It is not infrequent to see two repositories coexisting; for example, one upper-case and one lower-case repository. Bridges between these repositories are key. Quality of import/export capabilities of the various repositories are key.

In many instances, content may not be stored directly in the repository and must be placed in storage. In this case, only a reference is stored in the repository.

Figure 19:
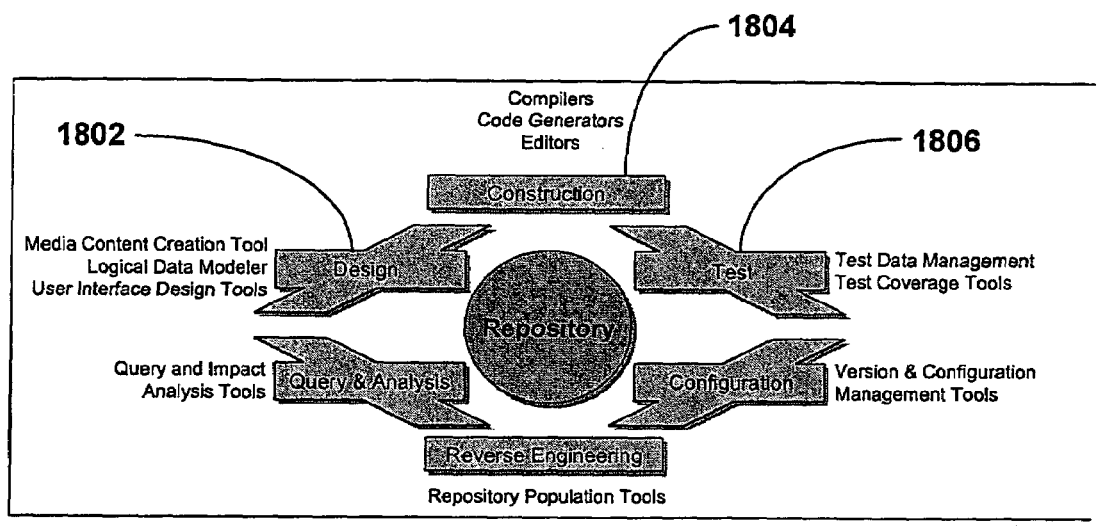
FIG. 19 is an illustration showing the Repository's central role in the development environment.

When complete integration is achieved, the repository can serve as a communication enabler for a large collection of development tools. FIG. 19 is an illustration showing the Repository's central role in the development environment.

This can be achieved either by using an integrated CASE tool, or by integrating point tools around a common repository.

In addition to the repository, which plays a key role, other important tool categories include the following.

k) Security

Repository access can sometimes be controlled using an access control function, which comes with the repository. A common technique is to group users and assign different access rights to the different groups. Each of these groups is also assigned specific read/write/delete/modify authority. For example, the following groups may be defined as having increasing rights:
Programmer
Designer
Technical support
Repository administrator A less flexible alternative is to lock objects. A locked object cannot be changed until the repository administrator unlocks it. This is a less flexible approach but may be used when flexible access control functionality is not part of the repository. A tricky, and somewhat risky, approach to compensate for lacking access control functionality is to use information about the repository's internal storage mechanism to design an access control scheme. For example, if data elements are stored in a particular directory, tools from the network operating system can be used to limit access to that directory. If data elements are stored in a particular table, tools from the DBMS can be used to limit rights to that table. How well this works depends on how gracefully the repository handles error messages from the network operating system or the DBMS. This approach should be tested before it is implemented.

l) Repository Maintenance

Creating and Changing Data Elements—As soon as data element maintenance becomes structured and is based on formal requests, it is practical to make the requests available to the developers in electronic format. Ideally, the requests should be entered into a database, which also contains information on status, comments on the request, and other pertinent information. This database can be a useful communication vehicle.

An alternative approach to maintaining history in cases where the repository does not offer good versioning capabilities, is to maintain a shadow repository where previous versions of repository objects are stored. This only works for those repository objects whose maintenance is strictly controlled.

Creating and Changing Other Repository Objects—It often occurs that the repository is part of an integrated CASE tool. Here, the tools used to populate the repository come with the repository and the integration work is already complete.

This, however, is not always the case. In some instances, the tools for populating extensions of the repository are not provided, and in other cases, a stand-alone repository is used. In these cases, the integration between the design tools and the repository must be performed by the Technology Infrastructure team. This was achieved on a number of projects that chose a "best-of-breed point tool" approach where they integrated these point tools around a repository. The integration may require some challenging work writing parsers, which analyze the output from the individual point tool, and use this to populate the repository. These technical complexities should be hidden from designers and programmers by providing friendly interfaces to the parsers, or by having the repository administrator trigger the parsing at regular intervals.

Repository Validation and Mass Changes—All key characteristics of data elements, and their inter-relationships, should be validated, including:
Naming standards for the element name
Naming standards for the variable name associated with each programming language
Type (for example, numeric and alphanumeric)
Length and precision
Window display and internal precision
Similar validation can be performed on other repository objects depending on project standards. At a minimum, naming standards must be validated. This helps designers navigate the repository and thereby encourages reuse.

Import and export utilities, which provide exchanges between the repository and flat files, can be useful in several ways. They make it easy to take a snapshot of the repository for archiving, and they allow for reuse of the contents of other repositories.

m) Analysis, Reports, and Queries

Reports for impact analysis are extremely useful in the change control process. As the repository maintains relationships between repository objects, where-used and contains reports are usually provided with the repository. Storing the names of affected repository objects in an area-affected table can be useful when grouping change requests during assignment, or when defining a release. The area-affected table is also a valuable tool that can be used to facilitate migration from development to system test.

The ability to easily create various repository reports is important to leverage the information in the repository. A scripting language, a simple report builder, or a query tool provides this capability. Having a query tool with an intuitive user interface and good report formatting features is a necessity on a large project. The query tool can be used to provide standard reports for designers and programmers, printed design information for external reviews, and ad hoc requests for the repository administrator.

Folder Management (804)

It is not always practical to store all information in the same repository. One reason for this is the repository's physical implementation. For example, if the repository is implemented on top of a relational DBMS, this supporting structure does not provide good support for storing flat files. It may therefore often be most practical to populate the repository with place-holders for entities which reside outside the repository. With this scheme, the place-holder serves as a logical pointer. This scheme obviously requires some work to ensure integrity, but in practice it can work quite well. It works better if the objects outside can be organized in a structured way. This is where folders come in. They can be used to impose a structure on flat files; a structure, which can correspond to the structure of the repository. Folders should provide:
Flexible access rights based on user profiles, which differentiate (at least) between read and write access
Efficient search for a component across several folders
Migration between folders
Nested folders
Links to avoid duplication of components while still showing that a component belongs to several folders Media Content Management (806)

Methods for storing and managing media content range from simple folder management techniques to multimedia digital asset management systems, capable of indexing and manipulating numerous multimedia data types. There are a number of key requirements for Media Content Management—in particular, a Media Content Management system should have the ability to:
Manage multiple file formats
Efficiently store high volume files Manage metadata on files within the system
Manage multiple versions of media files
Manage revision history of changes to media files
Control media storage across locations (online, near line, offline)

Whether the functionality described above is handled as an integral part of the system, or by manual processes implemented by the Information Management team depends on the richness of functionality provided by the tools chosen.

Additional functionality provided by advanced Media Content Management tools may include:
Intelligent indexing of media types (allowing specialized search facilities)
Capabilities for browsing media content (low-res images, previews)
High performance proprietary file systems (both in terms of speed and volume)

Implementation Considerations a) What formats need to be supported?

The method of Media Content Management depends heavily on what media is to be stored. Ensure that the target media formats are understood before implementing the Media Content Management approach.

b) Where should media content be stored?

Where to store media content greatly depends on the volume of media to be stored, and the performance requirements for retrieving that data. One thing is certain however; when dealing with large quantities of media, it is necessary to employ a dedicated media server, thus avoiding volume and performance hits with the rest of the development environment, while allowing the possibility of tuning the media server for optimal performance.

The cost of data storage is not insignificant, especially when considering the total cost (not just that of the hardware and software, but also the effort required to support it). This means that much thought must be put into a media storage strategy. This includes a strategy for deciding which media should be on-line (instantly accessible), near-line (accessible with short delay, for example, CD juke box), or even possibly off-line (manual intervention required).

Object Management (808)

Object Management tools provide capabilities for viewing objects, their methods and attributes, and the dependencies between these objects.

Object Management tools also provide specific analysis tools, in order to understand interdependencies between the core classes and the components. When classes and components are modified, impact analysis tools are required to see where the modified entity is being used, allowing them to understand what is the overall impact of the change. This is more complex than with traditional systems as a veritable spider's web of dependencies between classes, components, and applications may ensue. In addition, OM features such as inheritance and polymorphism make tracking down dependencies with simple text search tools much more difficult.

Quality Management (904)

Quality Management is a management discipline that promotes a customer satisfaction focus and continuous improvement. Quality Management tools support the definition and implementation of quality.

A number of integrated Quality Management tools are available that may combine the functionality of all the required quality subcomponents into a single product. Many quality processes however, (such as Expectation Management) do not require specialized tools, and are therefore supported by standard productivity tools.

Metrics (810)

Metrics are an important part of quality management in that they provide a method of measuring (for example, sampling, testing, and determining) whether a process or product meets a given criterion. With Metrics, different stakeholders can agree that a product objectively meets an expectation, or that a process has been improved by a measurable amount. Without Metrics, stakeholders can only have subjective opinions that may or may not agree.

Measurement tools are used to measure process quality and product quality. Process quality may include Metrics such as the time it takes to process a change request. Product quality should be measured for all the product expectations the project has set. This measurement process is the inspection part of quality management.

Statistical Process Control (852)

Statistical Process Control tools are used to analyze the results obtained with the measurement tools. These display trends that can be used as the basis for process improvement or, in other cases, product rework.

Continuous Improvement (812)

Continuous Improvement tools are used to analyze and improve the development processes.

Continuous Improvement is a process management technique by which action is taken to modify a process when the measurement or outcomes of that process are unsatisfactory. Process improvement is required whenever the number of defects exceeds the desired level, productivity falls below a desired threshold, or client expectations fail to be met. Once the process has been modified, it is remeasured to see whether the expected gain was actually achieved.

Training (854)

Training tools provide methods to apply a standardized training approach to a large group of people. Training tools can complement or take the place of traditional instructor-led training depending on the type of information that must be communicated. Computer-Based Training (CBT) tools offer the advantage of being able to train personnel directly on the target environment.

At the more basic level, training tools can also include online or paper-based training materials—not offering all the advantages of CBTs, but still providing the flexibility and convenience because they can be conducted as and when the trainee requires, and in any location. This removes the need to organize classes.

The decision of whether to use CBT, online, paper-based or instructor-led training is affected by the number of people that have to be trained, the complexity of the subject, and the availability and distribution of the people to be trained.

Program & Project Management (914)

Program and Project Management tools assist the management teams in their daily work. These tools, typically packaged as integrated suites of software, provide the basic functionality required for planning, scheduling, tracking, and reporting at both the program and project level.

Planning

Planning tools are used to assist in program and project planning including the development of the Program Resource Plan, the Work Breakdown Structure (WBS), the Organization Breakdown Structure, Cost Accounting, milestones, and deliverables.

Scheduling

Scheduling Tools are used to allocate resources against the WBS, to determine the timeline for a specific project, and to schedule the allocation of resources at the program level.

Tracking

Project tracking tools enable the project manager to track the actual project status against the original plan and schedule. Integration with the time reporting system and techniques such as Estimates to Complete (ETCs) are valuable in tracking project status.

Reporting

Reporting Tools are used to summarize status and metrics to program and project management.

Configuration Management (910)

Configuration Management tools ensure that consistency between components and a given environment is maintained over time as components are changed.

Implementation Considerations a) Does the testing effort involve numerous applications with common components?

Engagement teams frequently require Configuration Management tools to support the testing process. Large development efforts may have multiple releases of an application in the development pipeline (development, unit test, integration test, user acceptance test, and production). Additionally, some environments have multiple applications that share common components. Multiple versions of common components may be required depending upon the application being tested. Configuration Management tools assist in migrating code between these environments. These tools can also be used to manage different versions of test scripts for various releases of an application.

b) Where is the development team located?

Configuration Management tools are essential when development teams are not centralized at one location. These tools provide services, such as version control, when geographically distributed teams need to access common modules or data, such as code tables. Configuration Management tools may still be necessary even if the development team is centralized, depending upon other criteria such as development team size.

c) How large is the application or development team?

Large applications, as well as large development teams, require Configuration Management tools to help control versioning of code, changes to code, and migration of code (and accompanying design and test documentation) through the development and testing environments.

As the size of the team increases, the communication between team members becomes more cumbersome. The Configuration Management tools provide a structure for communication between team members regarding version control, change control, and migration control.

As the size of the application increases so does the number of objects, files, or components. The management of these items becomes increasingly difficult to manage and track during the development process. The Configuration Management tool provides structure for managing the objects, files, and components and reduces the risk of lost information caused by version problems, or by items not being migrated properly.

d) Is the development effort to be sustained over a prolonged period?

Over time, a large number of configurations will evolve and Configuration Management tools can be used to control the evolution and to document these configurations.

e) Is there a large number of components?

It may be necessary to keep track of and control configurations consisting of objects such as training materials, documentation, hardware components, system software and even building characteristics. The existence of a large number of such components makes the task of managing their configurations complex, and a dedicated Configuration Management tool becomes crucial to the process.

f) Are multiple organizations contributing?

Configuration Management tools are particularly important when there are multiple vendors and subcontractors involved and there is a need to align what is assembled in preparation for the integration test.

g) Does the system exceed 100 modules?

Configuration Management tools are needed once the system becomes large and many modules (which may include programs, header files, copybooks, shared components, subroutines, and so on) have to be managed. There is a significant cost involved in formal configuration management. If the system has a little over 100 modules, the Configuration Management component may consist merely of a whiteboard or Excel spreadsheet. As the number of modules grows to about 1000, a dedicated tool is required.

h) Do the generations or versions of components change frequently?

A Configuration Management tool is important if many generations or versions are to be managed. This will generally be the case if the project involves a large development team. There may be external factors that the project team has no control over such as hardware vendors who change their configurations frequently. The internal components, for example, software modules must be configured to match external components such as operating systems and hardware components.

Product Considerations a) Should the engagement team build a custom configuration management tool or purchase an existing one?

An engagement team must determine whether to purchase a Configuration Management tool or build one. The build decision should consider the cost of designing and developing the functions required by the engagement team. Additionally, the project must consider the resources and development time required to build the tool and when the tool is needed in the application development schedule.

The buy decision can still be expensive and requires additional investments for training project personnel. These tools also provide many features that may not be required by the engagement team.

b) Does the engagement team have more experience with certain tools?

Engagement teams found that tools used in other parts of the client organization influence the selection process. Teams may have experience and existing skills with certain Configuration Management tools that drive the decision to use those tools on other initiatives corporate-wide. One may also provide input to the tool selection process based upon previous experience and skills of team members. Using tools that the engagement team already has experience with provides several advantages, especially a reduction in training costs.

c) Does an existing component satisfy this requirement?

Engagement teams sometimes choose tools that provide multiple development functions, including Configuration Management tools. The decision to choose between available Configuration Management tools may already have been decided as a result of using certain other tools within the development environment.

d) Does the product integrate with the existing or proposed architecture?

The engagement team should select tools that integrate with other tools in the development environment and operate on the same platform. Project teams should select tools where vendors provide support for the integration between the Application Development tool and the Configuration Management tool. Such integration helps to easily and effectively manage the objects or files created by the Application Development tool.

How does the project define a configuration?

Does the tool handle all types of components in the configuration?

The components involved in Configuration Management typically involve hardware, system software, and application components together with their documentation. The tools should be able to manage and keep track of all the component types that make up a configuration.

e) Does the tool provide capabilities for exception reports?

If for some reason a repository component is not at the correct promotion level, the tool should be able to report on this when required.

f) Will a source control system suffice as a Configuration Management tool?

Generally, source control systems must be enhanced to provide a basic Configuration Management tool. The functional enhancements are typically:

Definition of a grouping mechanism for files to associate them with certain versions.
Promotion mechanisms
Definition of interconfiguration dependencies such as between a particular version's files and that version's related test data.

g) Does the tool provide ease of access to information?

The tools should automate the storage and retrieval of all dependent software components indicated by an impact analysis report.

Version Control (814)

Version Control tools control access to source code as it is developed and tested and allow multiple versions to be created, maintained, or retrieved. For example, a source code comparator can be used to identify changes between different versions of programs.

The component-based development raises a new challenge: when a single component is used by several applications, versioning becomes significantly more complex and therefore, advanced versioning software, including system support for versioning, is required.

Implementation Considerations a) Should the evolution of the system be tracked in terms of who makes changes or why certain decisions are made along the way?

Version Control tools allow systematic storage of information about who makes changes in what order so that the evolution of the system can be tracked. The tools usually provide a facility to report on differences in versions so the version that existed when a critical change was made can be identified and recreated or retrieved. The tools can also provide a means of documenting why decisions are made during the evolution of the system. These decisions would have been made based on the version of the documentation for the system that existed at that time. Version Control tools allow the state of the system at a particular time to be recorded. Hence improved auditability for decisions can be achieved.

b) Is there a large development team?

Version Control tools allow developers to work semi-independently and to choose the degree of integration they need at any given time. They can shield themselves from the tentative development performed on shared components and test a portion of the system with a stable environment around them. This prevents the development team from having to develop one full sequence at a time and increases the ability of a large number of people to work productively together, thus compressing the time required to develop a system.

c) Is there concurrent development of multiple versions of the system?

A comprehensive Version Control tool set is critical if there is concurrent development of multiple versions of the system. This is often the case when system development is to be sustained over an extended period.

Special provisions must be made to ensure that the library and repository structures are rich enough to be able to support the necessary versions. In this environment, a log of changes also becomes very important as fixes applied to earlier versions generally have to be applied to later versions as well.

d) Is it likely that the system will need to be rolled back to a previous version at some stage in the development?

This is typically the case when the project is breaking ground, using new techniques or untried architectures.

Version Control tools provide a means of taking snapshots of the system in time. If there are changes in the environment that force the system to be rolled back to a previous stage in the development, Version Control tools allow access to previous versions and mechanisms for reverting to an earlier version.

e) When should I set up version control?

Version Control should be set up from the beginning. By delaying version control, manual Version Control must be used. This result can be an increased cost in disk space in the development environment (because of the number of versions of each module that must be kept) and can lead to some human versioning errors.

f) What kind of information should I add to version control?

There are different approaches: Everything (hand-made code, generated files, documentation, even compiled exec file or DLLs), some of the above etc. In general, documentation should be added if no additional design repository exists, otherwise, use the repository, which usually has a versioning capability. Adding binary files will usually have to be considered during the initial setup phase, as this requires significantly more memory and not all tools can handle binary files in a correct manner.

g) Which stages to add?

The stages in the version control (Dev, Assembly test, system test, etc.) should be added according to the development approach. Strong relationship to migration control. Should also be automated and is usually supported by the tools.

Product Considerations a) Does the tool provide capabilities to cater for a system running on multiple platforms or a distributed system?

Ideally, the Version Control tool must be able to operate on all the platforms in use, whilst at the same time performing Version Control for all components across the entire system.

b) Does the tool provide support for actions like mass builds?

Usually, custom tools are put on top of the vendors tools to support actions like mass builds etc. Some tools (or add-ons) support this already. This is vital for the project, as it allows huge productivity gains in later phases of the project.

c) How easy is it to implement batch solutions?

It should be considered if a batch/API interface exists for implementing batch solutions.

Change Control (818)

The Change Control system should provide the following features:

Free format description of changes

Classification of changes in several different ways (area affected, priority, estimated cost, authorization)

Flexible, customizable sorting and reporting to ensure that a change is handled in a timely manner Ideally, the Change Control system should also be integrated with workflow support, the repository, and the source code control system. This ensures rapid processing of the change, accurate analysis of the area affected, and correct locking and unlocking of repository objects and source modules.

Implementation Considerations a) Does the project require strict scope control?

Specifications and scope may be changed at any time if Change Control tools and standards are not implemented. This can result in the project running over budget, or being delivered late with inconsistent quality because requirements change continuously.

b) Is the system complex?

Change control has broader applicability than to just application source code. It may also affect the look and feel, training materials, documentation, and so forth. Change Control must be formalized if the system is complex with many components.

c) Do changes need to be authorized by specific personnel?

Change control tools provide a vehicle for ensuring that only authorized changes are made and signed off. This ensures conceptual, proper ownership of the total look and feel of the application. Change requests may also be rejected or deferred by an authorized person.

d) Is coordination of changes required?

Facilities to track interdependencies between change requests (for example, change request A must be completed before change request B can start) are provided by Change Control tools. This can be used to encourage efficient scheduling and to ensure that work is not duplicated.

e) Should a record be kept of changes that fall beyond the capacity of the project at that time?

Change Control tools can provide a vehicle for capturing good ideas. If the project does not have the capacity to implement those ideas at present, the Change Control tool can be used to capture those ideas. These ideas can be reinvestigated when a future release is planned.

f) Are conflicting change requests likely to occur?

Change request tools can be used to identify changes that conflict, for example, one user wants a green background and another wants a blue background. The changes must be resolved through some kind of dialog or discussion and Change Control can be used to initiate this process.

g) Is it likely that the system will need to be rolled back to a certain state?

This is typically the case when the project is breaking ground by using new techniques or untried architectures.

Change control tools provide a means of identifying at what point in time a critical change was implemented and that information can be used to find out what version existed at that time.

h) Is there a need to evaluate the impact of implementing a change on the project?

Change control tools typically support some kind of impact analysis and may be integrated with an impact analysis tool set. Impact analysis is important in order to group changes so that they can be implemented effectively.

Multiple changes may affect the same component and it would be wasteful to open that component many times over and implement the changes one at a time. Impact analysis can be used to ensure that all relevant changes to that component are implemented together. Hence impact analysis is important for scheduling purposes and for estimating cost.

Product Considerations a) Does the tool provide a capability to classify change requests?

Change requests may occur as a consequence of changing requirements, or as a result of nonconformities (or defects) in the system. The tool should be able to classify change requests into categories such as incidents, faults, or enhancements. The tool should also have the ability to update these categories if required. Classification of different change requests in several different ways such as area affected, priority, estimated cost or authorization is important to ensure correct scheduling of the implementation of changes. Flexible, customized sorting and reporting based on this classification is required to ensure that change is handled in a timely manner.

b) Should an Impact Analysis tool be purchased or developed?

Impact analysis tools are typically required to provide analysis of a wide range of types of documents such as Word, Excel, or PowerPoint.

If an impact analysis tool cannot be found that supports the entire environment, it is critical to develop procedures or utilities that will report on where items are used. The first step is to identify the items to be searched, and to build procedures around searching them (for example, databases, files, workspaces, programs, screens/forms, reports). It is also important to identify who will be responsible for the impact analysis (DBA, analysts, programmers, team leaders, and so on) to avoid this work falling between the cracks.

c) Does the tool provide free format description of changes?

Free format descriptions are important because this allows better and more understandable documentation of change requests and associated decisions.

d) Are there going to be multiple releases of the software?

The tool should allocate change requests to different releases based on priority and resource availability. It should also provide a means of attaching a deadline to a change request.

Does the tool provide a means of indicating which development team member is best suited to perform the implementation of that change request?

This functionality should be available as part of the scheduling capability. An added feature would be the capability to balance workload across the team.

e) How does the tool handle exceptions?

The tool should provide a capability to generate exception reports that highlight issues such as change requests that are in danger of not meeting the release to which it was allocated.

f) What is the prediction for volume of change requests for the project?

The tool should be able to cope with the expected volume of change.

g) Is validation of data entered into the change request form a consideration?

It may be necessary to ensure that the data entered on a change request form is valid. This is particularly important if the development team is inexperienced or if the project is particularly complex. An example of data validation would be to ensure that the change is assigned to a valid team to prevent a change request from falling through the cracks.

h) Is recording of resolution details and root causes required?

This capability provides useful tracking across the complete life cycle of a change request.

i) What reporting capabilities are needed on the project?

Some Change Control tools can report on status of change requests at the individual, team, and project level. Such reports can provide information about work done to date and Estimate to Complete (ETC) values.

j) How many users will simultaneously be accessing the system?

The tool should cater to the size of the project. Maintaining consistency of information may otherwise become a problem with simultaneous access. The tool should provide some kind of protection of change requests if simultaneous access is likely to occur.

k) Does the tool provide a means of prioritizing change requests?

The tool should provide capabilities for prioritizing change requests based on business impact and the impact of implementing the change.

Does the tool provide capabilities for predicting the cost, risk, and instabilities created as a result of implementing a change request?

These capabilities need not provide completely automated prediction but should work in conjunction with an analyst.

l) Does the tool identify component dependencies?

This is an important aspect of impact analysis that is required to ensure that all components impacted by a change request are identified.

Migration Control (816)

Migration Control tools control multiple versions of source code, data, and other items as they are changed, tested, and moved from one development environment into another, for example, from development to test and from test to production. Data migration control tools manage multiple versions of the database and its data to ensure that accurate data and structure are maintained in the environment, and to ensure that versions of application code and database are deployed consistently. Types of data that would be migrated include base codes data and converted data. Other Migration Control tools manage other types of objects to ensure that complete versions of all components reside in the production environment (for example, test definitions and scripts).

Implementation Considerations a) Are there multiple environments running in parallel?

Multiple environments are typically required when the project is faced with serious time constraints. Typically the project team performs integration or systems testing on one portion of the system, while developing the next portion. The team corrects errors based on one test while at the same time, the next test cycle or testing of the next part of the system is performed. This means that multiple environments exist that are configured differently and use a different version of the system components. The migration of these different versions and configurations between environments must be carefully controlled using Migration Control tools. For successful migration there must be consistent migration of all components and their dependents.

b) Are multiple releases being developed in parallel?

If multiple releases are being developed in parallel, it is vital to provide a consistent means of migrating configurations and versions from one environment to the next. This ensures that there is no confusion of components in each release as the move is made from, for example, a unit test environment to a system test environment.

c) Is the development effort to be sustained over a prolonged period?

Migration control tools keep a log of what is migrated. It may be required to review what has happened over time, in order to gain an understanding of the current status of the system.

d) Is there a need to control who activates migration from one environment to the next?

Migration control tools ensure that only authorized personnel can trigger the migration of components from one environment to the next.

e) Is the system complex (consisting of more than 1000 components)?

The task of promoting components and locking these components to prevent concurrent or unauthorized updates to them or their dependents becomes very intricate as the number of components reaches 1000. Migration control tools can be used to improve productivity by facilitating and controlling the migration from one environment to another and by automating the process. It is possible to bring a large project to a complete halt if Migration Control is not properly enforced.

Product Considerations a) Does the tool support the migration of all the components that make up a migration object?

The Migration Control tool should be able to manage and control the migration of all the components (for example, source code, database access, make files, run-time data, environment variables, code libraries, code tables, third-party software, and so forth) which make up the object to be migrated. The complexity of the Netcentric world with so many integrated vendor solutions dramatically increases the number and variations of object types.

b) Does the tool facilitate the migration of many components together as well as migrating components individually?

Migration from a development environment to a system test environment either involves a large number of components (migration of all the components belonging to a test cycle) or single components (after code fixing in a program). Either way the Migration Control tool should lock the migrated component to control changes and allow better coordination with the system test team.

c) Does the tool support all the required platforms?

In a development environment where there may be different platforms, it is important that the Migration Control tools be able to synchronize source migration across platforms. Unit and system tests are normally performed on every platform so the migration tool should be able to promote the components across platforms as well as from environment to environment.

d) What is the migration strategy?

A push strategy should be facilitated by the migration tool if it is decided that modules should be tested when those modules are ready for testing. This is normally the case for unit testing. A pull strategy is needed if the order of component testing is important as is normally the case for system testing. In implementing a push strategy it is usual for the individual programmer to be responsible for migrating the module. If this is the case then the tool should be easy to learn and use. Using a pull strategy may decrease the number of people required to know how to use the tool.

Release Management

Release Management tools should provide:

Planning functionalities, to help planning design and development effort

Monitoring functionalities, in order to measure progress towards delivery goals

Project interdependencies management

Interface with the change control system

Ideally, the Release Management system should also be integrated with workflow support, the repository, and the project/program management system.

Environment Management (906)

The modern development environment is both complex and sophisticated. It supports many different functional and technical requirements (illustrated by the execution architecture), many different development teams, tools from many different product vendors, and often must support projects at different stages of the development life cycle. As such, it is a mission-critical production environment and must be managed based upon an operations architecture. The extent to which the areas of the operations architecture are implemented must also be a factor of project size and duration.

The environment management requirements in this section are based upon the MODE (Management of Distributed Environments) conceptual framework. This section uses MODE as a framework, adopts MODE terminology, and focuses on those management tasks from MODE which are particularly important in the development architecture.

MODE identifies four main areas:

Service Management

Systems Management

Managing Change

Service Planning

The subcomponents of Environment management reflect these four MODE areas.

Service Management (822)

Service Management tools support the various aspects of supporting and managing the interface with developers. As defined in MODE, these include the following:

Tools to support and manage the Help Desk

Tools to support the creation, management, and reporting of Service Level Agreements (SLAs) and Operations Level Agreements (OLAs)

Tools to manage and support the quality of the development environment

Systems Management (826)

Systems Management Tools support and manage the operation of the distributed system.

Startup & Shutdown

A comprehensive development environment rapidly becomes sufficiently complex that the startup and shutdown of the environment must be managed carefully, and preferably automated. This is key to ensuring the integrity of the environment. Startup may involve the carefully sequenced initialization of networking software, databases, web servers and more. Similarly, shutdown involves saving configuration changes as needed and gracefully taking down running software in the correct sequence.

Backup & Restore

The incremental value of the daily work performed on the development project is high. This investment must be protected from problems arising from hardware and software failure, and from erroneous user actions and catastrophes such as fires or floods. The repositories and other development information must therefore be backed up regularly. Backup and restore procedures and tools must be tested to ensure that system components can be recovered as anticipated. The large volumes of complex data generally require automation of backups and restores.

The advent of Netcentric technologies has introduced an increase in media content that requires storage (see Processes—Information Management—Media Content Management). The environment may support a high volume of media files, which must be considered in the backup/restore plans. Storage capacity planning should allow for the typically increased size of these file types.

As the amount of storage will grow significantly over time on a large project, the hardware requirements will increase. Sufficient room for growth should be planned when selecting the tools and hardware. Switching tools and hardware can be problematic due to lack of upward compatibility (DDS—DLT, various tools etc.).

The time required for backups must also be considered. Usually the number of hours without development per day decreases over time and if backups can only be performed when no user is logged in, this might become a problem. It is generally the case that the project will benefit from buying the fastest and largest backup hardware/software it can afford.

Archiving

Archiving can be particularly useful to safeguard information from previous versions or releases. More generally, it is used to create a copy of information that is less time-critical than the current environment at a given time. Archiving may be performed to a medium, which is different from the backup medium, and may involve other tools which, for example, provide a higher compression ratio.

Security

Security tools are required in the development environment to ensure against unauthorized access by individuals and system processes, to limit damages caused by such unauthorized access, and to audit access the environment services. At the security management level, it may be valuable to have tools which help manage security profiles, security groups, and access rights.

Product Considerations a) Does the tool use Role-based access control?

Role-based access control establishes access rights and profiles based on job functions within the environment. If different access rights are required for security administrators vs. code developers vs. code reviewers vs. testers, then the correct access can be established based on these functions.

b) Does the tool have flexible auditing capabilities?

The security administrator should be able to granularly configure what is being audited by the tool. The audit logs should be able to optionally record User ID, time-of-day, location of access, successful and unsuccessful access or change attempts, etc.

c) What are the performance implications of the tool?

Some security services, such as content scanning or auditing, may add noticeable processing time and requirements to the system. Tools should be architectured in such a way that performance impacts are or can be configured to be minimal.

Performance Monitoring

Performance Monitoring tools help ensure that the available resources are sufficient to meet the developers' performance requirements. These tools can be used to assess end-to-end performance of both batch processes such as backups, and interactive processes such as repository-based file retrieval.

Service Planning (824)

Service Planning is the planning required to anticipate and implement changes to the following areas:
- Service management
- Systems management
- Managing change
- Strategic planning All these areas relate to the development environment and are analogous to the kind of planning that must occur in the business application's production environment. Key types of tools for development environments include Performance Modeling and Capacity Planning tools.

Performance Modeling

Performance modeling tools in this category support the analysis of the development environment's performance, as opposed to that of the client/server application being developed. A simple spreadsheet may be suitable in some well-known and understood environments, but dedicated performance modeling tools should be considered on any project with high transaction volumes or complex environments involving multiple platforms.

Capacity Modeling

Capacity modeling tools support the maintenance of adequate processing capacity for the development environment (for example, workstations, servers, storage devices, and network capacity). These tools range from spreadsheets to dedicated capacity modeling and simulation tools.

Managing Change (820)

Managing Change tools support the various aspects of identifying and managing change in the development environment. Specific tools are discussed in detail in the MODE Products Database on the Knowledge Xchange.

Data and Software Distribution is a key tool in this category for development environments that have several developers. These tools enable automated distribution of data and software to the workstations and servers in the development environment.

Problem Management (912)

Problem Management tools help track each system investigation request—from detection and documentation to resolution (for example, Problem Tracking, Impact Analysis, Statistical Analysis).

Problem Management tools log information about problems detected, classify them, and generate reports. This is essential for capturing metrics information.

The major functions of Problem Management are:
- Problem source and metrics information
- Problem solution information
- Planning support for problem fixing and migration preparation
- Impact analysis capability:
  - Link to the application design repository to get a precise impact analysis on a problem
  - Link to the test plan management system to keep track of the cycle and test the condition where the problem occurred, to determine the test stage work unit affected by the problem It is important to select an automated Problem Management system that is integrated with the program's testing and Configuration Management tools. Therefore, the Problem Management system must be able to support the testing model selected, for example, the V-model, and have tight integration with the Migration and Version Control tools associated with Configuration Management.

An automated test script tool can be integrated to allow users to reference scripts that were being used when the error or defect was found. A data repository can be integrated into the Problem Management application that will allow the users to build relationships between problems and design and test documentation and application components.

An ability to associate problems with affected work packages and a mechanism for version control changes for the work package is necessary so the package can be migrated back into the testing environment.

When considering an automated tool, also consider what type of security is required for the Problem Management application. This is closely tied with the Configuration Management tools. Only one person should have the rights to review and approve problem analysis tasks as well as problem migration activities.

Implementation Considerations a) How are problems handled at each stage?

b) How do I plan for trapping problems?

c) Do I retest problems at different stages?

The following is an overview stage containment as documented by the Reinventing Testing Project (RTP).

Stage containment is an approach to identify problems in the system before they pass to the next stage. It is a measure that helps build quality into the system. The goal of stage containment is to minimize the number of errors being passed to the next stage. For the purpose of stage containment, problems are sorted into categories. Errors are defined as problems found in the stage where they were created. Defects are problems found in a stage successive to the stage where they were created. Faults are problems found in production. The longer a defect remains undiscovered, the more difficult and expensive it will be to correct. Because each stage relies on the decisions made during the creation of the specification in the previous stage, detecting an error in a stage after it was made may invalidate some or all of the work done between the time the issue was created and the time it was discovered.

The V-model specifies that testing in one stage must be completed before moving on to the next stage of testing. Before moving up to the next stage, it is key that the exit criteria defined for that stage have been met. A part of the exit criteria for each stage is that the test has been successfully executed, therefore ensuring the test objectives (or primary focus of the test) are accomplished before moving on to the next stage.

Once the objectives of one test stage are met, there is no need to repeat the same testing at the next stage. This is a key concept of the V-model and one that proves difficult to accept and use in practice. There is often a desire to retest just to "make sure everything is OK." Doing so, inevitably leads to time-consuming testing. In addition, it leaves less time to do the testing required for the current stage of testing, ultimately resulting in minimal, if any, time for the last stage of testing. In other words, minimize gaps and overlaps between the testing stages while ensuring quality of delivery.

It is possible, however, that testing at one stage may, and should, use test scripts from previous stages. Two stages of testing may be executed together, using the same scripts, but both sets of test conditions must be covered (that is, both sets of objectives must be met). All stages of testing are required. For example, a thorough assembly test cannot make up for inadequate component testing, as the objectives of each test stage are different.

d) What other components does the Problem Management system interface with?

RTP has identified the following components as interfaces with the Problem Management system.

Configuration Management—When a defect is ready for migration, the Migration Control system can be used to pass the list of components to migrate. The Problem Management system can keep track of the migration date obtained from the Migration Control system.

Design Repository—An impact analysis of a specific component in error will be performed directly on the design repository by providing a means to use the appropriate design repository function or having the Problem Management system referencing the design repository objects.

Test Data Management—Test results, expected results, and data comparison results can be linked to a defect to provide centralized access to the information.

Integration also aids in keeping track of the cycle where the problem occurred, the test condition, and therefore the business function affected by the problem.

e) How many design repositories should be used?

f) What does the design repository interact with?

Typically, the design repository represents the basis of the application development. It is mainly involved during the construction phase of the application and is used to centralize the application definition data. The design repository can be complex, providing impact analysis and application generation features.

In a testing environment, the design repository is a safe means of analyzing the impact of a problem on the whole application.

Having two separated systems, one for Problem Management and one for application design, duplicates the information and introduces errors. Therefore, the interaction between the design repository and the Problem Management, Test Planning, and Configuration Management components significantly increases productivity and reduces the risk of errors.

Product Considerations a) Are there any Problem Management tools identified?

Problem Management tools log error information, generate error reports (such as System Investigation Reports or SIRs), classify problems, and record information on the source of the error. Problem Management tools are essential for the capture of stage containment metric information.

b) What engagement factors affect the use of problem Management tools?

Risk rating of the engagement—In general, management and planning tools help better address the engagement risks. A high risk rating for the engagement affects positively the decision to use tools such as Test Planning, Test Data Management, Problem Management, and Configuration Management.

Criticality of the engagement—In general, management and planning tools help better manage the engagement and ensure the timely delivery of a quality system. Therefore, dealing with a highly critical engagement will most likely affect positively the decision to use tools such as Test Planning, Test Data Management, Problem Management, and Configuration Management.

What testing team factors should be considered when using a Problem Management tool? Communication between development team and testing team—A Problem Management tool can be used to track issues, design changes, and so on, and serve as a communication tool between teams. As part of a Change Control mechanism for the engagement, such a tool can help improve communication between the development and testing teams. Thus, bad communications between teams can still have a positive influence on the decision to use Problem Management.

Size of the testing team—The size of the testing team has an impact on the decision to use a Problem Management tool. If the testing team is large, keeping all team members informed on the status of identified problems is a more complex endeavor than with a small team. The larger the testing team, the more benefits will be derived from using a Problem Management tool to support testing.

Similarly, the larger the testing team, the more benefits will be derived from using a Test Data Management tool (easier control over the test data for the various testers), a Configuration Management tool (easier control over all system configurations and component versions) and a Test Plan Management tool (easier control over all test cycles, subcycles, their execution statuses, and so on).

System Building (918)

System Building tools comprise the core of the development architecture and are used to design, build, and test the system. All the system building tools must be integrated and share development objects appropriately.

Analysis & Design (828)

Analysis tools are used to specify the requirements for the system being developed. They are typically modeling and diagramming tools, which provide the ability to diagram system requirements and specify "what" a system must do.

Design tools are used to specify "how" a system will implement these system requirements. They are typically diagramming tools, which graphically depict how the system will be built in terms of its key components. This differs between classical client/server systems and component-based systems:

The standard client/server model comprises application logic, presentation, and communication components, which together support the business processes. For a client/server system, each of these components must be individually defined.

The component-based systems, however, have the data model and process models encapsulated within the object model. In addition, the design of the component model is directly affected by the business processes which govern the way these objects interact. Therefore, with component-based systems, the object and component models encapsulate the data and process models.

Data Modeling

Data Modeling tools provide a graphical depiction of the logical data requirements for the system. These tools usually support diagramming entities, relationships, and attributes of the business being modeled on an Entity-Relationship Diagram (ERD).

As systems are often built on top of legacy databases, some data modeling tools allow generation of an object model from the legacy database data model (DDL). By understanding the E-R diagram represented by the database, it is easier to create an efficient persistence framework which isolates business components from a direct access to relational databases. Caution is required, however, as the resulting model is at best only partial, as an object model has dynamic aspects to it as well as static relationships, and may not correctly reflect the analysis performed in the problem domain.

When a component or object-based approach is used, data modeling is not performed. Rather, the object model contains both the data and the behavior associated with an object. In most systems relational databases are used and the object model must be mapped to the data model. Standard mechanisms for mapping objects exist. Tools such as Persistence (Persistence Corp.) and DBTools (Rogue Wave) can generate the code necessary to map objects to a database.

Implementation Considerations a) Can the development process benefit from a DDL generation tool?

Data modeling tools allow DDL to be generated from the data model. The tools should support DDL generation for the chosen RDBMs (Sybase®, Oracle®, DB2®). In addition, the DDL generator should take advantage of the specific advanced features supported by each of the RDBMs.

b) Can developers benefit by a graphical depiction of the logical and physical data requirements?

Data modeling tools help to graphically develop the logical and physical data requirements for an application. These tools depict logical constructs such as entities, attributes, and relationships between entities, along with physical constructs such as database definitions and table indices.

It is useful for developers to have read-only access to either a hard or soft copy of the data model during development. This document rapidly becomes a key discussion document in design discussions. It is useful to show tables, columns, primary keys, and foreign keys (if all of this will fit on a diagram at the same time!) in the document Graphical depiction is not only useful but essential to data architects, DBAs and also to application developers (the latter group is often omitted). As in most cases, a picture speaks a thousand words.

c) Is there a need for consistency in data across applications?

Data modeling tools promote consistency in application development by defining standard names and attribute characteristics for the application data. Application developers then use the standard entity and attribute definitions across various application development initiatives. This results in a consistent definition and usage of data. For example, all applications that require customer number will use the standard name and attribute length defined in the data model. Database administrators will also use the data model to generate physical database definitions that are consistent with the application under development. Thus, the data model acts as a single source for data definition.

All applications should have data consistency that is linked back to a set of business data standards. Failure to achieve an agreed set of definitions will jeopardize the ability of the separate applications to perform as a business unit, for example, applications will not be able to share data if they are in different formats or use different code lookups. Data consistency must be agreed FUNCTIONALLY during analysis and design. Data modeling tools will help to document data definitions but they will not automatically enforce data consistency.

d) Are there more than 100 entities in the data model?

At this level of complexity a dedicated data modeling tool is necessary.

Does the system incorporate object oriented methods?

Is a relational database being used to store persistent objects?

Fully normalized data models are a different view of the corresponding object models. On the one hand, the data model does not show behaviors (methods). On the other hand it does show resolving entities that are normally modeled as container objects and may be internal to an object. A data modeling tool is useful for showing how the persistent objects map to the relational database.

e) Is there a need to communicate the business data requirements without regard to the DBMS or platform?

A data model is a technology-independent model of an organization's data requirements consisting of diagrams and descriptions of entity types, attribute types, relationship types, and integrity constraints. It is a flexible, non-redundant, non-constraining model. As a simplified representation of reality, it has no regard for such physical matters as how data is to be retrieved or how long it will take. The data model presents a concept of the business data in an idealized structure. It is a useful tool to communicate the scope of the project.

f) Is the system complex and changing?

Good data modeling requires a full understanding of the business data involved. Data modeling becomes more important as systems become more complex and sophisticated. The data structures which support such systems must be flexible and be able to accommodate change. The data model is the best means of identifying and representing these changes.

g) Is database design going to be performed?

The finalized data model is used as a basis for the logical database design. The logical database design converts the finalized Project Data Model to one of four basic structures, according to which DBMS is used:

Hierarchical (rarely used today)
Network (e.g., IDMS)
Relational (e.g., DB2)
Inverted List (e.g., ADABAS)

Although entity-relationship diagrams are independent of specific DBMSs or access methods, a logical database design is not. This design is highly dependent on the platform components and may need to be repeated for each location type and platform type. This process is simplified if a data model is used.

h) Does the system interface with external systems having their own data definitions?

Data modeling tools allow documentation of the data in so far as it appears in the data model (and ultimately in the database). However, there is usually a significant number of other data definitions which will never appear in the database, and whose definition is different to the data model attributes. For example, most systems have interfaces to external systems, and inherit a legacy of interface files whose data definitions may differ to those on the data model, but which do logically correspond to fields on the model. These data definitions must also be documented and stored but are effectively outside the data model. The data modeling component should be used to implement procedures to address all the data definitions that affect the system.

Product Considerations a) What is the intended use of the tool?

The features required in the data modeling tool will depend on the intended use of the tool. If the tool is to be used to develop logical data models, it should support logical constructs such as entity definition, attribute definition, subtyping, and supertyping. If the tool is to be used for physical data design, it should support the physical constructs required for the targeted RDBMs, such as transforming a logical model into a physical model, database definition, index definition, and DDL generation.

b) Does an existing component satisfy this requirement?

The development architecture may already have tools that support data modeling. For example, many information management tools (repository) provide data modeling capabilities. Using a single tool for multiple functions reduces the developer learning curve and provides integration between the components of the development architecture.

c) What other utilities are available with the data modeling tool?

It is important to consider the various utilities available with the data modeling tools. Two such utilities include impact analysis and reporting.

Impact analysis capabilities allow the user to understand the impact of a change to the data model. Impact analysis functionality is one of the key tools used by engagement teams to assist with change management and change control activities. Some products will also include report generators which are useful for generating data and attribute definition reports as well as ad hoc reports.

d) Does the development team have any prior experience with data modeling tools?

A data modeling tool may be chosen based upon prior experience with the tool by the client or members of the engagement team. This reduces the learning curve associated with integrating a new tool into the development environment.

e) How well does the data modeling tool integrate with other development tools?

Data modeling tools commonly integrate with the repository and with system building tools such as window painters and Application Logic Design tools. If the tool does not provide seamless integration with other components of the development environment, the engagement team can build bridges between components, or develop manual procedures in order to share information.

It is important to consider how the data modeling tool integrates with the design repository. It is important to maintain a cross-reference of the attributes on the model, with the definition of data elements in the design repository. Such data element definitions will also address non-database data definitions (e.g. external i/face files).

f) What level of data modeling is required?

During the early conceptual design, data modeling need not be very detailed. It should be a participative, team activity, and is usually very unstable. In this case, a tool such as a white board or PowerPoint will suffice.

As the design becomes more detailed, more sophisticated tools are needed. At the lowest level of detail consistency is vital and a repository-based tool can be used to ensure consistency across the data model.

g) Should the data modeling tool provide database design facilities?

There are some tools which do not incorporate this feature, such as ARIS, which is strictly a data modeling tool. This may be helpful to guard against moving too far into the design during the analysis phase.

Most data modeling tools allow you to develop the database design at the same time. This has the advantage of keeping costs down as two separate tools need not be purchased, and of ensuring consistency by providing a direct interface between the two phases.

h) Does the data modeling tool support submodeling?

Submodeling enables complex models to be broken down into smaller more manageable and understandable models while still maintaining unique object definition. This is particularly important for large teams where data modeling is divided among several teams.

i) Does the data modeling tool provide support for a multi-designer environment?

The information management component may provide the security needed in a multi-designer environment. If this is not the case then a multi-designer data modeling tool should be used. The tool may provide a central dictionary which allows design data to be shared between several designers and includes security checks to monitor any conflicts in overlapping access rights between designers.

j) Does the tool provide facilities to add color to the data model?

The facility to add color to the data model is useful for communicating additional dimensions such as data ownership.

k) Is entity life history required to be documented?

The data modeling tools must support a facility for ELH modeling for entities that have their status changed by a wide range of events. Any entity which has an attribute containing the word status is a likely candidate.

l) At what point should inconsistencies in the design be controlled?

Designs should be consistent. However, enforcing internal consistency at all times can lead to design gridlock which prevents innovation or progress. The tool should support the project decisions regarding consistency.

Process Modeling

Process modeling tools provide a graphical depiction of the business functions and processes being supported by a system. The tool(s) selected must support the modeling techniques being used in the development methodology. These include process decomposition, data flow, and process dependency.

Implementation Considerations a) Are the processes that the system is to support ill-understood or is there little consensus on what these processes are?

Process modeling is a method for clarifying and communicating the business design of the system. The process model can provide an effective means of bringing people together, creating a shared vision of how the business is to function.

b) Do the processes vary from region to region and need to be standardized?

A process model provides a means of standardizing a set of similar processes which exist, for example, at different branches of the business.

c) Does the project include process re-engineering or process-streamlining?

The re-engineered processes in the process model may form a basis for the systems design which is to come afterwards. Requirements and constraints for the system design can be well represented and communicated in a process model.

d) Is process simulation required?

Advanced process modeling tools provide process simulation capabilities. Process simulation ensures that the process design is adequate as a basis of the functionality of the software that is to be developed.

Product Considerations a) What approach is to be used for process modeling?

The tool may need to support the creation of business function decompositions or data flow diagrams depending on the approach used.

Data flow diagramming is used when the application has a complex or innovative workflow or if the analysis and design teams have little experience with the application.

Business function decomposition is used when the application is fairly routine and the team has extensive experience with similar applications.

b) Does another component support procedure diagramming?

A business function decomposition diagram can be produced using a procedure diagramer.

c) Are common process symbols to be reused?

The tool should provide a facility to create custom symbols for the process flow and these should be reusable.

d) Does the tool support the expected size of the process model?

The process model may include hundreds or even thousands of processes. The tool should be able to support the expected size of the process model.

e) Does the data flow diagramer support leveling of diagrams?

Some tools allow leveling of the diagram in which a process box on a high level diagram is decomposed into multiple processes on a lower-level diagram. To ensure that the diagrams are easy to understand and that they easily convey information, it is useful to keep the diagram size to one window or one printed page. The facility to level a large diagram can help to achieve this.

f) How does the data flow diagramer support data stores that are used by more than one process?

It is often the case that processes that share a data store cannot be placed near each other on the diagram. To avoid complicating the diagram, some tools allow data stores to be depicted more than once on the diagram. The tools may provide facilities to differentiate these stores from stores that have not been duplicated in this manner.

g) Can control flows be represented by the data flow diagramer?

It may be necessary to depict control flows. The tool may represent these as data flows without any data elements, such as, for example, a signal from a timer function.

h) Does the tool support validation of the diagram?.

To ensure that a data flow diagram is complete, each process should have at least one input and one output. Unless data stores are shared with other systems, each attribute of each data store must have at least one input flow associated with it. The tool should facilitate the identification of exceptions to these general rules.

i) Is a detailed process model with complex processes to be documented?

At the lowest level of a data flow diagram or a business function decomposition, there may be processes that are still too complex to be explained by a label or even a short paragraph. For example, this may be the case if complex interest rate calculations are to be performed by the process. An elementary process description may be required for each such process. The process modeling component should include tools that enable the description to be documented. The description may be formatted as plain English, structured English (resembling pseudo-code), decision tables, or as action diagrams.

Event Modeling

Event modeling tools provide graphical depiction of the events and associated responses for the system. A variety of tools and techniques can be used for event modeling, for example, word processors to develop simple textual lists of events and data flow diagramming to show events and responses.

For component-based development, event modeling or interaction sequence modeling may be performed through interaction diagrams, both at the object and component level. The event model is often used as input for test scripting.

Implementation Considerations a) Is there a need to capture the essence of how the business functions without becoming tangled in the current sequence of processes?

Event modeling does not fix the sequence of processes. A process starts when a specified event occurs, and may generate other events when it has finished. Event modeling notation allows focus on what steps the process must do as opposed to "how" it sequences the steps. This form of representation is especially useful for processes that will be re-engineered, since it allows steps to be re-arranged easily.

b) Is there some uncertainty about the functional requirements or scope of the system?

An event model represents external actions which the system must recognize and responses which the system must produce. Events express the system's perception of external activities. Therefore, event modeling allows the external environment to influence the requirements definition, rather than basing the environment on the applications structure. This approach supports the applications consistency with the workflow and other business activities and thus clearly defines the scope of the system.

c) Are the business requirements of the system to be communicated to a large team or to the users?

An event model represents the user requirements in concise business terms. When used in conjunction with the process model, this provides an effective means of communicating the system requirements from the business design team to the systems design team or to the users.

d) Does the architecture have several disjoint systems that need to respond to the same business event?

By using event modeling and a central event router architecture, interfaces to several systems can be easily and flexibly provided. Each system registers itself with the event router and indicates which business events it is interested in. Whenever an event is triggered, the router is notified. It then triggers all the applications that registered themselves as being interested in that event.

Applications can generate events as required to ensure that appropriate next steps in the process are performed after they have completed their part.

e) Is a real-time system to be developed?

Real-time systems require very strict responses to events within specified time frames. Event modeling is critical to ensure that real-time systems meet this requirement.

f) Is the extent of change to the business particularly large such that a detailed requirements model is needed?

The requirements model (event, process, and data models) provides a clear means of depicting the system. The requirements model summarizes the relationship between events, data, and processes. It consists of the event model, the process model, and the data model. The event model is important because it details the business transactions and events enough to understand the process and data models. Event modeling tools must be provided to complete the requirements model.

Product Considerations a) Do other tools provide the required functionality?

Event modeling and process modeling go hand in hand and are typically provided by the same tool.

b) Are events triggered by time easy to represent?

The modeling tools chosen should provide a means of clearly depicting events that are triggered by time e.g. the year end event.

c) Does an existing component provide all the necessary facilities?

A flow charter is generally required to graphically depict the events. There is also a text description of the events which can be documented using a tool such as MS Word® or MS PowerPoint®. Entity life cycle diagrams, Event-Stimulus-Response diagrams or matrices, or Context diagrams may be required to complete the model.

d) Is the system complex?

As the number of events increases, the complexity of the event model increases and the diagramers may need to support certain facilities such as intelligent connectors. Simple graphics packages may not suffice at this level.

Performance Modeling

The performance of a system must be analyzed as early as possible in the development process. Performance modeling tools support the analysis of performance over the network. A simple spreadsheet may be suitable in some well-known and understood environments, but dedicated performance modeling tools should be considered on any project with high transaction volumes or complex distributed architectures involving several platforms.

In the case of Internet-based applications, as the Internet is not a controlled environment, performance modeling is limited to those components within the domain of the controlled environment (i.e. up to the Internet Service Provider). However, In the case of intranet-based systems, where the environment is controlled from end-to-end, performance modeling may be performed across the entire system.

Performance modeling for components involves the analysis of the projected level of interaction between components and the level of network traffic generated by this interaction. It is important for performance reasons that communication between components is minimized, especially if these components are distributed.

Implementation Considerations a) Is the system complex or heterogeneous?

A performance model ensures that performance requirements are met in a complex or heterogeneous environment. Performance is usually a critical quality requirement in such environments.

b) Does the system involve extensive communication over a Wide Area Network?

The complexity involved in designing systems over a WAN makes performance modeling tools critical to success for such systems.

c) Are there hundreds of users? Are there tens of servers?

Due to the complexity of such systems, performance modeling tools are important in ensuring performance requirements are met.

d) Do experience and benchmarks indicate that there may be difficulties in meeting the performance requirements as stated for the system?

In this case performance modeling tools are critical, since penalties may be incurred if the system does not meet the performance requirements. A performance model provides a means of deciding early on whether the system is feasible or not.

e) Is what if analysis required for future growth?

f) Is what if analysis required for alternative hardware configurations?

g) Is what if analysis required for hardware loading?

Performance modeling tools provide a means of analyzing how much future growth or what alternative hardware configurations can be sustained before the system breaks down. This component may be needed even though it is obvious that the system will meet the current performance requirements.

h) Are high transaction volumes or complex architectures expected for the system?

Dedicated performance modeling tools should be considered for any project that involves high transaction volumes or a complex architecture with several platforms. Performance is critical for such systems and a performance model is required in order to predict and optimize that performance.

Product Considerations a) Does a generic tool such as a spreadsheet package suffice as a performance modeling tool?

A specialized performance modeling tool should be used when the system is complex and involves high volumes of data, or is heterogeneous.

As design progresses from high level conceptual design to detailed design, to technical design, there is a corresponding sequence of activities involved in performance modeling. As the design becomes more detailed, so does the performance model. The model may start as a simple spreadsheet and evolve into a collection of spreadsheets with many sheets in each book. As the structure and parameters become overwhelmingly complex, a dedicated modeling tool with its own data model, user interface etc. is a good investment.

A performance modeling tool should not be purchased due to a lack of understanding or inexperience of performance modeling, since the tool will not clarify the issues any more than a spreadsheet model.

b) Does the tool allow empirical data to be fed back into the performance model?

Performance modeling must be backed up with empirical data at the earliest possible stage. Initially, this will be through performance benchmarking usually using a small equivalent of the production system. The results should be fed back into the performance models to improve their accuracy. There should be a means of differentiating empirical data from estimates in the model.

Object Modeling

An object model usually contains the following deliverables:

Class Diagram (1 per functional area or 1 per component)

Class Definition (1 per class)

Class Interaction or Sequence Diagram (1 or more per scenario/workflow)

Class State Transition Diagram (1 per Class with complex state)

Specific modeling tools can provide advantages such as cross referencing (for example, are all the methods used in the Interaction diagrams described in the class definitions?), automatic propagation of changes to other diagrams, generation of reports, and generation of skeleton code. However, some tools have problems with:

Usability and stability

Single users or small numbers of concurrent users

Proprietary repositories (usually file-based, rather than DB-based)

Support of extensions/customizations

As well as providing the usual editing and graphical functionalities, a good modeling tool should:

Interface with a repository (to support versioning)

Support multiple users

Generate code from the design

The use of UML notation to represent the object model is becoming more and more common. In this case other diagrams such as Use Cases and Collaborations Diagrams complement the model.

Component Modeling

Component modeling can mean either designing components from scratch, or customizing and integrating packaged software. No specific component modeling tools exist, and current object modeling tools only offer limited support for components (e.g. for packaging related classes together). Class packages can be used to separate the object models for different components, with a separate class package(s) for the component model. This approach, however, is not enforced by current modeling tools, and requires project naming and structuring standards.

When component modeling is being performed using existing packaged software, some form of reverse engineering or importing is required from the modeling tool to capture the existing design.

During component design the partitioned component model is designed, which defines physical interfaces and locations for components. It is important for performance reasons that communication between components is minimized, especially if they are distributed.

Reuse Support

It is during analysis and design that really large savings can be obtained by reusing existing solutions. At this stage, reuse is often at the subsystem level but can extend down to the service and module level. Asset navigation tools, which permit the retrieval of reusable components, can therefore be of great value.

For a component-based or object-based solution, reuse is usually with a specific aim. It occurs at different levels and requires different types of support.

At the analysis and design stage, common classes and components are used across applications. Repository management is required that allows easy browsing and sharing of pieces of design.

During the construction phase, there may be strong interdependencies between the core classes and the components. This must be taken into account when planning the work. When classes and components are being fixed or modified, impact analysis tools are needed to see where the modified entity is being used. This is more complex than traditional systems as a veritable spider's web of dependencies between classes, components, and applications may ensue. In addition, OO features such as inheritance and polymorphism make tracking down dependencies with simple text search tools much more difficult.

In terms of tools, a class or library browser is required, which allows easy navigation and identification of candidate components and classes.

In many cases, there can be a mismatch between design and build, especially if no detailed design phase exists. This may result in the existence of two repositories. The object or component model produced in the design phase is at a higher level and gives a good introduction or overview. The actual code, however, is where developers tend to go to find out how an application really works. When this is the case, the source code can be used as the detailed design. There are tools that extract documentation (from comments in a given format) and generate HTML pages. Examples of such tools include:

Java—javadoc, part of the jdk

C++—available from http://www-users.cs.umn.edu/~kotula/cocoon/cocoon.htm

The ideal situation is a single repository for analysis, design, and code, allowing developers to move from design to code and vice versa. However, most tools have proprietary repositories and their import/export facilities are not sophisticated enough to merge the two. For the moment, source code and design documentation remain two separate repositories.

Prototyping

It is frequently difficult to obtain specific, reliable, and complete requirements that truly express what users need. This may stem from users being unavailable or inexperienced with computer systems, or it may arise from the nature of the system under design. For example, if the system incorporates very new technology, it may be difficult for users to visualize the possibilities.

Prototyping can address this problem by simulating key user interface components, thus enabling the development team to measure the usability of the proposed system at a very early stage. The most important quality of a prototyping tool is its development speed. If prototyping can be performed in hours or days rather than weeks or months, it becomes possible to perform more iterations, which explore different options. This may lead to a much better system, given that the user's perception matures with each iteration. This, in turn, improves the quality of user input.

Very rapid, low-fidelity prototypes (for example, paper-based) play an important role in early prototyping. Hi-fidelity prototypes, used later on in the design process, should be as close to the target system as possible, and highly detailed—even down to the characteristics of a button click (e.g. click-down image, click sound, length of click etc.). This way, everyone (including the design teams) can determine exactly what the final system should look like.

User involvement at the prototype stage is of the utmost importance—regular user reviews as the prototype evolves will ensure buy-in from the users, and avoid unpleasant surprises at later stages of development.

Caution must be taken not to raise the expectations of the users in terms of the length of time it will take for the final product to be delivered. Prototyping will deliver something that looks like it "works" very quickly. It should be clear that what is delivered is a model and not an application. Clients may expect real application functionality to be developed and delivered quickly due the fast turnaround of the prototyping process, which will invariably not be the case.

Prototypes may also be used to prove architecture concepts (for example, to verify the flow of messages from the client to the host), to ensure that the system is not based on an architecture that is fundamentally flawed.

It is important to determine whether to carry forward and extend the prototype, or throw it away after requirements have been determined and perform technical design from scratch. Some prototyping tools offer the possibility of reusing code from the prototype. Although this is a valuable option, it is often available at the cost of slower prototype development. An interesting compromise may be to keep portions of the prototype (for example, user interface components) and rebuild other components from scratch.

In component based development, prototyping may be a valuable way of checking that component boundaries are well defined. However, this implies that the architecture must be defined at the time of prototyping.

Specific multi-platform prototyping facilities may be required when developing and deploying applications across multiple platforms.

Prototyping functionality is usually included in Integrated Development Environments (IDE).

WARNING: If the prototyping tool used is not part of the execution environment, the use of features that are difficult to implement in the target environment should be avoided. Prototypes will set user expectations, which may be difficult to meet once construction starts. Specifically, it is important to ensure that the performance of the prototype does not exceed the projected performance of the target system. If user expectations are built upon a highly-performant prototype, there is the potential of considerable disappointment when the final system is rolled out.

Implementation Considerations a) Will the target system run on multiple platforms?

If so, it may be important to ensure that the prototype also runs on multiple platforms (particularly if the prototype is a technical prototype as well as a functional one).

b) Is application performance an important consideration?

Prototyping tools can be used to identify potential performance problems in an application. A development team can use a prototyping tool to implement a portion of an application to identify performance problems. The team can then use this information to improve designs and provide guidelines and standards for designs. Thus, prototyping leads to a better designed and more consistent end product.

c) Do the users have experience with GUIs?

Prototyping tools allow engagement teams to demonstrate the look and feel of an application to the end user. The tool should be capable of providing a realistic understanding of the final application without requiring an extensive construction effort.

Prototypes can be used to interactively gather business requirements and design the application with the end user. If the tool supports interactive prototyping, changes can be quickly incorporated into the prototype and demonstrated back to the user. This is important when users are inexperienced with GUI. Prototyping the look and feel of the application and interactively gathering business requirements assist in gaining user acceptance of the system.

d) Are the system requirements ill defined, vague and poorly understood?

A prototype provides a means of communicating what the system is intended to do and can clarify system requirements. The prototype may become a throw-away if it becomes clear that the development style of the prototype is not conducive to a quality product. It is often more cost effective to start afresh incorporating the added understanding which was developed during the prototyping stage.

e) Are the user requirements vague?

It is frequently difficult to obtain specific, reliable, and complete requirements that truly express what users need. Prototyping can solve this problem by simulating key user interfacing components. User interface issues which are detected later are generally costly to change.

f) Is this a high usage and dedicated system, where throughput matters?

If the system is to be used by dedicated people where the measure of productivity is solely the number of transactions they can get through per second, then user interface prototyping tools are important. Prototyping tools provide a means of getting to the easiest and most efficient interface. Prototyping tools facilitate selection between alternative styles of interaction and provide a means of addressing performance issues.

g) Do the users have a choice of whether or not to use the system?

User interface prototyping tools are important since they allow developers to obtain user input early on in the GUI design process. This induces user ownership and acceptance of the system.

h) Is user input a criterion for getting the system adopted, such as might be the case when a union or organized labor is involved?

By using prototyping tools to get user input, ownership and acceptance of the system is facilitated. Adoption of the system by users and ensuring that their expectations are reasonable can make the system less expensive to deploy.

i) Does the technical architectural design use new or unfamiliar components or does it use a proven system?

Prototyping the technical architecture provides an ideal way to quickly determine if the design is feasible before a major commitment is made to a design that cannot work.

j) Are selected parts of the system to be piloted on the project?

Portions of the application could be selected for design and coding in advance of the full-scale design/code effort. This will help iron out architecture issues, user design preferences, standards, designer/development training requirements, and produce quick wins for the project which can build morale for the team and client. A prototype can serve as a means of identifying the portions to be piloted.

k) Are new team members likely to join throughout the project?

A prototype can serve to quickly familiarize new team members with the user requirements, reducing the ramp-up time for new team members. Project team members should be familiar with the goals and use of a system in order to effectively develop an application.

l) Is the project management team unfamiliar with the development team they will be working with?

Prototyping allows the project management team to judge the capabilities of a development team with whom they are unfamiliar. The prototyping effort allows some preliminary assessment of skill sets.

m) Is there some uncertainty about the product to be used in construction?

Prototyping can allow the project team to validate the capabilities and characteristics of products which will later be used for development. Many products (PowerBuilder, Visual Basic, etc.) are marketed as being the best, but may fall short of project requirements. Use of such tools during prototyping allows some "qualification" of a product's true capabilities. Performance, compatibility with existing client infrastructure, etc., can be tested.

Use of a product during prototyping (that is early purchasing) also allows a development team to determine the quality of the technical support within the company providing the product. It also allows time to work through some of the business models of those companies (their willingness to negotiate on issues, pricing, etc.).

n) Is system performance an important factor?

Prototyping and benchmarking the performance of a technical environment enables possible performance problems to be identified as early on as possible.

o) Do the users have little or no experience with the interface technology?

Prototyping serves as a means of introducing the users to the interface. Problems the users may have in working with the interface can be identified early on, and can be accounted for in training materials that are developed.

p) Is there a high degree of innovation in the work flow?

Prototyping allows the developers to experiment and, with input from users, come up with the best solution to a new and unproven workflow.

q) Do the project team and client fully understand the review and sign-off process?

Prototyping allows the project team and the client to work through the issues and mechanics of the review and sign-off process prior to the intensive development phase.

Product Considerations a) What is the purpose of the prototype deliverable?

b) Is the deliverable used to document the design of the application or provide an accurate depiction of the look and feel of the application?

An engagement team should select a prototyping tool to support the level of detail for the prototype deliverable. Initial application prototypes may use low-fidelity prototyping techniques (prototypes built using MS PowerPoint or pencil and paper, etc.) in order to document initial window designs and determine dialog flow (navigation). Some advantages of low-fidelity prototyping include little or no learning curve, lack of standardization which increases designer creativity, and ease of modification. However, this type of prototyping can not provide the user with the look and feel of the final application. High fidelity prototypes require more sophisticated tools which can provide a more realistic depiction of the application.

c) Is the prototype demonstrating the application behavior to the users?

d) Is the depiction of application behavior used in development decisions?

A prototyping tool should deliver an accurate depiction of the application including window flow and business functions. The prototyping tool should allow the display of data in a window with the look and feel of the navigation.

e) Is reusability of prototype deliverables a requirement?

f) What is the objective of the prototype?

Depending on the objectives and timing of the prototype, all or part of the prototype deliverable can be reusable during later stages of the application development process. Some projects create prototypes in the very early stages of design to demonstrate the capability of the tool and obtain user acceptance, rather than gathering business requirements and documenting design based on the requirements.

If the objective of the prototype is to document designs based upon business requirements, then prototyping tools should be chosen with reuse in mind.

g) Is the prototype used to gather business requirements?

h) Is the prototype developed during Joint Application Design (JAD) sessions with users?

The prototyping tool should be easy to use so the application designer can quickly incorporate changes to the prototype. User input should be incorporated as quickly as possible into the prototype and demonstrated back to the user. This helps to acquire user sign off on the application design and to gain acceptance of the application.

i) Does the prototyping tool support reuse?

Prototypes often represent a large investment, and in situations where a prototype is successful it should be possible to reuse the prototype in the remaining construction process.

Although prototyping tools may have the facility to provide reusable code for the system development, it is often available at the cost of having a slower prototyping tool. The reuse of code may not be a good idea since some of the design methods used for prototype development may not be suitable or desirable for application development.

Another option which is supported by some tools is that certain prototyping components can be reused e.g. window definitions. The tool selected for prototyping should allow easy transfer of the required components into the development environment.

j) Can the prototyping tool be used to design and build the front end?

The prototyping tool could also be the tool that will be used to design and build the front end. Using the same tool eliminates double entry of repository information and reduces the chance of errors when prototype information is transferred to the application design phase of the project.

k) Does the prototyping tool support functionality not provided by the construction tool of choice?

If the prototyping tool provides functionality not available in the construction tool then standards need to be put in place to ensure that the development team only produce the prototypes using features that can be implemented in the development environment. The amount of additional effort required to develop features that are easy to implement with the prototyping tool but which require work-arounds in the construction tool should be a consideration. Prototyping features which cannot be delivered will result in failure to meet user expectations.

Application Logic Design

Application Logic Design tools are used to graphically depict an application. These tools include application structure, module descriptions, and distribution of functions across client/server nodes.

A variety of tools and techniques can be used for Application Logic Design. Examples are structure charts, procedure diagrams (module action diagrams), and graphics packages to illustrate distribution of functions across client and server.

Application Logic Design functionality is also provided by a number of Integrated Development Environments (IDEs). (see Tools—System Building—Construction)

With component-based development, Application Logic Design is performed through object and component modeling. The functionality is captured in use cases, scenarios, workflows and/or operations diagrams along with interaction diagrams/sequence diagrams (See Object Development Methodology for samples of deliverables). These are usually produced using an object modeling tool.

Implementation Considerations a) Is there a need for logic representation?

Use Application Logic Design tools to graphically depict the logic of an application. This is a common requirement on most engagements.

b) Is there some uncertainty about the validity of the business case?

The Application Logic Design tools provide a means of confirming the complexity estimates and hence facilitate a revision of estimates before going into construction. By confirming the validity of the complexity estimates, the business case is also confirmed. It is at this stage that the decision is made whether or not to continue with construction.

c) Is performance modeling required?

Application Logic Design tools can provide a basis for performance modeling, based on the processing ability of the CPU, parallelism, and pipelining. The tools can be used to graphically depict system complexity, from which a performance model can be derived.

d) Is the programming team inexperienced?

Application Logic Design tools provide a vehicle for communication from designer to programmer. This is particularly important when programmers are relatively inexperienced and need detailed guidance, which comes from the detailed design that is documented using these tools.

e) Is system maintenance part of the project definition?

Application Logic Design tools, and the designs that they contain, provide documentation of the system which will support maintenance in the long run. If the maintenance team is very experienced, or if the system is a throw-away prototype, which will not be reused or maintained in the future, then Application Logic Design tools may not be required.

Product Considerations a) Should the engagement team build a custom Application Logic Design tool or purchase an existing one?

Engagement teams must determine whether standard design templates provided by vendors meet project needs, or if the architecture must provide custom solutions. CASE tools tend to provide standard Application Design documentation. Most custom solutions utilize word processing tools to build Application Logic Design shells for use by development teams.

b) Are several tools to be used to provide Application Logic Design facilities?

A single tool may not provide all the facilities required. The different tools must interface with one another in order to promote consistency of the Application Logic Designs.

c) Does an existing tool provide the required functionality?

The development team may require facilities to produce procedure diagrams, flowcharts, or pseudocode. These facilities may already be provided by existing tools, for example, pseudocode can generally be produced by an application development tool.

d) Does the Application Logic Design tool reflect the close relationship between application logic and the user interface?

In a good GUI program design, the application logic is often closely linked to the user interface. A single design document capable of capturing this relationship could serve as a key input into the programming process. Traditional tools only provide separate presentation design and application processing module design documents.

Database Design

Database design tools provide a graphical depiction of the database design for the system. They enable the developer to illustrate the tables, file structures, etc., that will be physically implemented from the logical data requirements. The tools also represent data elements, indexing, and foreign keys.

Many data design tools integrate data modeling, database design, and database construction. An integrated tool will typically generate the first-cut database design from the data model, and will generate the database definition from the database design.

With an object-based or component-based solution the data modeling task changes. In most cases, relational databases are still used, even where there are no dependencies on legacy systems. As there is an 'impedance mis-match' between an object model and a data model, a mapping activity must be undertaken. There are standard mechanisms for doing this.

There is a tendency (especially when dealing with legacy systems) to treat data models and object models the same. It is important to recognize that at best, the data model represents only the static part of the object model and does not contain any of the transient or dynamic aspects. The physical data model may also change significantly (for DB optimization), further confusing the issue.

There can be performance problems with objects mapped to a relational database. In a worst case scenario, an object can be spread across many tables, with a single select/insert for each table, and as each object is loaded one by one, the performance becomes very poor. Some tools provide lazy initialization (only loading the parts as they are needed) and caching (minimizing DB hits).

The current trend seems to be for object-relational databases, with vendors such as Oracle adding object features to their core products. Although the support provided at the moment is limited, it is likely that in future versions Java or C++ classes will be able to interface directly.

Implementation Considerations a) Do the design ideas need to be communicated to a large team of developers?

Database design tools are important where design ideas must be communicated to the development team. Where the development team exceeds ten people, this design must be formalized. Database design tools provide a graphic depiction of the database design for a system, whilst at the same time enabling the developer to illustrate tables and other structures that will be implemented physically.

b) Is system performance a major consideration?

Database design tools become especially important if performance is critical, since database design contributes substantially to the overall performance of the system. Database design tools provide quantifiable performance data which is a crucial component of the overall performance model.

Database Design tools also provide a means to model I/O on devices such as hard disks, optical drives, and tapes etc. This information can be used in a performance model.

c) Does the project have multiple teams working on multiple functional domains?

The database design component is important in the case where multiple teams are working on different functional domains, since they often model different parts of the database separately and then incorporate these models at the end into one large database model. Database design tools can be used to enforce consistency of the different database designs.

d) Does the database include a very large number of tables and elements?

Navigation through a large number of tables is complicated and can be simplified significantly if dedicated database design tools are used.

e) Are there likely to be conflicting system requirements?

Different teams or users may have different requirements which conflict. These requirements may have to be rationally traded-off against each other. Where these requirements are performance related, the trade-off can only be rationalized on the basis of a good database model.

Product Considerations a) Does the product provide the following features?
  Support for definition of DBMS advanced features (e.g. triggers, stored procedures, replication, application logic, application generation, referential integrity)
  Support for versioning and change control
  Cross platform and DBMS integration b) Should the database design tools support database construction?

Many database design tools allow for database construction. Such tools may help translate a logical database design into a physical design, or they may generate Data Definition Language (DDL) code or Data Manipulation Language (DML) code. The advantage of using a tool that provides this facility is that it simplifies the transfer of design information into a physical representation and can be used to ensure consistency from design into construction of the database.

Presentation Design

Presentation design tools provide a graphical depiction of the presentation layer of the application, such as windows, dialogs, pages, navigation and reports. Tools in this category include window editors, report editors, and dialog flow (navigation) editors. Window editors enable the developer to design the windows for the application using standard GUI components. Report editors enable the developer to design the report layout interactively, placing literals and application data on the layout without specifying implementation details such as page breaks. The majority of these tools generate the associated application code required to display these components in the target system.

Dialog flow (navigation) editors enable the developer to graphically depict the flow of the windows or screens.

The Control-Action-Response (CAR) diagram is a commonly used technique for specifying the design of GUI windows. It is typically developed using a matrix or spreadsheet tool such as Microsoft Excel.

The majority of Netcentric systems use Web browsers to provide a common cross-platform user interface. Presentation design for this type of environment therefore entails the generation of HTML pages, often with additional components (JavaScript, 3rd party ActiveX controls, Plug-ins) providing enhanced functionality or media content. Many tools are currently available for designing and creating web content, although HTML remains the common denominator, at the very least as a placeholder for the content.

In the case of systems published on the Internet, defining the target audience is less straightforward than in traditional systems, but equally important. Having a good understanding of the intended audience will be a big advantage when thinking about user interaction with the system, and therefore, the presentation layer of the system.

Implementation Considerations a) Does the project want to use a single tool for prototyping and GUI design?

Presentation design tools provide the ability to use a single tool for both prototyping and GUI design. This decreases the learning curve during design and permits components of the prototype to be reused.

b) Are user requirements clearly defined?

c) Are numerous iterations of design anticipated?

These tools make application development easier and faster through point-and-click capabilities and built-in functions. Reduction in the overall presentation layer design/development effort allows for more design iterations, and thus more chances for user feedback.

d) Has a specific construction tool been selected for the project?

If the tool to be used for construction is not known at design time then specific tools for presentation design are needed.

e) Is the design complex?

f) Does the design have to be presented to multiple users?

g) Do the users have conflicting interests?

h) Does the design have to be signed off?.

i) Does the design have to be maintained over time?

In these cases a dedicated presentation design tool can be used to provide maintainable documentation of the presentation design which can be used to clarify and communicate issues.

Product Considerations a) How much does the tool cost?

Product components, maintenance agreements, upgrades, run-time licenses, and add-on packages should be considered.

b) Will the design tool be used for programming of client applications? What programming language is supported?

If the design tool is used for programming, there are several features of a tool that must be considered. These features can have an impact on the productivity of programmers, performance of the applications, skill sets required, and other tools required for development. These features include:

What programming language is supported? Is the programming language interpretive or compiled? Is it object oriented or a structured procedural language?

Does the tool support programming extensions to Dynamic Link Libraries?

What are the debugging capabilities of the tool?

c) Will the tool be used with a large development team?

If the development team is more than 5 people, a tool should provide support for multiple developers. This support includes features such as object check-in/check-out, a central design repository for the storage of application objects and user interface definitions, and version control. Additionally, the development team should be able to cleanly divide the application(s) into pieces that can be worked on by multiple developers.

d) If the tool is also going to be used for application development, how well does the tool perform during production?

Computational, network, data retrieval, and display speeds differ for products. Factors to consider are whether the application will consist of heavy data entry, transaction processing, or a large user base.

Does the product integrate with other tools and/or support other tools in the development and execution environments?

It is important to determine how well the product integrates with other design and development tools, presentation services (graphics, multi-media, etc.), data access services (databases and database API libraries), distribution services (distributed TP monitor), transmission services (SNA, HLLAPI, etc.), data dictionary, desktop applications, and programming languages for call-out/call-in. Additional consideration should be given to add-on and third-party products/enhancements such as specialized widgets, report writers and case tools.

e) Is the tool scalable?

The tool should be scalable to support growth in application size, users, and developers.

f) What functions are required in the control set?

At the minimum, a tool should support basic widgets (push buttons, list boxes, etc.), window styles, (multi-window, multi-document, paned-window), and menu styles, along with validation and inter-application communication. Consideration should also be given as to the extensibility of the toolset via add-ons and third party products.

g) What databases are supported?

h) What protocols are used to communicate with the database?

Important considerations include the supported databases and protocols used to communicate with the databases. The tool must support the selected database. Additionally, if database selection may change, it is important that the tool have the ability to support other databases with minimal impact oh the application development. Native database interfaces tend to have better performance than open standards such as ODBC.

i) What level of technical support, documentation, and training is required to ensure the productivity of developers?

The extent of support (on-site, phone, bulletin board, world-wide, etc.), quality of documentation, and availability and location of education/training should be considered.

j) What type of learning curve is associated with the tool?

Developers using the product should be able to become productive quickly. Factors which reduce the learning curve include an easy to learn and intuitive interface, thorough and clear documentation, and on-line help.

k) Can the tool be used for both prototyping and GUI design?

The ability to use a single tool for both prototyping and GUI design will reduce the development learning curve. Tool integration with all other development tools should also be considered.

l) What platform(s) are supported?

The platform(s) that must be supported, i.e., MS-DOS, Windows, IBM OS/2, UNIX, or UNIX Motif, are an important consideration, as are any hardware restrictions.

m) Is there a need for consistency across multiple screens or windows?

Some presentation design tools provide the facility for reuse of elements. This can be used to enforce consistency across multiple screens and can accelerate development. This feature is not available in low-end presentation design tools, such as MS PowerPoint.

One means of ensuring reuse is for the tool to support a central library of predefined widgets or screen elements. This library should be extendible and customizable, allowing developers to create new widget/element definitions or to enhance existing ones.

n) Is multi-language support a consideration?

Special characters, differences in field lengths, and differences in number formats are some of the things that contribute to the complexity of a multi-language application. Window and report design are among the areas affected by differences in the language used for presentation.

Strategies on how windows are displayed are affected if multi-language support is a requirement. Are separate windows painted for each language or are window literals dynamically replaced? The former will produce windows that are more visually appealing but requires more significant effort to create and maintain.

The presentation design tools should facilitate documentation of these differences for design purposes and allow the design strategies to be implemented.

o) Is the tool integrated with the repository of choice?

The presentation design tools should be tightly integrated with the system components stored in the repository, such as windows, reports, screens, and other more abstract models to ensure consistency.

p) Is a multi-media application to be developed?

Touch screen hotspots, video clips, hypertext, pointer device hotspots and other similar design objects must be supported by the presentation design tool if the design is for a multimedia application.

Communication Design

An increasingly important aspect of system design is communication design. After the fundamental communication paradigms have been chosen, each exchange must be designed to allow for the detailed design of each module (clients, services, functions), and to lay the basis for more refined performance modeling. To ensure against interface problems, these tools should be tightly integrated with the design repository. One simple way to document communication interfaces is to define include files, which hold the interface definitions.

Implementation Considerations a) Is performance simulation or modeling required?

Thorough performance simulation or modeling requires a communication model. A performance model is particularly important if the system is large, heterogeneous, and complex.

A valid performance model can only be created once a detailed communication design has been developed for the system. The performance model is derived from the detailed communication design. Communication design tools provide a means of documenting the physical design of the system, such as protocol stacks, message sizes, routers, bridges, gateways, LANs, WANs, MANs, etc. as well as the logical design, both of which are used to develop the performance model and to simulate performance.

b) Is the system migrating from a central to a distributed environment?

c) Is the system migrating from a LAN to a WAN environment?

d) Is the system migrating from a country wide WAN to a global network?

When development takes place in a mainframe environment, performance is relatively predictable. In a distributed environment, response time is dependent on the communication design.

Migrating from a LAN to a WAN, or from a WAN to a global network will drastically impact the performance of the system, and this type of migration requires the development of a complete communication design from which a performance model can be derived. Thus, tools to facilitate the communication design become a critical part of the development architecture when migration of this sort is involved.

e) Is high network performance required?

Communication design tools are essential in developing systems where critical business operations have to have maximum availability and minimum down time. One of the primary contributing factors to high performance in client/server environments is a good network design. A good network design can only be achieved through a good communication design.

Product Considerations a) Is the tool repository based?

The best support for detailed communication design for a large development team is provided by a repository. Here the messages, calls, and queries can be modeled and designed as entities in their own right. These entities provide a necessary basis for performance and module design, which can be shared by all developers.

b) Is there a need for a graphical depiction of the communication design?

A graphical depiction of the communication design may be required. For simple designs, tools such as PowerPoint are normally adequate. Data flow diagrams may be used to show how clients send messages to services. The tools used should help developers to ensure that objects in the diagrams are linked to the actual objects (Windows, Services, etc.) in the repository. This will maintain consistency of the design documentation with the actual objects used in development.

c) Do existing tools provide the necessary functionality required to produce the communication design for the project?

A simple and effective method of defining interfaces is by using include files to hold the interface definitions. The application development tools usually provide this facility.

A spreadsheet package such as Excel may also be used to design message layouts. For simple graphical depictions of the communication design, a tool such as PowerPoint is adequate.

d) Does the tool encapsulate knowledge of the services provided by the middleware layer?

The middleware layer provides the basic functions for applications in a heterogeneous environment to interface with operating systems, networks and communication protocols.

If the tools used encapsulate knowledge of the middleware services, low level design of communication (e.g. designing at the level of named pipes and sockets) need not be supported or investigated. The middleware component abstracts this level of detail so that the designers need not concern themselves with complex technical issues.

Usability Test

From a development perspective, systems that are designed and tested with usability in mind offer clear advantages. This is providing Usability Testing is executed from the user perspective, and from the very beginning of the development process. Usability Testing can help developers:

Reduce risk by confirming that they are building the right solution

Identify new system requirements

Decrease development time and money by reducing rework

Achieve a smoother conversion, with less disruption to business

Each system is designed to meet the unique requirements of its users, and therefore benefits from a different mix of testing techniques. In many cases, designers find that the best starting point is to build and test low-fidelity prototypes (see Tools—System Building—Analysis & Design—Prototyping). These are paper-and-pencil versions of user interfaces that allow developers to demonstrate the behavior of systems very early in development. Before any code has been written, developers build prototypes on paper and test them with real users, simulating the human-computer interaction. Designs are adjusted and retested several times until a usable solution emerges. When it is time to begin coding, developers already have an excellent idea of how the system should work and what the users want.

Once the user interface has been coded, the high-fidelity prototype is ready for online usability testing. The test results are compared with previous tests and routed back to the developers. If lo-fi prototypes were used earlier, the major design issues have already been resolved. Refinements at the "hi-fi" stage should focus on perfecting the details.

In the later stages of development, usability laboratories can be extremely helpful for evaluating system design. Usability labs, which can be stationery or portable, rely on videotape and screen capture methods to record how users interact with prototype systems. Within a few hours of testing, lab administrators can create a highlights videotape of problems that users encountered. These tapes can be used immediately by developers and project managers to modify the hi-fi prototype as required. The average usability test results in 70 to 100 specific recommendations for improvement.

Remote testing, or telecasting, is an online variation of the usability lab. This still-emerging method relies on computer networks to conduct system evaluations. Remote testing enables developers to test a large number of users efficiently and without incurring travel expenses.

Reverse Engineering (830)

Reverse engineering tools are used to capture specific, relevant functional and design information from a legacy system for use in a new, client/server system or to restructure the existing system for improved performance and maintenance.

Interactive Navigation

Developers use interactive navigation tools to identify requirements for a new system from the functionality and design of a legacy system. These tools enable the developer to interactively and graphically navigate the legacy system, determining the system's characteristics such as system structure, module flow, flow control, calling patterns, complexity, and data and variable usage. An alternate form of presentation is through reports. These provide cross-reference listings or graphical representations of control or data flows.

Graphical Representation

Graphical representation tools are used to display important system information in a form, which is easier to assimilate. These tools may, for example, produce structure charts, database schema diagrams, and data layouts. They can also print matrices that indicate relationships between modules and files or between jobs and programs.

Extraction

An extraction tool, in conjunction with a repository population tool, enables the developer to reuse selected portions of a legacy system. The extraction tool can typically read and extract information from source code, screens, reports, and the database. The most common information extracted from a legacy system, however, is the data: record/table structure, indexes, and data element definitions.

In component-based architectures, as systems are often built on top of legacy databases, some extraction tools allow generation of an object model from the legacy database data model (DDL). By understanding the E-R diagram represented by the database, it is easier to create an efficient persistence framework which isolates business components from a direct access to relational databases. Caution is required, however, as the resulting model is at best only partial, as an object model has dynamic aspects to it as well as static relationships, and may not correctly reflect the analysis performed in the problem domain.

Repository Population

The repository population tool is used to load the information from the extraction tool into the development repository. These tools convert the information from the legacy system into the syntax of the development tools repository. The extent of the information loaded into the repository is a function of the Information Model of the development tool repository. Information that is not represented in the development tool repository cannot be loaded into the repository.

Restructuring

Restructuring tools are not analysis tools like the previous categories of reverse engineering tools, but design and construction tools. They enable the developer to rebuild a legacy system, rather than replace it. Examples of this type of process include restructuring spaghetti code with structured code, replacing GOTO's, streamlining the module calling structure, and identifying and eliminating dead code.

Data Name Rationalization

Data name rationalization tools extract information on variable usage and naming, and show relationships between variables. Based on these relationships and user input, these tools can then apply uniform naming standards throughout the system.

Packaged Component Integration (832)

Packaged components are generally third party components that provide ready-made business logic that is customizable and reusable. These can range from simple components offering limited functionality (for example, worksheet or charting GUI components), to components that handle a significant portion of the application architecture (for example, data access components and firewalls). The advantage of using such components is that they have already been coded; tested, optimized, and documented.

The fact that these components come from third-party software houses does not always guarantee their quality. In order to minimize the dependency of the final system on these components (thus reducing the impact of possible changes within the libraries), it is recommended that wrappers are written to enclose any third-party components. This way, if any changes are made to the internals of the components, only the wrappers would be affected, allowing the application and architecture code to remain unchanged.

Product Considerations a) Does the component require significant customization?

When selecting components, it is important to get as close a match as possible to the functionality that is required.

b) Will the vendor guarantee required functional enhancements?

If functionality is missing from a component that cannot be added using the standard customization tools provided, it is vital to get a vendor guarantee that the enhancements will be made, and to agree on a deadline for these enhancements.

c) Will the vendor guarantee consistency of all interfaces across future releases?

The biggest danger in using packaged components is that the vendor will make changes to the component interfaces. When selecting packaged components make sure the vendor guarantees backwards compatibility of all the existing interfaces provided by the component. If this is not the case, it will entail much reworking of the application code in order to be able to take advantage of (potentially important) upgrades to the component.

d) What are the performance implications of using a packaged component?

Components are often developed with a preferred platform in mind. Components optimized for one platform may have severe performance problems on others. If performance is a factor (and it nearly always is) ensure that components are designed specifically for the platform of the target system.

e) Does the component provide standard or proprietary interfaces?

When choosing between packaged components, always choose standard interfaces over proprietary ones. It will always be easier to customize and interface a component whose language is known to the development team, rather than one which requires developers to learn a new proprietary language.

Customization

Packaged components usually do not provide the exact functionality that is required of the target system because they are created by third parties. They may have to be configured in order to behave in the desired fashion. The majority of packaged components allow one of two methods of customization—either by using standard construction tools (such as an editor and a C compiler), or by using proprietary toolkits provided by the vendor.

Implementation Considerations a) What level of support is provided by the component vendor?

It is vital that the vendor provides an appropriate level of support for the component such as documentation, telephone support, remote support, training, and onsite support. It might also be necessary to include vendor developers on the Application team. This is especially important where component customization relies on proprietary toolkits.

Construction (834)

Construction tools are used to program or build the application: client and server source code, windows, reports, and database. Along with the onset of Visual Programming, the more traditional form of construction tools have been superceded by Integrated Development Environments (IDEs) which take all the basic components required for construction, and integrate them into a single system. Although IDEs are now the preferred tools for most construction, the components that make up these tools remain the same—Source Code Editor, Compiler/Linker/Interpreter, Generation Tools and Debugging Tools.

Visual Programming tools, initially associated with the rapid development of the client-side of client/server applications, have now matured and expanded their domain to cover entire client/server development (e.g. Visual C++) and Netcentric development (e.g. visual Java IDEs).

IMPORTANT: While IDEs provide the basic components for construction, not all the functionality offered by the components listed here is provided (for example IDEs do not generally provide Help text generation or DDL generation). IDEs can usually be customized in a way that other tools (Version Control, Generation, Repository Access etc.) can be integrated. It is necessary to plan time for this up front. It should not be left to the developers to do this individually.

In addition to the standard construction components, a new set of utilities exist which can help increase the quality of code generated by developers. QA Utilities verify the quality of constructed code, and its conformance to standards set down for the development environment.

It is important to ensure that developers use tools that are standard to the development environment. Now that Internet access is a standard facility for developers, there may be the tendency for people to download their own preferred tools, or upgrades to standard tools. This not only affects the management of the development environment, but could easily result in the generation of code that is incompatible with the rest of the code in the development system (for example, consider the effect of developers on the same team using tools which employ different version of the JDK).

Product Considerations a) What size is the development team?

When IDEs were first developed, they were targeted at individual developers. This means that support for team development is still not fully mature in the majority of IDEs, although some are closely integrated with third-party configuration management packages. When selecting an IDE it is important to ensure that team development is sufficiently catered for.

b) On what platform is the system expected to run?

c) Is the target system expected to run on multiple platforms?

The construction tools selected must be able to support the target platform(s) of the system to be developed.

Source Code Editor

A source code editor is used to enter and edit source code for the application. Complexity varies from simple ASCII text editors to fully integrated editors such as those provided by Integrated Development Environments. Typically however, they are linked with a debugger so that coding errors which are identified during compilation can be more easily corrected, since the error and the source code generating the error can be viewed simultaneously.

Other features include:
Dynamic syntax checking, improving productivity by detecting errors as they are made, rather than at compile time.
Color coding, which automatically applies different colors to text depending on its type or context (e.g. comments, variables, reserved words etc.), thus making the code more readable.
Automatic layout, which indents code depending on its logical level (e.g. loops, conditionals etc.)

On the whole, these features will help ensure that code developed by the team is following project standards as opposed to individual programming styles.

Implementation Considerations a) Web-Based Development

Due to the tendency of Web-based applications to combine multiple components (such as HTML, Javascript, Java applets, CGI scripts etc.), numerous source code editors may be required for the development of any single web application.

Product Considerations a) How well integrated is the editor with other tools in the development environment?

The level of integration with the rest of the environment is an important consideration when selecting a source code editor. Most editors now come as part of an IDE, and are therefore fully integrated.

b) Does the editor support multiple languages?

Some IDEs provide support for many languages using the same interface (for example, MS Developer Studio supports C, C++, Java, Fortran). This has the advantage of providing the user with a common approach to coding, regardless of the language being used.

c) What features are provided by the editor?

As mentioned in the component description, many features may be provided by the editor, which can save time and improve code quality. A feature-rich editor is therefore often worth the investment.

d) Is the product easy to learn and use?

The source code editor should be easy to use with little or no training required.

e) Is an acceptable source code editor already provided by the operating system or other tools in the development environment?

Most Development tools and operating systems already include a source code editor. These source code editors are usually just simple text editors.

f) What is the amount of the application code?

Some source code editors may not have the ability to handle extremely large files while other tools are built specifically for that purpose.

Compiler/Linker/Interpreter

This component is responsible for taking raw code (usually in ASCII format) and creating the necessary object, library, byte-code, or executable files that become components of the final system. The actual tools required depend on the development language, but always consist of one or a combination of the following components:

Compiler

Linker (preferably incremental—the linker can substitute a new version of a single module rather than having to re-link the entire program)

Interpreter, which can speed up the test/correct cycle by eliminating the compile and link steps In the majority of Integrated Development Environments, the Compiler, Linker and/or Interpreter are included as an integral part of the system. In addition, the management of compilation and linking is automated using MAKE utilities which understand the dependencies between modules in the system. This allows the system to trigger all necessary re-compilation and re-linking when a module in the system is changed, thus avoiding the time consuming task of re-compiling and re-linking the entire system.

Product Considerations a) Is the tool easy to use?

The tool should be relatively easy to use in order to reduce the learning curve.

b) Does the tool support the platform in the development environment?

The compiler/linker/interpreter tool must be compatible with all the platforms upon which the application is being developed. Besides compatibility, tool performance may be platform dependent.

Source Code Debugger

A source code debugger is a tool used to unit test a program. This tool provides information about the activity of programs and systems, enabling automatic analysis and diagramming, assisted code tracing, editing capabilities, and automatic documentation. The debugger allows the developer to enter program break points and step through a program, tracking the progress of execution and identifying errors interactively. It is typically used in conjunction with the source code editor so that coding errors identified can be more easily corrected, since the error and the source code generating the error can be viewed simultaneously.

Symbolic source code enables easier identification of where errors occur. Preferably, the debugger should be flexible enough to work with any combination of compiled modules and source modules. In addition, the debugger should be able to handle calls to the database and to other modules.

Product Considerations a) What testing team factors should be considered when using a source code debugging tool?

Communication between development team and testing team:

A code analysis tool can help the testing team detect unreported changes in the application code, and therefore help alleviate possible bad communications between the development and testing teams. Thus, bad communications between teams will still influence positively the decision to use code analysis tools.

Generation

Generation tools include:

Shell generation

Make file generation

Window/page generation

Data Definition Language (DDL) generation

Data Manipulation Language (DML) generation

Code generation

Include file generation

Help text/module description generation

Trace code generation

Shell generation is the process of generating a starting point for programming. Shell generation is typically repository-based but can also be based on interaction with the programmer, where the generation utility requests key information about the program, and generates a starting point as a result of this. Key information (whether obtained from the repository or through a dialog with the programmer) may include:

Data base tables accessed

Methods and attributes defined (for objects)

Interface information

Based on this information, the generator selects the appropriate include files and creates skeleton code which may be used as a template for the programmer. This template may also include audit history for the module and standard code such as error handling.

Make file generation is integrated into the majority of IDEs

Window/page generation (which is an integral component of Visual programming tools) allows the developer to rapidly design windows and pages using a point and click graphical interface. The relevant source code is subsequently generated from these designs.

The generation of DDL and DML is often hidden from the developer by using data access functions or objects, provided by a large proportion of IDEs (e.g. MFC, JDK) Help text and module description generation (not usually provided by IDEs) analyzes developer's raw code (including comments) and creates descriptions which may be used by developers to understand the contents of modules or objects. This is particularly useful for component-based development, where methods and attributes of objects may be automatically documented.

Trace code generation allows the insertion of traces into raw code in order to aid debugging.

Implementation Considerations a) Does the project want to isolate developers from the technical environment as much as possible?

b) Are there a large number of developers which makes it difficult to enforce standards and consistency among developers?

Generators are typically used to enforce and maintain consistency throughout an application. The main benefit is a reduction in training. In addition, the code generated will automatically be checked for errors, shielding the developers from many complexities of the technical environment.

c) Are there a large number of developers or a large amount of code?

d) Can significant time be saved by creating generators to generate code for reuse and regenerated code to propagate changes?

Generators are used to leverage the powers of code reuse and code regeneration. The ability to reuse code reduces both the time and resources required on a project. Code regeneration eases maintenance issues by propagating changes throughout multiple sections of code.

Product Considerations a) Can the generation tool provide code which meets performance requirements?

The code/applications generated by the tools vary in performance. Optimized code usually results in faster run times. It is important to identify the high priority components that will benefit most from the tool.

b) Should the engagement team build a custom generation tool or purchase an existing one?

The decision to custom build or to buy available case tools must be determined by the development team. Most generators are usually custom built because often the technical environment and architecture have custom components that cannot be handled by a package generator. Associated with custom building are the issues of added cost and development time, but performance can be closely monitored and changes performed on the spot.

c) Does the generation tool support the development and execution platforms?

The tool must support the current or proposed platform.

QA Utilities

QA Utilities verify the quality of completed code, and that it conforms to project and international standards. These types of tools include the following:
  Code Analysis—Code analysis provides the objective information and metrics needed to monitor and improve code quality and maintenance (e.g. static analyzer, documentor, auditor).
  Code Error Checking—Checks code for common errors (e.g. syntax errors, uninitialized and badly assigned variables, unused variables)
  Code Beautification—Re-formats code in order to make it easier to read and maintain.
  UNIX Portability Checking—Checks compliance with basic portability standards—particularly with programming standards that ensure portability across UNIX platforms (e.g. POSIX compliance and OS/2-to-Windows portability).
  100% Pure Java Checking—Checks that Java code conforms to the 100% Pure Java standard.

Code/Object Libraries

Code and Object libraries provide the developer with ready-made components (such as GUI components or simple utilities), which may be integrated into architecture or application code. The advantage of using such components is that they have already been coded, tested, optimized, and documented.

Code and Object libraries may be differentiated from packaged components in two ways:
  They contain little or no business logic
  Source code is usually provided (as opposed to the 'black box' component approach)

That these libraries come from third-party software houses does not always guarantee their quality. In order minimize the dependency of the final system on these components (thus reducing the impact of possible changes within the libraries), it is recommended that wrappers are written to enclose any third-party code. This way, if any changes are made to the libraries, only the wrappers would be impacted, allowing the application and architecture code to remain unchanged.

Implementation Considerations a) Does the object/library really need to be wrapped?

It may not always be prudent to wrap all third party objects/code that are to be used on a project. Sometimes the cost involved may outweigh the value of wrapping an object/code. As objects/code become more complex, with more functions/interfaces, then the value of wrapping them becomes more tangible.

Media Content Creation

As systems become increasingly user-facing, it is important to design user interfaces that are not only functional, but also engaging and informative. This is especially true of Internet and kiosk-based systems, where users have a notoriously short concentration span.

This requirement for more attractive user interfaces has triggered the evolution of media-rich applications, the development of which requires new tools and processes, and brings with it a whole new set of issues.

Media content can be broken down into three major media types, each with its own set of tools:
  2D/3D Images/Animation
  Video
  Audio 2D/3D Images/Animation Tools to handle these images range from simple paint packages to highly complex multi-layered animation graphics packages. The images created by these tools may be pixel-based (bitmaps) or vector-based, each with their own advantages.
  Pixel-based tools (traditional graphics and image processing tools) offer more image flexibility especially in terms of color gradation and shading, but produce relatively large files. This format is therefore useful where the use of high-quality textured images, or highly colored images is important, but where file storage and transmission is not an issue (where the media content is local to the client application, such as in a kiosk).
  Vector-based tools (where the image is defined by formulae rather than pixel position) offer much smaller file sizes, and dynamic image re-sizing, while producing excellent print quality, but cannot easily handle shading and color gradation. This format is more appropriate where file size is an issue (web pages).

Video

The high cost and complexity of video production equipment, along with the skills required to manage the process of video production mean that it is usually outsourced to a third party. It is important however that the personnel charged with creating video content are an integral part of the Application team.

Audio

The tools required for creating audio content depend on the quality required, and whether or not the content is original. For 'sound bites' or pre-recorded audio, simple desktop audio editing applications are adequate. For high-quality original content, a professional recording studio is recommended. Again, if third parties are involved, it is important that they are fully integrated into the team.

For both image and audio, it is possible to purchase re-usable content from agencies, usually delivered in the form of CD-ROMs.

NOTE: Tools required to store and manage media content (and storage formats) are discussed in Tools—Information Management—Media Content Management Test (836)

Testing applications (client/server or Netcentric) remains a complex task because of the large number of integrated components involved (for example, multiplatform clients, multiplatform servers, multitiered applications, communications, distributed processing, and data), which, in turn, results in a large number and variety of Testing tools.

For any large scale testing effort, it is vital to have a repository (see Tools—Information Management—Repository Management) that is capable of managing the data required by each of the test subcomponents. The repository should manage the following entities:

Test conditions
Test cycles
System Investigation Requests (SIRs), triggered by a deviation of actual results from those expected
Test data
Requirements Within the repository, the following relationships between entities must also be managed:

Test cycle and the system component to which it refers
Test condition and the test cycle it belongs to
Requirement and the test condition that tests that requirement These relationships make it possible to analyze efficiently the impacts of change and to document the state of system test. For example, the number of outstanding SIRs per cycle can easily be provided based on these relationships.

In some cases, the mentioned entities and relationships cannot be managed within the repository, and may have to be modeled outside the repository (for example, in a teamware database). In this case, the link between the repository and the external tools must be provided by a judiciously chosen set of procedures and custom integration tools.

Component-based development may have an impact on the way in which testing should be performed.

A number of firm initiatives have conducted considerable research into the field of testing:

Year 2000 Testing Contacts and KX Resources
The Technology Library contains further information including tool evaluations, practice aids, and newsletters
Integrated Testing Environment Job Aid Product Considerations a) When should vendor tools be used in the testing process?

Vendor tools are more appropriate when the requirements are totally dependent on the software development platform. Moreover, when the technology evolves too quickly, it requires a software organization to handle the changes.

Test Data Management

Test Data Management tools allow developers to create and maintain input data and expected results associated with a test plan. They include test data and archiving tools that assist in switching between cycles and repeating a cycle based on the original data created for that cycle.

Test Data Management functionality may be provided by the following tools:

Test data generation tools—usually generate test data by permutation of values of fields, either randomly or systematically.
Test design repository tools—facilitate structured design and maintenance of test cases. They help the developer find existing test cases, cycles, and scripts that may be appropriate for reuse.
Data management tools—provide backup and restore facilities for data. They also provide configuration management for multiple versions of data, maintaining consistency among versions of test data.

Implementation Considerations a) What guidelines should be followed when creating component and assembly test data?

To minimize testing errors when creating component and assembly test data, follow the guidelines provided by the AC Methods job aid for quality test data.

Product Considerations a) What testing team factors should be considered when using a Test Data Management tool?

Size of the Testing Team

The larger the testing team, the more benefits will be derived from using a Test Data Management tool (easier control over the test data for the various testers), a configuration management tool (easier control over all system configurations and component versions), and a test plan management tool (easier control over all test cycles, subcycles, their execution statuses, and so on).

b) What engagement factors affect the use of Test Data Management tools?

Risk Rating of the Engagement

In general, management and planning tools help better address the engagement risks.

A high risk rating for the engagement will affect positively the decision to use tools such as test planning, Test Data Management, problem management, and configuration management.

Criticality of the Engagement

In general, management and planning tools help better manage the engagement and ensure the timely delivery of a quality system. Therefore, dealing with a highly critical engagement will most likely affect positively the decision to use tools such as test planning, Test Data Management, problem management, and configuration management.

Test Data Manipulation

Test Data Manipulation tools are used to create original test data and, sometimes, to modify existing test data. Such modifications may be needed to process a change in the database schema and to correct intermediate results in order to complete a test cycle. Some test data manipulation tools generate test data very effectively.

Test Planning

A Test Plan consists of several components:
Test schedule

Test execution tracking
Test cycles
Test scripts
Test conditions
Test condition generation
Input data
Expected results Test Planning definition and maintenance tools define and maintain the relationship between components of a Test Plan.

Implementation Considerations a) What guidelines should be followed when assembly testing the technology architecture?

When deciding which areas of the technology architecture to test, follow the guidelines provided by the a job aid for technology architecture assembly testing.

b) What guidelines should be followed when creating test scripts?

When preparing to test system components, scripts can be used to verify that the system design specifications are properly implemented. A job aid provides guidelines for creating product test scripts.

c) What guidelines should be followed when creating test cases for the component test?

When preparing component test data, a checklist helps ensure that all cases are thought up so that component testing is complete.

d) What components interface with the Test Planning component?

The following components interface with the Test Planning component: Tools—System Building—Test—Test execution. This interface relates to the actual Test Planning scripts for an automated script playback capability. The scripting tool can be call directly front the Test Planning tool, which runs it or loads it to the target platform. More generally, all scripts, and actual results should be linked to the cycles.

Tools—System Building—Test—Test Data Management. Before beginning the cycle, the transfer, load, and refresh of test data can be run from the Test Planning tool.

Tools—Information Management—Repository Management. Each conversation, dialog, or executable tested in a cycle can be cross-referenced so that it is possible to know from the design where a functionality is tested.

Tools—Configuration Management. Each conversation, dialog, or executable tested in a cycle can be cross referenced so that it is possible to know from the design where a functionality is tested.

e) What is a repeatable test model?

j) What is the importance of a test database?

g) What is the team member retention with a repeatable test?

h) How does a repeatable test model affect testing automation?

The following is an overview of the repeatable test model as documented by the Reinventing Testing Project (RTP).

A repeatable test model consists of tests that can be easily executed by staff who have little or no experience of the application being tested. A repeatable test script provides the detailed steps necessary to test the functionality. In addition, the script provides the tester with detailed expected results to verify the operation of the test script.

In order to plan detailed script steps and expected results, it is necessary to know the test data. A large portion of the test data will typically be contained in test databases. These databases are called baseline databases, and are critical for a repeatable test model to exist. Baseline databases can be developed automatically (through execution of online activity in the system), manually (through test data manipulation tools), extracted from production databases, and so on. Once the baseline databases are selected and created, the repeatable test model can be developed. As the test model is based upon these databases, the impact on the test model of any changes to the baseline databases must be analyzed.

With a repeatable test model, most of the team members' knowledge is captured in the tests. Retention of team members is therefore far less critical than with a non-repeatable test model, and expected costs of training new team members are reduced.

If the application does not change, repeating the tests yields the same results every time, given the same baseline databases. To remain repeatable, a test model must be maintained to reflect changes made to the application (fixes, isolated enhancements, new releases, and so on).

To ensure the quality of the application as well as testing efficiency and effectiveness over time, the tests contained in the test model must be repeatable. Automation facilitates the engagement's ability to execute a repeatable test model. The decision to automate the test execution only affects whether the tests will be repeated manually or automatically.

Automating the execution of a non-repeatable test model is a waste of resources, as the test tool will not be able to re-execute the tests automatically or perform full regression tests with little effort. Little or no benefits will be achieved from automation.

Product Considerations a) Has RTP (Reinventing Testing Project) developed a test plan management system?

b) What tools can be used for problem tracking?

The RTP Tools Development team has documented their evaluation summaries of the internal test plan management system. The following is a brief description of the product.

The Test Plan Management System is an online GUI application that is used to facilitate the creation and maintenance of test models and to support the planning and performing of each test stage. Each test model is stored in a central repository accessible by all team members.

Any test model data must be manually entered in the system or copied from a previously entered test model.

Multiple test models can be accessed or viewed at one time.

In addition, the TPMS provides the capability to research previously entered test elements through online queries.

A reporting option is planned to produce metrics and management type reports.

c) What testing team factors should be considered when using a Test Planning tool?

Size of the Testing Team

The larger the testing team, the more benefits will be derived from using a Test Data Management tool (easier control over the test data for the various testers), a Configuration Management tool (easier control over all system configurations and component versions), and a Test Plan Management tool (easier control over all test cycles, subcycles, their operating statuses, and so on).

d) What engagement factors affect the use of Test Planning tools?

Risk Rating of the Engagement

In general, management and planning tools help better address the engagement risks. A high risk rating for the engagement will affect positively the decision to use tools such as Test Planning, test data management, problem management, and configuration management.

Criticality of the Engagement

In general, management and planning tools help better manage the engagement and ensure the timely delivery of a quality system. Therefore, dealing with a highly critical engagement will most likely affect positively the decision to use tools such as Test Planning, test data management, problem management, and configuration management.

e) What application factors should be considered when using a Test Planning tool?

Starting Point of Automation in the Development Life Cycle

If the testing process is to include the use of a test plan management tool, test model components may be more easily reused across test stages resulting in time and cost savings during Test Planning and preparation. This obviously has a positive influence on the decision to use the test plan management tool.

Test Execution

Test Execution tools support and automate the conduct of system tests. Test Execution support includes the tools required to:
  Extract input data and expected results from the repository
  Load this data into the appropriate Test Execution tools
  Automate the test Such tools include dynamic analyzers and execution logs. The Test Execution platform may differ from the development platform if development is conducted in one environment (for example, Windows NT workstations) and deployed on a different environment (UNIX workstations).

A typical Test Execution tool supports test scripting and playback. These tools program or record the running of a test plan in an online environment by capturing key stroke sequences, mouse clicks, and other actions. They then record them in a script. Once the script is programmed or recorded, it can run repeatedly on the same application, effectively emulating the user. While defining the script takes some time, it saves tremendous effort when cycles must be re-run, particularly after relatively small changes (for example, the format of an output field is modified). When the application is modified, the script can be updated directly without re-entering long sequences of user input. This makes it easier to prepare for regression testing. Scripts may also be used for stress testing, where a single machine can run scripts simultaneously, emulating large numbers of users.

Implementation Considerations a) What development approach factors should be considered when automating Test Execution?

Reinventing Testing Project (RTP) has identified the following factors that either contribute to or take away from the successful implementation of an automated Test Execution tool. Further detail is available through RTP's Test Automation Strategy—Version 1.1. The type of system development approach to be considered is:
  Maturity of the testing process
  Number of technical platforms b) What testing tool factors should be considered when automating Test Execution?

RTP has identified the following factors that will either contribute to or take away from the successful implementation of an automated Test Execution tool. Further detail is available through RTP's Test Automation Strategy—Version 1.1. Testing tool factors to be considered include:
  Cost of testing tools (including training and support)
  Cost of test model maintenance (including test data)
  Testing tool ability to work with GUI application builder
  Vendor support capability
  Proximity of vendor support personnel to the project site
  Availability of tool support person on the testing team c) What engagement factors should be considered when automating Test Execution?

RTP has identified the following factors that will either contribute to or take away from the successful implementation of an automated Test Execution tool. Further detail is available through RTP's Test Automation Strategy—Version 1.1. Engagement factors to be considered include:
  Fixed fee engagement
  Risk rating of the engagement
  Criticality of the engagement
  Risk of not automating testing d) What application factors should be considered when automating Test Execution?

RTP has identified the following factors that will either contribute to or take away from the successful implementation of an automated Test Execution tool. Application factors to be considered include:
  Application life expectancy
  Number of planned releases
  Use of application software packages
  Frequency of upgrades in application software, system software, and hardware
  Stability of the application
  Starting point of automation in the development life cycle
  Scope of the test automation
  Number of passes per test cycle e) What testing team factors should be considered when automating Test Execution?

RTP has identified the following factors that will either contribute to or take away from the successful implementation of an automated Test Execution tool. Further detail is available through RTP's Test Automation Strategy—Version 1.1. Testing team factors to be considered include:
  Willingness and ability to maintain the test model
  Communication between development team and testing team
  Control over the test environment
  Acceptance of automation (attitude toward change)
  Experience with test automation
  Experience with the testing process used on the engagement
  Experience with specific testing tools
  Anticipated learning curve with automated testing tools
  Experience with the technology used on the engagement
  Size of the testing team Performance Management Performance Management tools support application performance testing. Owing to the large number of components in modern systems, performance modeling can be a complex task and requires tools to effectively manage the process. These tools monitor the real-time execution and performance of software. They help to maximize transactions and response time to the end user. They are also useful in identifying potential bottlenecks or processing anomalies.

In the case of Internet-based applications, as the Internet is not a controlled environment, performance management tools can only measure performance within the domain of the controlled environment (up to the Internet Service Provider). However, in the case of intranet-based systems, where the environment is controlled from end-to-end, Performance Management may be performed across the entire system.

Emulation

Emulation tools emulate components that are part of the target environment but are not in the development environment. These emulation tools include:
Target platform architecture components, including both custom infrastructure and system software products such as an X-window emulator on a PC to access a Unix platform.
Stubs, which emulate subroutines in a minimal fashion.
Harnesses and drivers, which call up a module and emulate the context in which the module will be called in the production environment.

Test Result Comparison

Test Result Comparison tools are utilities used to compare expected and actual results. These tools outline the differences between actual and expected results by comparing files and databases. Most of these tools offer functionality such as byte-by-byte comparison of files and the ability to mask certain fields such as date and time.

Test Coverage Measurement

Test Coverage Measurement tools are used to analyze which parts of each module are used during the test. Coverage analyzing tools are active during program operation and provide comprehensive information about how many times each logic path within the program is run. This Test Management and Quality Management tool ensures that all components of an application are tested, and its use is a vital and often overlooked component of the test process.

SIR Management

SIR Management Tools help track each system investigation request from problem detection through documentation resolution.

Operations Architecture Framework (2000)

Operations Architecture

Figure 20:
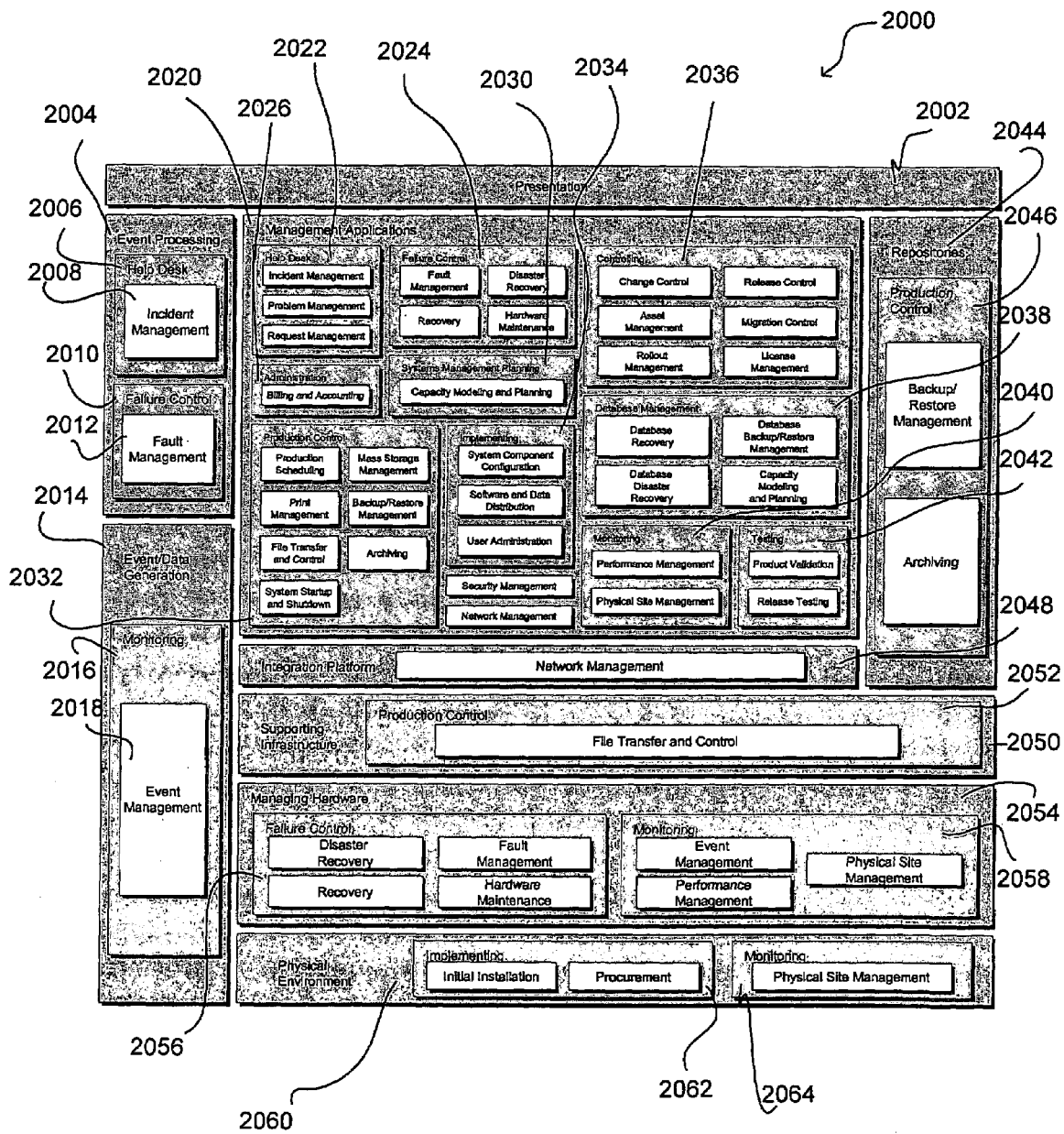
FIG. 20 is an illustration showing an Operational Architecture Framework in accordance with one embodiment of the present invention.

As shown in FIG. 20, the Operations Architecture is a combination of tools, support services, procedures, and controls required to keep a production system up and running efficiently. Unlike the Execution and Development Architectures, its primary users are the system administrators and the production support personnel.

The following databases provide information on the Operations Architecture and list requirements and current tools solutions for the managing of the various Operations Architecture areas. All areas of the Operations Architecture have the appropriate MODE sub-functions listed, along with requirements for management solutions and current tools that assist and automate management solutions.

Cautions and Caveats

Unlike the Application and Execution Architectures, every function of the Operations Architecture must be reviewed. All components of the Operations Architecture are integral to the successful management of a distributed environment. Any processes, procedures, or tools developed or chosen as an operational management solution for a specific operational area must be able to integrate with any existing or planned process, procedure, tool solutions for other Operations Architecture areas.

While the tools data and suite information was current and accurate at the time of publication of this document, there is no guarantee that that information is still accurate, or that the vendor is still in business. It is imperative that the following actions are taken when choosing a tool-based solution:

determine that the vendor is still a viable candidate (i.e. still in business, good recent product support track record)

verify the version of the tool to be installed will still provide the management solution required verify the tool(s) will integrate with existing tool(s)

verify the tool(s) will integrate with other planned tool(s) acquisition(s).

General Implementation Considerations

Some key design decisions are specific to the design of certain functions, while others apply more generically across every function. This section presents the generic key design questions. Key design decisions that relate specifically to a function are presented in each of the subsequent functional grouping chapters.

The following generic decisions impact need for specific components:

When and how frequently, does the function need to be performed?

The timing and frequency of each function may have an effect on its staffing, the tool(s) required, the capacity of systems and networks needed to support the tools.

Who will be performing the function?

Responsibilities need to be defined for each function, as the set up tasks will differ dramatically depending on whether the function is to be performed in-house or outsourced. In addition, the individuals who will be performing the function should be involved in the design of how the function will be performed.

Will the function be centralized or distributed?

Central control will mean a stronger focus on remote management, with skills focused in one place, whereas distributed control will mean skills will need to be more widely dispersed. Distributed functions may require less powerful tools due to their placement.

Will the solution be manual or automated?

A number of functions could be managed manually, especially if the functions are not directly related to the systems, or are performed infrequently. Many of the functions, however, require an interface to the systems, or involve large volumes of data.

Is integration with any existing systems required?

If integration with existing systems is necessary, hooks may need to be built into both the existing and new systems.

What are the data sharing requirements with other functions?

Integration between functions will either require a tool capable of supporting both functions, or hooks between tools.

What are the expected data/transaction volumes, and how much historical data will be required?

Volumes of data, both real-time and historical, will have an impact on both system and network sizing.

What platform/protocol constraints exist?

Platforms and protocols are central both to the overall approach as well as the selection of tools to support the individual functions.

Is the intention to use tools or to custom develop some or all of the functions?

The choice of tools in the marketplace is increasing, but custom development may still be required. This decision will impact how the function is established initially as well as its ongoing support and maintenance.

Will existing data/databases be used, or will data be built from scratch?

Many of the functions may already exist within the clients environment. As such, data which is necessary for supporting the system may already exist. If so, it must be determined whether or not the existing data can be used, either in its original or a converted state.

General Product Selection Considerations

It is important to note that there may be requirements which cannot be met by any tools. In this case, in-house development may be an alternative. This approach is likely to be more expensive, however, and more difficult to support the long term, and thus should usually be avoided if possible. Were possible, the tool with the closest match should be purchased, and customized to meet the necessary requirements.

Some additional considerations are outlined below:

Central vs. Distributed Control

The answer to this question may limit the selection of tools as not all tools are capable of controlling functions remotely. If control is centralized, technical expertise at distributed sites will not be necessary. This may, however, mean that a more complex, expensive tool is required.

If control is distributed, technical expertise will be needed at remote sites, and there is the potential for problems with the interfaces between tools.

Platform Constraints

Systems-based tools (e.g., for monitoring or control purposes) will clearly be platform dependent. Functional tools (e.g., to support Incident Management or Change Control), however, can run independently from the systems tools and may only need to run on a limited number of systems.

Integration with Other Functions

Integration between some of the functions is highly desirable. Integrated toolsets offer integrated functionality across a number of functions, thus simplifying the interfaces between them (e.g., data will automatically be consistent across functions). Purchase of such tools will help reduce costly customization or the development of add-ons.

It is important to understand the level of integration between products, however, before buying them. Integration varies from vendor to vendor and can mean anything from simply having an icon on a desktop to fully integrated applications and data. In addition, integrated toolsets are likely to be stronger in some functions than in others, and may preclude selection of the best possible tool for every function.

Anticipated Volume of Data & Transaction Throughput

Understanding the anticipated volumes will provide key input to sizing the system. Predicted business volumes stated in the SLA should be used to help determine the appropriate sizes for machines, databases, telecommunications lines, etc. Alternatively, experience from previous engagements can provide useful input.

Number of Users for the Tool

Users may not be limited to the number of support personnel accessing a tool alone. Keep in mind that users of the tools may either be support personnel, vendors, users, senior managers, etc.

Some tools will only support a limited number of users, or may only support users within certain geographic boundaries. It is important to understand if there are any such limitations prior to purchasing a tool.

In addition, the number of users will affect the budgetary requirements for the purchase of a tool, particularly as they relate to hardware and communications requirements.

Level of Support Required

If third party software is to be purchased, suppliers must be assessed on their ability to ensure the availability, reliability, performance and user support for these tools will be sufficient to deliver the appropriate levels of service to the users of the system. It may even be necessary to visit reference sites for the vendors to determine whether these requirements are being met.

Presentation (2002)

The presentation component provides the interface between the manager(s) of the system and management data generated by the system. Data can be manipulated for various forms of output. By integrating the operational architecture it is possible to reduce the number of front-end interfaces required. Commonly, the presentation component uses a GUI front-end interface. This component is also responsible for real-time and historical report generation.

Event Processing (2004)

Event processing manipulates the raw data obtained in the event/data generation layer into a more workable form. This layer performs functions such as event filtering, alert generation, event correlation, event collection and logging, and automated trouble ticket generation. Event processing routes the processed information on to either the presentation or management applications layers. Again it is important to consider the interface of the event processing component with the other components of the operational architecture.

Help Desk (2006)

As with End User Services in the centralized model, the Help Desk is the single point of contact for all end users. This unit has end-to-end accountability for all user incidents and problems regardless of whether or not it has the resources to fix them (i.e., it must contact the necessary technical resources in either IS organizations to ensure the incidents and problems get resolved).

Incident Management (2008)

Incident Management provides the interface between the users of the system and those operating and maintaining the system when an incident arises. Incident Management is responsible for:
  receiving incidents from users
  informing users of known work-around where possible
  ensuring that support personnel are working on an incident
  keeping users informed of incident resolution progress
  ensuring that incidents do not get lost as they are passed around support teams
  informing users when incidents have been resolved and ensuring resolution was complete.

In addition, Incident Management is responsible for ensuring that outstanding incidents are resolved in a timely manner. As part of Incident Management, incidents are reviewed, analyzed, tracked, escalated as necessary, and resolved.

Failure Control (2010)

Involves the detection and correction of faults within the system whether they be minor (e.g., workstation is down) or major (i.e., a disaster) has occurred.

Fault Management (2012)

When a negative event has been brought to the attention of the system, actions are undertaken within Fault Management to define, diagnose, and correct the fault. Although it may be possible to automate this process, human intervention may be required to perform at least some of these management tasks.

Event/Data Generation (2014)

Event/data generation interacts with all the managed components in the execution and development environments in order to obtain the required management information. This component also interacts with the physical environment, managing hardware, and supporting infrastructure components of the operational architecture to obtain management information. It is important to consider these interfaces when choosing event/data generation components. Agents and proxies are two common types of event/data generation tools. Often these tools use broadcasting and trapping methods to capture information. Application generated events from vendor packages and user applications also fit into this component of the operational architecture.

Monitoring (2016)

Verifies that the system is continually functioning in accordance with whatever service levels are defined.

Event Management (2018)

An event is an electronic message generated by any component (e.g., application software, system software, hardware, etc.) in the system. Event Management receives, logs, classifies and presents event messages on a console(s) based on pre-established filters or thresholds.

Management Applications (2020)

Management applications are those tools which are used to manage the system. Most of the MODE functions tie directly into this component. The management applications component ties in directly with the integration platform component as the management applications tools must comply with the standards set by the integration platform. For example, if the integration platform is HP Open View, then the management applications must be HP OpenView software (API, SNMPx) or hardware (card) compliant. Management applications receive data from the event/data generation, event processing, and repositories components and then send data to the presentation or repositories components. Management applications tools include capacity planning tools, performance management tools, license management tools, remote management tools, systems monitoring tools, scheduling tools, help desk tools, etc. Some Enterprise Management tools even poll the event/data generators for information but these options may impact network performance. Web Server management is been introduced as part of the management operations framework. As Corporate Internets and Extranets implement Web based software products to sell and advertise business services, corresponding administrative, security, event notification and performance requirements must be performed similarly for the companies web based system. The critical path issues for Web based server software is typically security and performance based levels of service.

Help Desk (2022)

As with End User Services in the centralized model, the Help Desk is the single point of contact for all end users. This unit has end-to-end accountability for all user incidents and problems regardless of whether or not it has the resources to fix them (i.e., it must contact the necessary technical resources in either IS organizations to ensure the incidents and problems get resolved).

Implementation Considerations

The following are functional requirements for Incident, Request and Problem Management.

Logging Incidents/Requests

Call logger should be presented with a unique incident/request identifier, and should be able to enter a free format description as well as the key data items specified in the data requirements section. Data and time stamps should be automatically registered and Incident and Request management staff should have access to display all open incidents and requests as well as the incident/request history for a specific user location.

Progress Incidents/Requests

Facilities should be given to provide a free format update of actions and investigations, to assign the incident/request to a support group, or to escalate the incident. Date and time stamps should be attached to each action and the full incident/request history should be available to the person performing the update.

Re-Assign Incidents/Requests

Possible for incidents and requests to be assigned to different support groups, if further investigation is required.

Close Incidents/Requests

Incidents and requests should be closed with a date and time stamp to help trend analysis and service level reporting.

Log Problems

Problems can be logged both as a result of one or more incidents, or through proactive monitoring of the system, before any incidents have been logged.

Support the Functions Either Centrally or on a Distributed Basis

If the Incident, Request and Problem management functions are to be centralized, these functions need to be able to control and monitor incidents and problems, but other functions should be able to gain access to input detailed technical information or progress updates. If Incident and Request management is distributed, it is recommended that remote locations are given access to the central system, rather than operating local systems. (Some problem areas are local sites operating on different time zones and standardizing escalation procedures from local sites.)

Facility for Auto-Logging Incidents

Event/alert based automatic logging of incidents to provide proactive management of incidents and problems by informing Incident management of issues before the user logs a call. This facility is conceptually desirable, but is only likely to be available if the Incident management functionality is part of the monitoring tool. The costs of building hooks between tools and applications are likely to prove prohibitive. In medium or large environments, this facility is extremely desirable, and must be built into the requirements.

Assess Incidents Automatically, Based on Previous Experience and Rules

Knowledge and case based incident management systems are becoming prevalent in the market place, and are built into Help Desk offerings. Use of these systems can help improve the responsiveness and reputation of the entire organization. (Case based tools will require building up over time.)

Incident Management

Incident Management provides the interface between the users of the system and those operating and maintaining the system when an incident arises. Incident Management is responsible for:
- receiving incidents from users
- informing users of known work-around where possible
- ensuring that support personnel are working on an incident
- keeping users informed of incident resolution progress
- ensuring that incidents do not get lost as they are passed around support teams
- informing users when incidents have been resolved and ensuring resolution was complete.

In addition, Incident Management is responsible for ensuring that outstanding incidents are resolved in a timely manner. As part of Incident Management, incidents are reviewed, analyzed, tracked, escalated as necessary, and resolved.

Implementation Considerations

Will users be given access to the Incident Management system?

Users will benefit by gaining up to date information on the progress of incidents, and could be given the facility to log incidents directly, which would relieve some of the load of the Incident Management function. However, this adds complexity to the solution, and increases communications requirements/costs.

Which support personnel will be given access to the Incident Management system?

Support personnel would be able to enter progress against incidents without contacting Incident Management. The ability to scan incidents may also aid the Problem Management function. However, this adds complexity to the solution, and may increase communications requirements/costs.

How many incident support levels will be in place, and how expert will the Incident Management function be?

This will depend on the knowledge and experience at the user locations. The level of technical expertise within the Incident Management function will drive the systems requirements.

Problem Management

Problem Management utilizes the skills of experts and support groups to fix and prevent recurring incidents by determining and fixing the underlying problems causing those incidents. Within Problem Management, related incidents are correlated to problems and ultimately to order or change requests. All problems are logged, tracked and archived. Where possible, work-around are determined and information regarding the work-around is distributed to the appropriate support personnel and user communities.

Implementation Considerations

Will problems be automatically logged or only by manual association with an incident?

Automatic logging of problems will require interfaces to be built with the Event Management system, and perhaps the execution architecture for application errors.

Request Management

Request Management is responsible for coordinating and controlling all activities necessary to fulfill a request from either a user, vendor, or developer. Request Management determines if and when requests will be fulfilled through interaction with the particular function(s) impacted by the request. Following such interaction, accepted requests will be planned, executed, and tracked.

Implementation Considerations

Will users be given access to the Request Management system?

Users will benefit by gaining up to date information on the progress of incidents, and could be given the facility to log incidents directly, which would relieve some of the load of the Incident Management function. However, this adds complexity to the solution, and increases communications requirements/costs.

Failure Control (2024)

Involves the detection and correction of faults within the system whether they be minor (e.g., workstation is down) or major (i.e., a disaster) has occurred.

Fault Management

When a negative event has been brought to the attention of the system, actions are undertaken within Fault Management to define, diagnose, and correct the fault. Although it may be possible to automate this process, human intervention may be required to perform at least some of these management tasks.

Disaster Recovery

In the event of a significant system failure, Disaster Recovery processes will be invoked to re-route the system resources to a secondary, stable configuration until the primary resources can be restored. Within a distributed environment, disaster recovery must account for differing levels of disaster whether at a central or distributed site(s).

Implementation Considerations

What is a disaster?

The way in which a disaster is defined will be dependent upon which resources are critical to the business. For example, a data center failure may be critical for one client whereas a server failure for another is more critical.

How quickly will disaster recovery be required for each service?

This will be defined in detail within the SLA, but high level service recovery targets must be understood, so that high level recovery plans can, in turn, be produced.

Recovery

Recovery manages all of the actions needed to restore service delivery after a system failure. With critical business applications being rolled out on distributed technologies, the recovery of these systems must be easy, quick and efficient to guarantee availability of core business systems as expressed in the agreed service levels and operational levels.

Implementation Considerations

What are some of the limitations that are encountered?

Recovery capabilities span the range from those required to bring up a device after it has failed to those required in the event of a major disaster. With critical business applications being rolled out on distributed technologies, the recovery of these systems must be easy, quick and efficient. Loss of the system for even a short period of time can result in significant financial losses to a clients business.

Hardware Maintenance

Hardware Maintenance maintains all of the components within a distributed system to protect the investment of the organization. Generally agreed upon in the SLAs, maintenance contracts are carried out, monitored and recorded for each asset as appropriate.

Administration (2026)

Billing and Accounting

Billing & Accounting gathers the necessary accounting information for calculating actual costs, determines charge-back costs based on pre-defined algorithms and bills users for service rendered.

Billing & Accounting also makes payments to service providers for services and equipment provided in accordance with agreed upon SLAs. As part of this payment process Billing & Accounting reconciles bills from service providers against monitored costs and SLA/OLA violations.

Systems Management Planning (2030)

Capacity Modeling and Planning

Capacity Modeling & Planning ensures that adequate resources will be in place to meet the SLA requirements, keeping in mind operational requirements which may require additional capacity. Resources can include such things as physical facilities, computers, memory/disk space, communications lines and personnel. Through this component, changes to the existing environment will be determined, modeled and planned according to the necessary requirements.

Production Control (2032)

Ensures that production activities are performed and controlled as required and as intended.

Production Scheduling

Production Scheduling determines the requirements for the execution of scheduled jobs across a distributed environment. A production schedule is then planned to meet these requirements, taking into consideration other processes occurring throughout the distributed environment (e.g., software and data distribution, remote backup/restoration of data.) It plans the production workload and then submits the tasks to the system in the proper sequence, stops processing upon detecting a failure, provides on-line task tracking and workload forecasting.

Implementation Considerations

In a distributed environment are processes across entire or multiple platforms and systems?

Processes may be taking place across the entire system on multiple platforms in either a parallel or a serial fashion. Batch dependencies may be required across platforms, and multiple time zones may be involved. In addition, many non-mainframe based products do not provide production scheduling capabilities with the platform. Therefore, one can see that scheduling processes across a distributed environment can be quite complex, requiring significant management effort to ensure that processes occur appropriately.

How many schedulers will be used to control the schedules?

Depending on how the function is to be controlled, and how many platforms are to be supported:

Local control of a single device with a single scheduler (typically mainframe)

Remote control of a single device with a single scheduler

Remote control of multiple but independent devices with a single scheduler

Product Considerations

What is the Intended use of the tool?

The component plans for the production workload and then submits the tasks to the system in the proper sequence, stops processing upon detecting a failure, provides on-line task tracking and workload forecasting. In addition, requirements are determined for the execution of scheduled jobs across the environment.

Does and existing component satisfy this requirement?

Production Scheduling contains specific requirements that addresses a distributed environments complexity of multiple platforms and system placed in either a parallel or serial fashion.

What other utilities are available with the tool?

The tool should provide control dependencies to schedule workloads such as: Task/job sequence enforcement, external/internal event driven. Graphically displays work flow from the scheduling criteria and includes such information as task/job name, task description, average run time and resource requirements. Allow clients to define user schedules that can be based on predecessor events in the production environment. Reporting capabilities for forecasting, simulation and analyzing scheduled workload. Monitoring capability of past, present and future workloads as well as tracking of current workload termination notification of normal or abnormal completion.

Does the development team have any prior experience with the tool?

The development should be able to identify the component linkages as well as the functional requirements critical for successful operational integration of the tool into the observed environment.

What level of the component is required?

Due to the complexity of a distributed environment one must account for the processes taking place across the entire system on multiple platforms in either a parallel or a serial fashion. Therefore, production scheduling capabilities across platforms is critical as well as the ability to rerun/restart from single point of failure or provide checkpoint restart-ability.

Does the tool provide facilities to add color to MODE architecture model?

- Communication with Performance management component to forecast resource requirements, such as near line storage, DASD space, and etc.
- Interface with the Configuration management component facility to obtain configuration data in workload forecasting.
- The scheduler will communicate with other schedulers on other systems to run a in a close relationship with the ability to support multiple heterogeneous platforms: MVS, Windows NT, UNIX, and AS/400.
- Communicates with Backup/Restore to identify scheduling constraints due to backup and restoration functions.
- Communicates with the recovery facility to dynamically switch workload from one processor to another in the event of a system failure.

Print Management

Print Management monitors all of the printing done across a distributed environment and is responsible for managing the printers and printing at both central and remote locations. The purpose of a print architecture is to make formats applications independent, so that the only thing applications need to do is obtain the data.

Print Architecture offers:

It provides independence from printer devices and languages

It makes it easy to develop and maintain report

Paper consumption may be reduced

Reports arrive to the addressee more quickly

It is possible to sign reports electronically

Confidentiality is improved as people can only see information that can be accessed with their security level.

Implementation Considerations

What types of printers will be required (e.g., laser, impact, inkjets, etc.)?

The types of printers will be dictated by the business requirements. The types of printers, will in turn, determine what tools can be used to manage printing may or may not be required.

Where are the printers going to be located?

The business will help determine where the printers need to be located based on where/when printing needs to take place. In some instances local printing may or may not be required.

What spooling facilities will be available?

If spooling is available, printing can be handled as a background task, freeing up system resources for use on-line.

Will review before print facilities be provided?

If these facilities will be provided, all material will not need to be printed. If the material does need to be print; however, the location of the printing must be determined, and the system must be able to forward the printing on to the appropriate location.

Will printing of large documents be necessary?

Large print jobs may utilize system resources considerably (e.g., WAN, LAN, printer), and may tie up the printing queue for other individuals. This type of printing should be performed in off-hours or delayed to avoid contention for the printer during business hours.

What are some limitations that may be encountered?

In a distributed environment the sizing and routing of print traffic is more complex. With new systems being installed, only educated guesses about how and when printing will take place can help determine print routing functionality. In most cases, some adjustments will be required to the print routing algorithms post-rollout to reflect the printing reality.

Product Considerations

What is the intended use of the tool?

Controls report production and distribution form the moment the report is created to the time the printed report is dropped in the end-use s mailbox (electronic, paper, microfiche, etc.)

What other utilities are available with the tool?

Provide queue management and ability to prioritize.

Provides a full featured on-line viewing system.

Provides for the archival of re ports in a compressed format first on disk, for a user specified time and then to tape of optical.

Process reports in due-out-sequence.

Automatic report balancing and archives the balancing reports for easy auditor review.

Provides a common output spooling and printer device control capability across the network.

Provide report reprint capability, avoid reruns in lost report situations.

Provide centralized management of report setup and delivery information

How well does the tool integrate with other tools in the environment?

Interfaces with the performance monitoring to identify bottlenecks in the distribution process Notifies the service level management facility of any missed service commitments.

Communicates with the documentation management facility to obtain the distribution information, media type and service level commitments.

Communicates with the recovery management facility to delete reports that will be recreated.

Communicates report volumes to the resource consumption management facility.

Does the tool provide support for specific areas?

Support multiple printer types as well as report delivery across them. This includes printer format translation (PCL, Postscript, etc.) and code translation.

Any other specific functional requirements?

Output management issues require leverage of existing print capability, local and remote printing, and distribution management through a software package or an equivalent alternative.

File Transfer & Control

File Transfer and Control initiates and monitors files being transferred throughout the system as part of the business processing (e.g., nightly batch runs). File transfers may occur between any two or more devises within the system.

System Startup & Shutdown

System Startup and Shutdown performs the activities required for the startup or shutdown of the entire system (e.g., hardware, applications), or portions of the system depending upon the identified requirements. Within a distributed environment, the system includes both centralized and remote resources.

Implementation Considerations

Will devices need to be shutdown/started remotely as well as be automatic or manual (e.g., using scripts, embedded in schedule)?

If expertise will not be available locally, it is imperative that remote control of the startup/shutdown processes be available. The presence of skills, the availability of tools, and the uniqueness of the application/environment will dictate whether or not startup/shutdown is automatic or manual.

How will clean shutdowns of all processes be ensured?

If a system failure takes place, it is important that all processes be shut down well, to ensure that the processes can be re-started and that the integrity of the information will be maintained.

In what order will hardware and software components be started/shutdown?

Based upon the technical requirements of the system (e.g., databases should be started before applications) as well as defined service levels (e.g., one particular application is critical and must be started first), the order of startup/shutdown will be determined.

Are periodic re-boots required (e.g., to clean up memory)?

If this is necessary, automatic/manual startup/shutdown of the system should be scheduled (e.g., UNIX systems require this).

Analysis of the system and other resources need to be addressed?

The state of an application, the system or a specific resource must be known at all times. Common activities performed as part of Startup/Shutdown include:

logging on virus checking version checking process initiation/completion housekeeping logging off.

Some limitations that may need to be taken into account?

System startup and shutdown is no longer confined to a centralized site. The system is distributed, in effect creating islands of technology which may be started or shutdown with the flip of a power switch on a workstation. Processes which rely on the system being up and running (e.g., software and data distribution) may fail if a user has switched his/her machine off before leaving for the evening. Such failures will impact the following days processing capabilities and must be accounted for either by the system or through training. In addition, controlled machine startup may be required to initiate tasks or to perform activities such as configuration checking or virus detection/correction.

Mass Storage Management

Mass Storage Management involves those: activities related to the handling of various types of centralized and distributed storage media including the monitoring and controlling of storage resources and their usage.

The objectives of Mass Storage management are to: implement the top level of storage management, control the usage level of each storage device in the distributed environment, control all storage related naming standards and placement details in the installation.

Mass Storage Management is more complex in a distributed environment than in a centralized environment since many more storage options become available, as storage may take place centrally or on a distributed basis and the number and characteristics of storage devices have increased.

Implementation Considerations

What DBMS will be used and what utilities does it have?

The DBMS will often provide much of the necessary storage management functionality; this decision impacts further requirements.

Will databases be distributed or centralized?

Storage management for centralized databases will clearly be simpler then for distributed databases were a global view becomes more difficult to obtain, and where data consistency becomes more of an issue.

What media types will be used?

It is essential that the types of device to be used are understood before detailed decisions are taken.

Distributed Environmental Constraints?

The allocation and sharing of storage media is more difficult to plan since users are distributed. Mass Storage Management is more complex in a distributed environment as many more storage options become available; storage may take place on disks, tapes, etc. Either centrally or de-centrally.

Product Considerations

What is the Intended use of the tool?

Control and manage the data storage environment including any/all media, disk, optical and tape.

Technology's ability to support the Operating Systems within the distributed environment?

The tool must run in the platform selected in order to control usage of disk space, main memory, cache, etc. In addition, determining the space available helps control the device usage, storage capacity What other utilities are available with the tool?

Continuous analysis of the data storage environment to insure optimum storage utilization and location.

Eliminate fragmentation by reordering files

All storage devices managed independently of their type and location in order to avoid storage problems, bottlenecks, etc.

Should the tool provide specific component functionality?

The tool should take into account the complexity of the distributed environment as well as the flexibility of the scenario that storage may take place centrally or on a distributed basis and the number and characteristics of storage devices have increased.

Does the tool provide support for the databases selected for the distributed environment?

Additional facilities may be required, even although databases typically have built-in utilities or tools to perform these function and do not generally require a separate tool.

Does the tool provide facilities to add color and support linkages to MODE architecture model?

Communicates with the Performance management facility to identify any performance problems and relocate data based on the performance analysis.

Communicates with operation system error logging and/or the Operations Automation to identify any potential media or hardware failures and relocate data, automatically files a problem log for corrective action.

Interface with the Capacity/Resource manager to create a definable resource forecast.

Backup/Restore Management

Backup and Restore Management considers all of the back-up and restorations that need to take place across the distributed system for master copies of data. Depending on the need, these processes may occur centrally or remotely.

Implementation Considerations

What data/files will be backed up?

Files that are either unique, store site specific data or are highly volatile should be backed up. This will help ensure that important, business critical data will not be lost in the event of a system failure or disaster. All files do not necessarily need to be backed up as each file backup utilizes storage space and ma impede the performance of the system.

What will be the frequency of the backup, the number of copies made, and the number of generations maintained?

The critically and volatility of the information will determine the frequency of the backups and whether or not multiple copies of the data are maintained centrally/locally. In addition the stability of the system needs to be considered as well as any performance impacts of backing up the data as required.

The number of generations maintained will be dependent on the disaster recovery policies in place as well as any government/regulatory controls in existence.

How will the integrity of a backup or restore be ensured?

Because databases can be located throughout the distributed environment, care must be taken to ensure that data integrity is maintained. This may mean storing the master copy of data centrally, or synchronizing the commits of updates of the information appropriately.

Will the data be backed up centrally, locally, or at an alternate site?

Centrally located devices will require the use of both LAN and WAN bandwidth to backup the data, and restoration of the data will be slower. This may be hard to achieve if there are numerous devices in the system. Central location, however, will ensure that backed up data will be stored in one place, potentially making recovery from a system failure or disaster recovery easier as well as centrally less expensive to maintain. In addition, central control over the backup/restore process will require expertise at a single location whereas local control will necessitate expertise in multiple locations. Alternate site control may provide the best mix of central/local placement of skills.

In contrast, local devices do not utilize the WAN bandwidth, and typically provide faster data restoration. Local devices, if available, may be more expensive and may require local expertise.

Alternate site backup combines both of the strategies in that WAN bandwidth to the central site is not over-utilized, and restoration of the data can happen fairly quickly as well as securing information as information is stored in multiple locations.

Will copies be held at multiple locations?

Backup copies may need to be stored at multiple locations for security purposes (i.e. in the event of a system failure, or disaster, some backup copies may have been destroyed.)

Product Considerations

What is the intended use of the tool?

Provide services and facilities to enable the client to effect timely and accurate recovery in the event of an interruption to processing capability.

What other utilities are available with the tool?

The backup product should have fundamental management capabilities. Automatic restore, unattended operation and command line processing of the product should be available. Basic tape functions such as cataloging, internal labeling, initialization, certification, scratch protection and write protection are musts.

Performs automatic backup of data files on site standards.

Designed along the lines requester-server model; more specifically the tool runs on the server machine and acts as a shared resource for data access, integrity, security recovery, etc.

Full auditing capability should be present for backups as well as error detection and notification that a backup has failed should be available.

Provide full and incremental backups, partial restore, and compression/decompression.

Capable of managed and systematic restore process.

How well does the tool integrate with other tools in the environment?

Backups are typically embedded into production scheduling with restores on an ad hoc basis. Backup/Restore needs to ensure that a file can be only backed up/restored by users with the right access level. Furthermore, file transfer utilities need to be used when the information to archived is sent through the network as well as security for file control access and global authorization should be available and done in concert with the security management facility.

Should the tool provide specific component functionality?

Database backup/restore is inherently more complex than backup of standard files. It is important to ensure that all relationships are resurrected after restoring database files. (Integrated with the functionality of the DBMS)

Does the tool provide support to specific areas?

The product should support multiple heterogeneous platforms: Windows NT, AS/400, MVS and UNIX.

Software features of the product should support items such as direct file access, direct volume access and extended attributes. The ability to backup the operating system files. Support should also handle open file backups either waiting and retrying or taking a fuzzy backup.

Dual logging support in the DBMS is required, both for online and archived logs.

Pint in time recovery of database and database components must be supported.

Ability to support various types of storage devices (magnetic disc, cartridge, tape, optical disc.)

Does the tool provide support for a specific environment?

The ability to support unattended operations reduces the need for operations expertise in both central and remote locations Does the tool add color to MODE architecture model through performance measures?

Performance of the backup product is essential. The tool should backup all production data in the processing window provided and the restore capability should match availability and disaster recovery requirements. Performance can be enhanced through the ability to throttle the backup process to reduce network traffic.

Archiving

Archiving saves and stores information across the distributed environment, either centrally or in distributed locations. Archiving moves datasets, files, etc. from one device to another, usually lower speed, device based on a number of parameters.

Archiving can be used to move information to or from distributed and centralized sites.

Implementation Considerations

Which files and databases will be archived?

Some files and databases need to be stored on fast devices so users can access them quickly. In addition, certain files may need to be maintained for either historic or government/regulatory reasons.

What media will be used for archiving?

The cost of the media, space available and its performance capabilities should determine which archiving medium is used as well as the existence of central or local expertise.

How long should archived data be maintained?

It is important to define the maximum time that data needs to be stored before being deleted, including the number of generations that need to be maintained. This is because the amount of archival space should be determined up front. The maximum time will likely be determined by either government/regulatory controls or disaster recovery requirements.

How will the integrity of retrieved data or files be ensured?

Because databases can be located throughout the distributed environment, care must be taken to ensure that data integrity is maintained. This may mean storing the master copy of data centrally, or synchronizing the commits or updated of the information appropriately.

Will archiving devices reside centrally or locally?

Central control over the archiving process will require expertise at a single location whereas local control will necessitate expertise in multiple locations.

Centrally located devices will require the use of both LAN and WAN bandwidth to archive the data, and retrieval of the data will be slower. This may be difficult to achieve if there are numerous devices in the system. Central location, however, will ensure that archived data will be stored in one place, potentially making recovery from a system failure or disaster recovery easier. In addition, central devices may be less expensive to maintain.

In contrast, local devices do not utilize the WAN bandwidth, and typically provide faster data retrieval. Local devices, if available, may be more expensive, and may require local expertise.

Implementing (2034)

Executes change within the distributed environment with tested components and techniques according to the appropriate plan(s). Implementing includes such things as: initial installation, software & data distribution, license management, etc.

System Component Configuration

System Component Configuration provides a mechanism to configure equipment (i.e., hardware and software) which has configuration parameters to set and to manage the inter-relationships between configured components within the system. Configuration information for particular equipment must be coordinated across the system to ensure that all equipment can function together properly.

Implementation Considerations

Where does the function get input from?

Configuration settings can be retrieved from different sources. The release and the rollout schedule will contain a detailed description of equipment and its configuration and can therefore be used as input. Alternatively, the asset inventory system can be updated in advance and then used as an active database to drive the configuring process.

Product Considerations

What is the Intended use of the tool?

Definition and implementation of consistent configurations for all configurable components within the system.

What other utilities are available with the tool?

Hardware and Software should be configured accurately and with minimal business disruption during initial installation.

Ability to re-configure hardware and software both locally and remotely.

How well does the tool integrate with other tools in the environment?

The asset data has to be updated accordingly and must reflect the actual state of hardware and software and all their relationships. Configuration data may be distributed to the device by Software & Data Distribution; therefore, System Component Configuration needs to get access to Software & Data Distribution processes.

Software & Data Distribution

Software and Data Distribution sends out the correct version of the release package to the distribution locations and updates the locations with the contents of the release package (e.g., software, data, configuration information, procedures and training/support materials.)

The software and data distribution mechanism itself updates either the software, data, or configuration information on a machine(s), reports the relative success/failure of the distribution and updates the asset information for the sites/machine(s) affected by the distribution.

Implementation Considerations

What are some limitations that may be encountered?

Training Planning also impacts how well service will be delivered within the distributed environment. The skill sets required by support personnel will change with the introduction of distributed technologies. Support personnel will be required to have greater breadth of knowledge. No longer can an individual simply understand the network or the applications. The intertwined nature of a distributed environment will force individuals to understand, at least at a high-level, how the system fits together. In addition, support personnel will need to have some specialized skills. As no one individual can fully understand the detail behind the entire system, teams of specialized support personnel will be required to work together to a greater extent in these environments. This group interaction may require new skill sets not frequently found in traditional support organizations.

What are some focus areas to determine an appropriate training plan?

The existing skills must be assessed and a forward-thinking training direction must be defined. The training plan will likely emphasize newer technologies and different methods of training with the underlying goal of providing the appropriate level of service as required by the SLAs.

Product Considerations

What is the intended use of the tool?

Support the ability to distribute software components to interdependent, multiple heterogeneous platforms from a single source. The features should be automated and only require minimal operator involvement.

What other utilities are available with the tool?

Centralized control and administration of distribution function.

Backout, configuration restoration capability.

Schedulable, unattended distribution and installation of software.

Ability to generate distribution candidate lists from asset/inventory management database.

Logging of status/failures to centralized system monitoring facility.

Ability to distribute release packages constructed in module control/versioning facility.

Pre-defined installation and de-installation scripts.

Ability to perform complete back-out of all related segments quickly and automatically, without impacting other, successfully installed updates.

Features should include: data compression and decompression, check-pointing, and retry.

Users should be allowed to postpone distribution to their workstation.

What level of the component is required?

The function must be able to access a release library, to identify release packages, release component groups and release components, and to associate the correct version number with these components.

Ability to select destination nodes by certain criteria, such as location, hardware type, standard configuration at these nodes and to address these nodes in the network.

The function must send to and install software and data at remote locations reliably and within an agreed time scale causing minimum disruption.

The function must be able to back out remotely, either as part of the distribution or as a separate process. The mechanism must be able to regress to the previous operable state prior to disruption.

Ability to synchronize data and time between systems.

How well does the tool integrate with other tools in the environment?

Software & Data Distribution needs to access and update asset data in the asset inventory system to reflect implemented changes (automatically). In addition the function may be based on the same file transfer protocol as File Transfer & Control; unless the tools uses their own proprietary file transfer method based on a standard communication protocol.

Does the tool provide support for specific environments?

Specialized functionality to support operation across the wide-area network environment including: parallel distribution and data compression. In addition, support of platform specific functions and capabilities due to awareness of platform specific information resident in the asset/inventory database.

User Administration

User Administration handles the day-to-day tasks involved in administering users on the system. These tasks include such things as: adding new users, changing user Ids, re-establishing user passwords, maintaining groups of users, etc.

Security Management

Security Management controls both physical and logical security for the distributed system. Due to the nature of a distributed environment, security may need to be managed either centrally, remotely or through a combination of the two methods.

Security Management also handles the logging of proper and illegal access, provides a way to audit security information, rectify security breaches and address unauthorized use of the system.

Implementation Considerations

Some limitations that may be encountered?

Security must exist in various levels throughout the system in order to prevent unauthorized access. Security components must be packaged into a security architecture which can be effectively managed by an organization through their security management strategies.

The number of security components required to secure a distributed environment will increase due to the computing power available through the use of these new technologies and the heterogeneity of the environment. Although things such as dial-up access, LAN access, multiple host access, etc. introduce new user capabilities, they simultaneously introduce security risks into the system.

What are the benefits of single logon capabilities?

Due to the number of components, users may be required to have multiple ID(s) and passwords unless the system is designed to allow a user to access all of the required resources through a single logon. As most products on the market typically allow access to only a subset of resources, single logons with multiple ID and password coordination may be difficult to achieve. Issues such as periodic required password changes can be difficult to overcome while maintaining adequate security.

Product Considerations

What is the Intended use of the tool?

Protects all computer resources, facilities and data from accidental or intentional destruction, modification, disclosure and/or misuse.

What other utilities are available with the tool?

One User-ID for access to all software (central point for all security checking).

Maintains a security log and user profile of what was accessed when, from a computer resource, facility and data view point.

Security Administration ability to monitor the activity of a user of resource.

Allows users capability, when authorized, to maintain their own security profiles by individual or group.

Access authority for database objects (data-sets) as they appear outside the DBMS must be controlled.

Database authorities must be manageable at a group/role level.

Single user setup and sign-on capability across all platforms and applications.

Virus protection on all platforms.

Support for external security devices and dial access equipment, etc.

Encrypted flow of security information across the network.

Comprehensive access logging and auditing capability.

Enhanced security capability beyond normally supplied UNIX levels. This includes being able to support scoped UNIX administrative users (root subsets, limited root functionality).

Network Management

Network & Systems Management Planning is responsible for the planning activities involved in running the day-to-day operations and maintenance of the production systems (e.g., capacity planning, performance planning, etc.).

Controlling (2036)

Monitors change to make sure that change is delivered on-time according to established plans, making adjustments to the plan when unforeseen issues or events arise (e.g., rollout management, change control, asset management etc.)

Change Control

Change Control is responsible for coordinating and controlling all change administration activities within the distributed environment (i.e., document, impact, authorize, schedule, implementation control.)

Implementation Considerations

What types of changes will be controlled by Change Control and what is the anticipated volume of changes?

The types of changes Change Control should cope with need to be defined. Changes can range from a minor document change to the introduction of a complete new service. However, moving a workstation from one desk to another may not require a change request.

Design of the function heavily depends on its size. It may be a relatively small environment with little expected change, or it could be a huge distributed system with many locations, many users and many different platforms.

It is easy to underestimate the volume and complexity of changes in a distributed environment. Changes to different platforms can easily become very complex. Experiences from previous engagements should be used to help predict figures. In a typical distributed environment, several hundred changes per month can be expected.

To what extent should Change Control be integrated with the asset inventory system, maintained by Asset Management?

Impact analysis can use Asset Management to get a detailed list of assets which are dependent on the subject to be changed. It may be a mandatory requirement to provide this list before a change request can be accepted.

To what extent should Change Control be integrated with Incident and Problem Management?

Change requests might be closely tied to incidents and problems, thus when a change is implemented, the corresponding incidents and problems can be cleared.

Which media will be used for change request submission?

Pure electronic forms will be easy to forward over different locations, but it is more difficult to include a signature feature for authorization, and it is not easy to attach documents to provide additional information.

Therefore, further paper forms are typically used for raising change requests but the change administrator then stores the most important information in a change request database. The decision will depend primarily on the size of the system.

There are some limitations that may be encountered within a distributed environment.

There will be multiple change drivers including the users, developers/architects and vendors. The change these groups will wish to introduce must be coordinated on a wide-scale basis as the impact of change within these environments is great. Change Control allows the impact of the change to be assessed along with its merits, timescales, etc. It also provides a way of evaluating and rationalizing multiple change requests against one another to determine what changes should actually take place.

Product Considerations

What is the intended use of the tool?

Integrated central repository of source, change and configuration data used to proactively manage all events impacting user service. Manage the process of change activity, while maintaining the integrity of both application development and the production environment. Support change control from the initiation of the change, through production configuration across multiple platforms.

What other utilities are available with the tool?

Change requests need to be registered in the system, with a unique number assigned as well as related incidents and problems.

The system must support update of change requests. Updates may include changing priorities, results of the assessment, and adding a summary of the implementation.

Once a change has been implemented the change administrator must complete the log by closing the change request.

Centralized repository for software releases, including current and back-level generations.

Asset Management

Asset Management ensures that all assets are registered within the inventory system and that detailed information for registered assets is updated and validated throughout the assets lifetime. This information will be required for such activities as managing service levels, managing change, assisting in incident and problem resolution and providing necessary financial information to the organization.

Implementation Considerations

What data will be stored?

There are four options to consider, when designing the scope of the Asset Management function. Usage of the Asset inventory only as a production system database (core database), including hardware devices, software versions loaded in the production environment, their licenses and network configuration data. Thus the asset inventory system only stores the core systems components in the production environment.

In addition to the production system data as describes above, it contains any existing release and release components such as software modules, documents and procedures. It also contains service level agreements and actual figures for user groups and devices, incidents, problems and change requests. It may also contain additional data such as performance data or log of all backups taken.

How will data be kept up-to-date?

This can be achieved by regular and ad hoc audits, using manual and automated procedures. An alternative approach would be to use asset data to drive Software & Data Distribution. The Software & Data Distribution processes would get data from the asset inventory system as input If these processes configured the devices according to the asset inventory it would be up-to-date by definition.

What phases of an assets life cycle should be covered by Asset Management?

It may be appropriate to control assets within the first stage of the life cycle (i.e., from development on) or it my prove more appropriate to implement Asset Management only from the point of delivery.

Product Considerations

What is the intended use of the tool?

Maintain a central repository for all software licenses and assets.

What other utilities are available with the tool?

Software asset tracking by location/server, automatic detection of correct level of software.

Authorize license use.

Perform periodic searches for unlicensed software.

Central inventory system

Ability to back up and archive the asset inventory system

What are some of the inventory maintenance issues that need to be addressed?

Ability to maintain a data model representing the basis for an asset inventory system that reflects the types of assets to be managed and their relationships. The model should be flexible to cope with future structural changes. A record needs to be added to the inventory system when an asset is purchased or created, or when changes to the environment are performed.

How well does the tool integrate with other tools in the environment?

Asset data needed to support various other management functions such as:

Hardware Maintenance
Release Testing
Procurement
Initial Installation
System Component Configuration
Software & Data Distribution.

Does the tool provide support for a specific environment?

Current asset data from the distributed environment needs to be retrieved frequently through regular and ad hoc audits.

Rollout Management

Rollout Management is concerned with delivering new sites or services to existing sites on-time based on the rollout schedule. Rollout Management monitors the rollout progress of all functions against the rollout schedule to ensure that the schedule is maintained. Review of the rollout schedule takes place regularly to determine how well rollout is progressing and to make any adjustments to the rollout schedule based upon any problems or issues which arise.

Implementation Considerations

What are some principles that should be applied in determining rollout planning?

At the beginning of a rollout, the number of incidents can be dramatic. This happens due to initial problems with hardware and system software as well as the unfamiliarity of the users. In addition to an increased support load, support teams will need more time to process an incident and to solve an underling problem since they will need to become familiar with the new service. Once support teams have become familiar with the system and know how to resolve the most common problems, rollout can be accelerated.

Since many problems will occur initially during rollout, it is important to have quick access to support teams and development teams. If sites are close, support personnel can get to the sites quickly. Once the system is more stable, remote installation can occur.

Instead of planning a tight schedule that keeps teams busy all the time, some windows should be left in the schedule to allow catching up time in case of delays. Otherwise, small deviations to the schedule cannot be handled and larger delays to the entire schedule will result.

When rollout continues over a period of time, hardware and system software updates will affect the initial implementation of the system. The service to be implemented itself may also be updated during rollout. Therefore it is important to review hardware and software maintenance and release plans and to reflect these plans in the rollout schedule.

Will the system be rolled out in one big bang or through a phased rollout over a longer period of time?

Rollout of a new service can either be performed at one specific point in time for all locations or phased over a certain period of time. Phased rollout is the preferred approach because it limits the risk of serious business disruptions. In some cases, however, it may be necessary to complete rollout simultaneously for business reasons.

What are some of the limitations encountered in a distributed environment?

Rollout Planning handles the greatest period of change in distributed systems management—system rollout and installation. During rollout every site and every user may be impacted by the changes taking place. Since delivery of the system will affect how well it is received by the users and is oftentimes defined by an SLA(s), delivery of the system must take place smoothly with minimal interruption to the users. This can be challenging when both old and new architecture domains must exist concurrently until the rollout has been completed.

Interdependencies within the schedule must be identified prior to rollout to highlight the importance of the schedule and the effort required from each group involved.

Release Control

Release Control is concerned with delivering a release on-time based upon the release schedule. Release Control monitors the release progress of all activities against the schedule to ensure that the schedule is maintained. Review of the release schedule takes place regularly to determine how well the release is progressing and to make any adjustments to the release schedule based upon any issues or problems which arise.

Implementation Considerations

What will be the versioning strategy?

It is necessary to determine how a release will be named and versioned. The following points should be considered when defining a versioning strategy. The versioning strategy should be kept simple and meaningful. Versions should be applied not only for complete releases, but for all logical groups of release components as defined in the release definition data model. Asset Management needs to reflect the release component data model in order to be able to store the asset information. In addition, the versioning strategy will affect Software & Data Distribution to ensure that the appropriate version of software/data is resident on the unit prior to implementing the new release, and co-requisite checking ensures that implementations of software/data will leave a machine in a valid state.

How frequently should new releases be packaged?

A minimum time interval between two regular releases needs to be defined. Most planned releases typically occur within three to six months of one another.

Will delta releases be allowed?

The need for delta releases as part of the overall policy must be determined. Delta releases are high risk, as they require a much better understanding of what is already implemented.

Delta releases have the advantage of requiring less storage space on the target machine but it may be more difficult to ensure that the base components are compatible. This can become a particular problem when many components have changed and several delta releases have accumulated.

Will simultaneous changes across platforms be required?

Implementing releases in a distributed environment requires complex synchronization across machines and platforms. An appropriate strategy needs to be determined.

What are some limitations that may be encountered at distributed sites?

Release Planning coordinates the release of updates (e.g., software, data, procedures, etc.) to the distributed sites. An application, for instance, can no longer be delivered upon successful completion of its system test. This is due to the fact that any change in the distributed environment will impact other components in the distributed environment. Releases must therefore be planned carefully to ensure that a change will not negatively impact the distributed system.

Product Considerations

What is the intended use of the tool?

Monitoring and delivery of releases as well as review of release schedule versus planned schedule.

What other utilities are available with the tool?

Provide management of source code, objects, executables, graphics, and documentation.

Track and manage multiple versions of an application, such as development, staging, certification, production, and prior versions of production.

Provide automatic file versioning, configuration versioning, release control, change tracking, etc.

Populate multiple platforms with the correct code at the same time or on schedule, and provide update status.

Confirmation of release scheduling and determine if the release is on schedule and report on progress of release.

If schedules have to be changed, changes need to be authorized by all involved functions and components.

How well does the tool integrate with other tools in the environment

Release Planning and Release Control naturally use the same tool, typically a spreadsheet, for creating and maintaining the release schedule.

Migration Control

Migration Control is a function underneath Release Control. Updates to the distributed system must be tested prior to being released into the distributed environment. To control the updates as the move from the development into the production environment, Migration Control ensures that the proper updates are received from development, versioned according to the version strategy of Release Planning, moved into the test environment, moved form the test environment into the production environment after the pre release tests have been successfully completed.

Implementation Considerations

What units are subject to migration?

The groups of components, which are allowed to be migrated, must be determined, for example: single software modules or documents can be migrated on their own and only complete releases (including delta releases) with all their components may be migrated.

Where will the release library be located?

The library can either be held centrally or can be distributed over various sites. A centralized approach is preferable in order to avoid inconsistencies.

Which platforms and media are used for the release library?

The release library may reside of several platforms. UNIX software may be stored on UNIX servers, host software on hosts and third party workstation software may be on floppy disks.

License Management

License Management ensures that software licenses are being maintained throughout the distributed system and that license agreements are not being violated.

Implementation Considerations

What data will be stored?

There are four options to consider, when designing the scope of the Asset Management function. Usage of the Asset inventory only as a production system database (core database), including hardware devices, software versions loaded in the production environment, their licenses and network configuration data. Thus the asset inventory system only stores the core systems components in the production environment.

In addition to the production system data as describes above, it contains any existing release and release components such as software modules, documents and procedures. It also contains service level agreements and actual figures for user groups and devices, incidents, problems and change requests. It may also contain additional data such as performance data or log of all backups taken.

How will data be kept up-to-date?

This can be achieved by regular and ad hoc audits, using manual and automated procedures. An alternative approach would be to use asset data to drive Software & Data Distribution. The Software & Data Distribution processes would get data from the asset inventory system as input If these processes configured the devices according to the asset inventory it would be up-to-date by definition.

What phases of an assets life cycle should be covered by Asset Management?

It may be appropriate to control assets within the first stage of the life cycle (i.e., from development on) or it my prove more appropriate to implement Asset Management only from the point of delivery.

Product Considerations

What is the intended use of the tool?

Maintain a central repository for all software licenses and assets.

What other utilities are available with the tool?

Software asset tracking by location/server, automatic detection of correct level of software.

Authorize license use.

Perform periodic searches for unlicensed software.

Central inventory system

Ability to back up and archive the asset inventory system

What are some of the inventory maintenance issues that need to be addressed?

Ability to maintain a data model representing the basis for an asset inventory system that reflects the types of assets to be managed and their relationships. The model should be flexible to cope with future structural changes. A record needs to be added to the inventory system when an asset is purchased or created, or when changes to the environment are performed.

How well does the tool integrate with other tools in the environment?

Asset data needed to support various other management functions such as:

Hardware Maintenance
Release Testing
Procurement
Initial Installation
System Component Configuration
Software & Data Distribution.

Does the tool provide support for a specific environment?

Current asset data from the distributed environment needs to be retrieved frequently through regular and ad hoc audits.

Database Management (2038)

Database Management is the management and administration of database technologies, including monitoring, physical file placement, performance, and sizing.

Database Recovery

Database Recovery is the process of providing recovery of database entities following a logical or physical database failure. This includes database software failure and local disk failure.

Database Disaster Recovery

Database Disaster Recovery is the process of recovering the database entities following a catastrophic failure. This process should be fully integrated in the enterprise-wide disaster recovery plan.

Database Backup/Restore Management

Database Backup/Restore Management is the process of providing point-in-time backup and recovery for logical database restores. This includes application-driven data errors, dropped tables, and corrupt data.

Capacity Modeling & Planning

Capacity Modeling & Planning ensures that adequate resources will be in place to meet the SLA requirements, keeping in mind operational requirements which may require additional capacity. Resources can include such things as physical facilities, computers, memory/disk space, communications lines and personnel. Through this component, changes to the existing environment will be determined, modeled and planned according to the necessary requirements.

Implementation Considerations

What are some limitations that may be encountered?

Capacity Planning & Modeling must coordinate the requirements across the system (e.g., networks, servers, workstations, CPU, etc.) Capacity is driven by the need to meet SLAs with the user communities and as part of the planning and modeling process, future threats to capacity should be identified.

Capacity planning cannot, however, be done separately for each piece of the system. Capacity planning must be done for the system as a whole to understand how the capacity of one portion of the system affects the capacity of another. Due to the large number of components within a distributed environment with any-to-any connectivity that will affect the systems capacity, the equation for determining capacity quickly becomes large, with many interdependencies.

Monitoring (2040)

Verifies that the system is continually functioning in accordance with whatever service levels are defined.

Performance Management

Performance Management ensures that the required resources are available at all times throughout the distributed system to meet the agreed upon SLAs. This includes monitoring and management of end-to-end performance based on utilization, capacity, and overall performance statistics. If necessary, Performance Management can make adjustments to the production environment to either enhance performance or rectify degraded performance.

Implementation Considerations

What are some of the critical elements to focus on in a centralized environment and distributed environment?

Performance Management in a centralized environment typically focuses on three main factors: CPU utilization, disk I/O, memory occupancy.

Within the distributed environments, however, these factors extend out into the environment across networks, increasing the complexity of gathering the necessary performance information.

View performance as a typically business driven?

Performance Management needs to consider performance from a business perspective, not merely a systems one. Most transactions in distributed systems utilize a wide variety of resources, and the measurement of end-to-end response time becomes the sum of the time expended by each one of the components sequentially involved in the transaction less the time while components were processing in parallel.

What devices/users will be monitored and at which locations? Will this information change?

Understanding the scope of devices/users, and their locations is key to managing performance. Understanding whether or not the scope will change will help determine how Performance Management needs to be approached.

Will performance be measured from end-to-end or merely for individual components?

The issues associated with each of these approaches are described above. The approach chosen will have a profound effect on determining the issues that need to be resolved.

Will monitoring be continuous or by demand?

Continuous monitoring can generate significant performance overhead, whereas targeted, periodic monitoring may only be necessary. This strategy will impact the design of the technical infrastructure as well as the tools chosen the manage the systems performance.

Will only selected transactions be measured, and if so, should this selection be configurable?

It may be necessary to measure business critical transactions only; specified within the SLA. If the facility to select specific transactions is required, significant customization of the system may be necessary.

Will response times be required for all transactions of a particular type, or can sampling be used?

Once transaction have been selected for monitoring, the decision needs to be taken whether or not every transaction of that type should be monitored, or only a sample set of those transactions. Full monitoring may increase network and processing overheads.

The ability to dynamically adjust the system to improve performance is also critical?

As SLAs will likely be tied in some way to performance, it is important to monitor and correct the systems performance as it degrades to ensure that operational levels are maintained and that the SLA(s) will not be violated.

Product Considerations

What is the Intended use of the tool?

Collect, analyze and display in graphical format real-time performance characteristics from a wide range of resources. Analyze current workload and configuration data and forecast future requirements, as well as providing input into the Financial planning process.

What other utilities are available with the tool?

Provide real time monitoring and interactive tuning of the environment. Ability to input threshold alerting based on high/low watermarks and proactively act.

Monitoring capabilities include the ability to measure CPU and disk utilization, memory occupancy, transaction response time, reports (storage & distribution), printers, network utilization and performance, circuit utilization, backup facilities, WAN/LAN utilization.

Instance level tuning and configuration parameters (memory, I/O, journaling) to address performance problems.

Other integrated tools needed to provide support for this environment?

May require use of some or all of the following monitoring tools: operating system monitor, on-line monitor, batch monitor, data base monitor, (host, server) and network monitor (WAN, LAN).

How well does the tool integrate and interface with other tools/components in the environment?

Performance measures must be consistent with Service Level management techniques Performance statistics are essential to facilitate ongoing Capacity Planning and Modeling.

Resource utilization statistics may be used to generate costing, and potential billings for customers.

Passes data to the resource consumption management facility to report on the recurring processing cost of each business application.

Physical Site Management

Physical Site Management monitors the central and distributed sites environmental and regulatory levels. Physical Site Management ensures that adequate power, cooling facilities, fire suppression, etc. are provided and maintained to prevent system outages. When necessary, corrective actions are issued and monitored according to pre-defined environmental control plans.

Testing (2042)

Ensures that changes to the distributed environment will not negatively impact the distributed environment and that changes will cause positive things to take place (e.g., better system performance, improved operability, etc.)

Product Validation

Product Validation tests potential hardware and software for the distributed environment prior to procurement to determine how well a product will fulfill the requirements identified. Product Validation also ensures that the implementation of a new product will not adversely affect the existing environment.

Implementation Considerations

To what extent will the production environment be reflected?

The design of the test environment should reflect the production environment as closely as possible. In principle it is desirable to have an identical set up in both environments. However, this may be cost prohibitive and some parts of the configuration may not be critical to business. The contents of the test environment therefore need to be decided. Yet it is difficult to judge which components of a distributed environment may actually impact services. For example, networking components, such as bridges, are often seen as transparent and not required in a test environment, which my mean that several LANs in production are only reflected by one LAN in the test environment. The risk of adopting this approach must be addressed thoroughly, and should be approved be senior management.

What are some limitations that may be encountered within a distributed environment?

Because the technologies are new, it may not be possible to accurately assess what needs to be tested for a particular product. There are many configuration variants in the distributed environment, a single test environment for the validation becomes difficult to achieve and multiple test environments may be required.

Release Testing

Release Testing receives the proper version of a release package (e.g., software, data, procedures, support materials) and tests the release of the upgrade in a test environment to ensure that the:

- entire release package is compatible with the existing environment
- release package may be released successfully by the planned methods
- release can be supported by support personnel.

Implementation Considerations

To what extent will the production environment be reflected?

The design of the test environment should reflect the production environment as closely as possible. In principle it is desirable to have an identical set up in both environments. However, this may be cost prohibitive and some parts of the configuration may not be critical to business. The contents of the test environment therefore need to be decided. Yet it is difficult to judge which components of a distributed environment may actually impact services. For example, networking components, such as bridges, are often seen as transparent and not required in a test environment, which my mean that several LANs in production are only reflected by one LAN in the test environment. The risk of adopting this approach must be addressed thoroughly, and should be approved be senior management.

Will release tests cover the full business cycle and use full business volumes?

To ensure that the Operability Principles have been satisfied, each release should, in principle, undergo a release test of a full business cycle (to show that Operations can run it) and full business volumes (to show that SLA targets can be achieved). These tests are, however, expensive in terms of dedicated hardware requirements, people, and elapsed time.

In practice, Release Planning will propose an approach dependent on the magnitude and sensitivity of change for each release. The approach must be approved by senior management. If service levels are not to be compromised, major releases must undergo a full release test.

Repositories (2044)

Repositories contain all the management data generated or used during the management process. This includes historical data, capacity data, performance data, problem knowledge bases, asset databases, solution sets, and management information bases (MIBs). The repositories component interacts with the management applications, integration platform, supporting infrastructure, and presentation components. Again it is important to make sure that the other components of the operational architecture are compatible with the database tools.

Production Control (2046)

Ensures that production activities are performed and controlled as required and as intended.

Backup/Restore Management

Backup and Restore Management considers all of the back-up and restorations that need to take place across the distributed system for master copies of data. Depending on the need, these processes may occur centrally or remotely.

Archiving

Archiving saves and stores information across the distributed environment, either centrally or in distributed locations. Archiving moves data sets, files, etc. from one device to another, usually lower speed, device based on a number of parameters. Archiving can be used to move information to or from distributed and centralized sites.

Integration Platform (2048)

The integration platform provides a common platform for the operational architecture. At the lowest level this means deciding on common standards, interfaces, massage formats, and file logging forms to be used with all the management tools.

Lastly, some environments use a home grown integration platform. The choice of integration platforms depends upon its ability to integrate with the execution and development environments.

Network Management

Network & Systems Management Planning is responsible for the planning activities involved in running the day-to-day operations and maintenance of the production systems (e.g., capacity planning, performance planning, etc.).

Supporting Infrastructure (2050)

The supporting infrastructure is the subset of operating systems, utilities, languages, and protocols used to support the management of the system. The supporting infrastructure is most often determined by the execution and development environments and the business applications on the system. It is necessary to ensure that the other components of the operational architecture are compatible with the existing supporting infrastructure. This limits the number of possible tool set solutions. Examples of operating systems include HP-UX, AIX, Solaris, SCO, Novell NOS, MVS, OpenVMS, NT and DOS. Examples of support utilities include PS, GREP, IBCOPY, TAR, CPIO and clock correlation. Examples can be broken down according to their function within the OSI model. Session protocols include SNMP, CMIP, FTP, and RPC. Transport protocols include TCP and UDP. Network protocols include IP and IPX. Data-Link protocols include Token Ring, Ethernet, X.25, ATM, SONET, and Frame Relay.

Production Control (2052)

Ensures that production activities are performed and controlled as required and as intended.

File Transfer & Control

File Transfer and Control initiates and monitors files being transferred throughout the system as part of the business processing (e.g., nightly batch runs). File transfers may occur between any two or more devises within the system.

Implementation Considerations

What platforms will be involved in the file transfers?

The platforms will be determined by both the business and the technical requirements. This will impact the selection of the file transfer tools, and, in particular, how the file transfers are controlled from platform to platform.

How many files will be transferred? With what frequency?

The number of files to be transferred as well as their frequency will impact the capacity required on the system (e.g., network bandwidth) as well as the production schedule. In addition, if the volume of data is significant, data compression may be required.

Will store and forward be supported?

Store and forward techniques can help reduce the contention for system resources during business hours. Store and forward can also reduce the amount of traffic in the system based upon the routing tables defined within the system. Instead of having one machine send the same file to multiple machines, for instance, a cascading forwarding mechanism can be used. This also improves the system performance as files are sent a minimal number of times to certain devices which then forward the files on to other devices.

What are some limitations that may be encountered?

File transfers in a distributed environment are not confined between hosts. File transfers can take place in a bi-directional fashion between hosts, servers and workstations. Due to the geographical disparity and number of devices in these environments, file transfers will increase the traffic over the network and will require careful scheduling to ensure that the necessary file transfers take place amidst the rest of the processing.

Managing Hardware (2054)

Managing hardware is all hardware directly used to manage the environment. This includes all staging components. These components are devoted to systems management functions. Examples of managing hardware include management servers, management controllers, management consoles, probes, and sniffers. One significant component in the hardware monitoring arena is Firewall access control policy management. Firewalls are regularly used for network based security management. It is typically a system or group of systems that enforce access control between two or more networks and/or perform network data packet filtering. Usually packet filtering router hardware and application gateways are used to block unauthorized IP packets and enforce proxy defined user commands.

Failure Control (2056)

Involves the detection and correction of faults within the system whether they be minor (e.g., workstation is down) or major (i.e., a disaster) has occurred.

Disaster Recovery

In the event of a significant system failure, Disaster Recovery processes will be invoked to re-route the system resources to a secondary, stable configuration until the primary resources can be restored. Within a distributed environment, disaster recovery must account for differing levels of disaster whether at a central or distributed site(s).

Fault Management

When a negative event has been brought to the attention of the system, actions are undertaken within Fault Management to define, diagnose, and correct the fault. Although it may be possible to automate this process, human intervention may be required to perform at least some of these management tasks.

Implementation Considerations

What are some limitations that may be encountered?

In order to correct faults in a distributed environment, remote fault diagnosis and correction tools may also be required. It may not be possible to count on having technical expertise on-sites, forcing fault management to be handled from a centralized area. Products which perform these functions at present, however, provide somewhat limited capabilities in this arena.

Recovery

Recovery manages all of the actions needed to restore service delivery after a system failure. With critical business applications being rolled out on distributed technologies, the recovery of these systems must be easy, quick and efficient to guarantee availability of core business systems as expressed in the agreed service levels and operational levels.

Hardware Maintenance

Hardware Maintenance maintains all of the components within a distributed system to protect the investment of the organization. Generally agreed upon in the SLAs, maintenance contracts are carried out, monitored and recorded for each asset as appropriate.

Implementation Considerations

What will the Hardware Maintenance targets be?

Different hardware components will likely have different maintenance targets. These targets should be defined based upon information provided by the vendor as well as information provided from other client engagements.

Where will Hardware Maintenance be required?

Hardware Maintenance may be required at both the central and remote locations. Careful consideration must be given as to how the hardware at remote locations will be maintained (e.g., by a local expert, third-party vendor, etc.)

Monitoring (2058)

Verifies that the system is continually functioning in accordance with whatever service levels are defined.

Event Management

An event is an electronic message generated by any component (e.g., application software, system software, hardware, etc.) in the system. Event Management receives, logs, classifies and presents event messages on a console(s) based on pre-established filters or thresholds.

Implementation Considerations

What type of events will be monitored? More specifically, what services need to be monitored across which devices (e.g., servers, workstations, routers, hubs, bridges)?

The scope of events to be monitored will have a major impact on the approach taken for Event management and the tools selected.

Where will devices reside on the network, and how frequently will they be polled?

The number of devices, their respective locations and polling requirements will significantly contribute to network bandwidth usage.

Where can event filtering be applied?

In order to reduce bandwidth, it is preferable that event filtering be performed locally to avoid sending all event information across the network, utilizing bandwidth and central processing capability unnecessarily.

What management protocols need to be supported?

The protocol requirements will impact the selection of the tool. For more information on management protocols, refer to the management protocols using SNMP and CMIP as examples.

What are some of the limitations that may be encountered?

The number of events generated in the system will increase due to the complexity of the system. Devices will generate events as well as applications, the technical infrastructure, etc. Common event handling mechanisms will be required to provide management information in a simple, consistent format and to forward important events on for management purposes. In addition, filtering capabilities may also be needed at remote locations to prevent the streaming of events to central/master management consoles.

Performance Management

Performance Management ensures that the required resources are available at all times throughout the distributed system to meet the agreed upon SLAs. This includes monitoring and management of end-to-end performance based on utilization, capacity, and overall performance statistics. If necessary, Performance Management can make adjustments to the production environment to either enhance performance or rectify degraded performance.

Physical Site Management

Physical Site Management monitors the central and distributed sites environmental and regulatory levels. Physical Site Management ensures that adequate power, cooling facilities, fire suppression, etc. are provided and maintained to prevent system outages. When necessary, corrective actions are issued and monitored according to pre-defined environmental control plans.

Implementation Considerations

What are some of the limitations that may encountered?

Important to ensure that adequate power, cooling facilities, fire suppression, etc. are provided and maintained to prevent system outages from external environmental factors. With increased computing power at multiple sites, these tasks may not be simple.

Physical Environment (2060)

The physical environment includes all the support indirectly involved in maintaining and managing the distributed environment. Initially it was thought client/server technology would make data centers obsolete. However, with the migration of mission critical processes to client/server environments, many servers are being maintained in data centers in an effort to increase reliability. As a result, the importance of managing the physical environment has increased. Partially because it was initially believed not to be very important and because it does not relate directly to the information systems, the physical environment of the operational architecture is often overlooked. These systems include UPS, raised floor, power, site survey and preparation, wiring/cabling, climate control, etc.

Related MODE functions The breakdown the MODE functions by operational architecture layer is meant to provide a guideline. The MODE functions mentioned within each component are applicable to that component though the function may not be included in that component. For example, Physical Site Management relates to the physical environment in that the physical environment contains the hardware managed through Physical Site Management. Physical Site Management tools do not necessarily reside in the physical environment layer. Some MODE functions do not require the use of a tool, while other MODE functions have tool solutions that work in different ways. For this reason some functions were included in multiple layers while other functions were omitted.

Implementing (2062)

Executes change within the distributed environment with tested components and techniques according to the appropriate plan(s). Implementing includes such things as: initial installation, software & data distribution, license management, etc.

Initial Installation

Initial Installation prepares the physical location for the rollout of a new site or service, pre-assembles the equipment (hardware and software) based on developed specifications, installs the equipment and tests that the equipment is fully functional prior to allowing the users to utilize the system in a production environment.

Implementation Considerations

Some guiding principles:

Precise build procedures must be delivered early enough to drive Release Testing, Procurement, and rollout plans. It must be clear exactly what the install process will cover. Who will perform which tasks when and where? Software and Data must be available in time to create copies for the hangar. This means development teams need to ensure availability of software up to a number of weeks before going live.

To what extent will configuration be performed centrally prior to installation?

Some of the configuration tasks can be performed in a central hangar. Assembly of the machines may include configuration and software installation. Only minor tasks, such as setting networking addresses have to be performed after the equipment has been delivered to the remote site.

Product Considerations

What is the intended use of the tool?

Prepare physical locations and devices (both HW and SW) for new rollout based on developed specifications and perform installation and functional testing of new devices prior to release to the users.

What other utilities are available with the tool?

Initial Installation must be able to load rapidly, reliably and consistently a large number of devices with a standard configuration. Automatic update of asset data accordingly, asset inventory must reflect the actual state of the devices; their set up and their networking address.

How well does the tool integrate with other tools in the environment?

During Initial Installation, software and data is loaded at the machines. The Software & Data Distribution function may be used to ship software and data to the location where it is to be installed (e.g. remote sites).

Procurement

Procurement is responsible for ensuring that the necessary quantities of equipment (both hardware and software) are purchased and delivered on-time to the appropriate locations. Procurement is also responsible for logging all assets into the inventory as they are received.

Implementation Considerations

Will Equipment be resourced from multiple or single suppliers?

It is likely that organization will have close and long-term relationships to certain suppliers. In many cases, suppliers will offer discounts to their most loyal customers. These partnerships are advantageous for both sides, as long as they do not lead to supplier lock-in, i.e. the organization becomes technically dependent on one supplier. Technical portability and interoperability help support independence.

What will be the payment policy (immediate or delayed)?

A management decision is required, which compares cash flow benefits through payment as late as possible against discounts for early payment. This will usually be an extension of an existing policy.

Monitoring (2064)

Verifies that the system is continually functioning in accordance with whatever service levels are defined.

Physical Site Management

Physical Site Management monitors the central and distributed sites environmental and regulatory levels. Physical Site Management ensures that adequate power, cooling facilities, fire suppression, etc. are provided and maintained to prevent system outages. When necessary, corrective actions are issued and monitored according to pre-defined environmental control plans.

Although only a few embodiments of the present invention have been described in detail herein, it should be understood that the present invention may be embodied in many other specific forms without departing from the spirit or scope of the invention. Therefore, the present examples and embodiments are to be considered as illustrative and not restrictive, and the invention is not to be limited to the details given herein, but may be modified within the scope of the appended claims.

What is claimed is:

1. A method for generating error and summary reports for a data load, while storing user input data files in a multi-tier client/server architecture such that the data files are organized around tiers of keywords, comprising the steps of:
    (a) maintaining a connection between multiple user stations and a server having a database;
    (b) selecting a plurality of user-selected keywords from a user interface, wherein each keyword is associated to a data file name and a data type, also wherein the plurality of keywords are arranged in the user interface in a tier structure such that keywords in a first tier are associated to data files that must be loaded into the database before data files associated to a second tier are loaded into the database;
    (c) receiving from one of the user stations a plurality of user input data files that are associated to the selected plurality of keywords;
    (d) selecting a data management template corresponding to the keywords, wherein the data management template organizes the data files to be loaded into the database;
    (e) validating that all data to be loaded into the database match the data management template by enforcing business rules and requirements and ensuring that referential integrity, codependency, primary key, required field, default field, sequence number, and hard-coded field checks are met;
    (f) loading the validated data into the database;
    (g) compiling a report identifying data that match the data management template and data that do not match the data management template; and
    (h) providing said compiled report to said user for review.

2. A method as recited in claim 1, wherein no data are loaded into the database if any of the data does not match the data management template.

3. A method as recited in claim 1, wherein the user input data files are medical files.

4. A method as recited in claim 1, further comprising the steps of separating data that match the data management template from data that do not match the data management template, and sending the data that do not match the data management template to the user station.

5. A method as recited in claim 1, further comprising the step of sending a notification upon detecting a concurrently executing load process.

6. A computer program embodied on a computer readable medium for generating error and summary reports for a data load, while storing user input data files in a multi-tier client/server architecture such that the data files are organized around tiers of keywords, comprising:
    (a) a code segment that maintains a connection between multiple user stations and a server having a database;
    (b) a code segment that selects a plurality of user-selected keywords from a user interface, wherein each keyword is associated to a data file name and a data type, also wherein the plurality of keywords are arranged in the user interface in a tier structure such that keywords in a first tier are associated to data files that must be loaded into the database before data files associated to a second tier are loaded into the database;
    (c) a code segment that receives from one of the user stations a plurality of user input data files that are associated to the selected plurality of keywords;
    (d) a code segment that selects a data management template corresponding to the keywords, wherein the data management template organizes the data files to be loaded into the database;
    (e) a code segment that validates that all data to be loaded into the database matches the data management template by enforcing business rules and requirements and ensuring that referential integrity, codependency, primary key, required field, default field, sequence number, and hard-coded field checks are met;
    (f) a code segment that loads the validated data into the database;
    (g) a code segment that compiles a report identifying data that match the data management template and data that do not match the data management template; and
    h) a code segment that provides said compiled report to said user for review.

7. A computer program embodied on a computer readable medium as recited in claim 6, wherein no data are loaded into the database if any of the data does not match the data management template.

8. A computer program embodied on a computer readable medium as recited in claim 6, wherein the user input data files are medical files.

9. A computer program embodied on a computer readable medium as recited in claim 6, further comprising a code segment that separates data that match the data management template from data that do not match the data management template, and sends the data that do not match the data management template to the user station.

10. A computer program embodied on a computer readable medium as recited in claim 6, further comprising a code segment that sends a notification upon detecting a concurrently executing load process.

* * * * *